US008435544B2

(12) United States Patent
Mitra et al.

(10) Patent No.: US 8,435,544 B2
(45) Date of Patent: May 7, 2013

(54) OPHTHALMIC COMPOSITIONS COMPRISING CALCINEURIN INHIBITORS OR MTOR INHIBITORS

(75) Inventors: Ashim K. Mitra, Overland Park, KS (US); Poonam R. Velagaleti, Randolph, NJ (US); Subramanian Natesan, Triuchirappalli (IN)

(73) Assignee: Lux Biosciences, Inc., Jersey City, NJ (US)

( * ) Notice: Subject to any disclaimer, the term of this patent is extended or adjusted under 35 U.S.C. 154(b) by 1106 days.

(21) Appl. No.: 12/247,701

(22) Filed: Oct. 8, 2008

(65) Prior Publication Data

US 2009/0092665 A1 Apr. 9, 2009

Related U.S. Application Data

(60) Provisional application No. 60/997,796, filed on Oct. 8, 2007, provisional application No. 60/992,205, filed on Dec. 4, 2007, provisional application No. 61/038,223, filed on Mar. 20, 2008, provisional application No. 61/099,420, filed on Sep. 23, 2008.

(51) Int. Cl.
*A61K 9/00* (2006.01)
*A61K 9/127* (2006.01)
*A01N 43/42* (2006.01)
*A01N 43/16* (2006.01)

(52) U.S. Cl.
USPC ............ 424/400; 424/450; 514/291; 514/458

(58) Field of Classification Search ........................ None
See application file for complete search history.

(56) References Cited

U.S. PATENT DOCUMENTS

| | | | |
|---|---|---|---|
| 3,244,592 A | 4/1966 | Tadashi | 167/65 |
| 4,039,662 A | 8/1977 | Hecht | 424/180 |
| 4,117,118 A | 9/1978 | Harri | 424/177 |
| 4,120,949 A | 10/1978 | Bapatla | 424/80 |
| 4,409,205 A | 10/1983 | Shively | 424/78 |
| 4,649,047 A | 3/1987 | Kaswan | 424/78 |
| 4,744,980 A | 5/1988 | Holly | 424/78 |
| 4,795,643 A | 1/1989 | Seth | 424/456 |
| 4,804,539 A | 2/1989 | Guo | 424/450 |
| 4,839,342 A | 6/1989 | Kaswan | 514/11 |
| 4,865,846 A | 9/1989 | Kaufman | 424/428 |
| 4,883,658 A | 11/1989 | Holly | 424/80 |
| 5,051,402 A | 9/1991 | Kurihara | 514/11 |
| 5,075,104 A | 12/1991 | Gressel | 424/78.04 |
| 5,110,493 A | 5/1992 | Cherng-Chyi | 514/413 |
| 5,188,826 A | 2/1993 | Chandrasekaran | 424/78.04 |
| 5,209,927 A | 5/1993 | Gressel | 424/78.04 |
| 5,227,372 A | 7/1993 | Folkman | 514/58 |
| 5,252,246 A | 10/1993 | Ding | 252/174.21 |
| 5,252,318 A | 10/1993 | Joshi | 424/78.04 |
| 5,326,761 A | 7/1994 | Rozier | 514/235.8 |
| 5,342,625 A | 8/1994 | Hauer | 424/455 |
| 5,360,611 A | 11/1994 | Robertson | 424/427 |
| 5,387,589 A | 2/1995 | Kulkarni | 514/291 |
| 5,401,510 A | 3/1995 | Robertson | 424/427 |
| 5,411,952 A | 5/1995 | Kaswan | 514/11 |
| 5,414,011 A * | 5/1995 | Fu et al. | 514/413 |
| 5,441,732 A | 8/1995 | Hoeg | 424/78.04 |
| 5,474,979 A | 12/1995 | Ding | 514/11 |
| 5,496,861 A | 3/1996 | Rouse et al. | |
| 5,540,931 A | 7/1996 | Hewitt | 424/434 |
| 5,558,876 A | 9/1996 | Desai | 424/427 |
| 5,576,025 A | 11/1996 | Akiyama et al. | |
| 5,585,406 A | 12/1996 | Ding | 514/772 |
| 5,591,426 A | 1/1997 | Dabrowski | 424/78.04 |
| 5,599,534 A | 2/1997 | Himmelstein | 424/78.04 |
| 5,607,698 A | 3/1997 | Martin | 424/613 |
| 5,624,893 A | 4/1997 | Yanni | 514/21 |
| 5,643,870 A | 7/1997 | Boelsterli | 514/11 |
| 5,698,219 A | 12/1997 | Valdivia | 424/450 |
| 5,698,533 A | 12/1997 | Kang | 514/52 |
| 5,741,512 A | 4/1998 | Hauer | 424/450 |
| 5,770,628 A | 6/1998 | Cantoro | 514/778 |
| 5,773,019 A | 6/1998 | Ashton | 424/423 |
| 5,798,333 A | 8/1998 | Sherman | 514/11 |
| 5,814,655 A | 9/1998 | Patel | 514/413 |

(Continued)

FOREIGN PATENT DOCUMENTS

| | | |
|---|---|---|
| EP | 0349061 | 3/1995 |
| EP | 0 868 909 | 10/1998 |

(Continued)

OTHER PUBLICATIONS

Adis R&D Profile "ISA247", Drugs R D, 8(2), 2007, pp. 103-112.*
Lee et al., Pharmacokinetics and organ distribution of cyclosporin A incorporated in liposomes and mixed micelle, International Journal of Pharmaceutics, 191, 1999, pp. 87-93.*
Benitez del Castillo et al. Influence of Topically Applied Cyclosporine A in Olive Oil on Corneal Epithelium Permeability. Cornea vol. 13(2):136-40, Mar. 1994.
Blanco-Fuente et al. Tanned Leather: A Good Model for Determining Hydrogels Bioadhesion. International Journal of Pharmaceutics, vol. 138(1):103-112, Jul. 12, 1996.
Bonduelle et al. Tissue Concentration of Nanoencapsulated Radio-Labelled Cyclosporin Following Peroral Delivery in Mice or Ophthalmic Application in Rabbits. European Journal of Pharmacology and Biopharmaceutics, vol. 42(5):313-319, Oct. 19, 1996.

(Continued)

*Primary Examiner* — Daniel Sullivan
*Assistant Examiner* — Melissa Javier
(74) *Attorney, Agent, or Firm* — Greenberg Traurig, LLP; David J. Dykeman; Fang Xie

(57) ABSTRACT

The embodiments disclosed herein relate to ophthalmic compositions comprising calcineurin inhibitors or mTOR inhibitors, and more particularly to methods for treating an ocular disease and/or condition using the disclosed compositions. According to aspects illustrated herein, there is provided a pharmaceutical composition that includes a calcineurin inhibitor or an mTOR inhibitor; a first surfactant with an HLB index greater than about 10; and a second surfactant with an HLB index of greater than about 13, wherein an absolute difference between the HLB index of the first surfactant and the HLB index of the second surfactant is greater than about 3, and wherein the composition forms mixed micelles.

49 Claims, 19 Drawing Sheets

U.S. PATENT DOCUMENTS

| | | | | |
|---|---|---|---|---|
| 5,830,508 | A | 11/1998 | MacKeen | 424/602 |
| 5,843,891 | A | 12/1998 | Sherman | 514/11 |
| 5,866,159 | A | 2/1999 | Hauer | 424/450 |
| 5,869,103 | A | 2/1999 | Yeh | 424/501 |
| 5,886,030 | A | 3/1999 | Maniar | 514/458 |
| 5,916,589 | A | 6/1999 | Hauer | 424/450 |
| 5,962,014 | A | 10/1999 | Hauer | 424/450 |
| 5,962,017 | A | 10/1999 | Hauer | 424/450 |
| 5,998,365 | A | 12/1999 | Sherman | 514/11 |
| 6,007,840 | A | 12/1999 | Hauer | 424/450 |
| 6,024,978 | A | 2/2000 | Hauer | 424/450 |
| 6,071,958 | A | 6/2000 | Jimenez-Bayardo | 514/535 |
| 6,165,500 | A | 12/2000 | Cevc | 424/450 |
| 6,193,985 | B1 | 2/2001 | Sonne | |
| 6,217,895 | B1 | 4/2001 | Guo et al. | |
| 6,254,860 | B1 | 7/2001 | Garst | |
| 6,254,893 | B1 | 7/2001 | MacKeen | 424/602 |
| 6,284,235 | B1 | 9/2001 | Foreman et al. | |
| 6,309,569 | B1 | 10/2001 | Farrar | 264/4.1 |
| 6,309,630 | B1 | 10/2001 | Patel | 424/78.04 |
| 6,350,442 | B2 | 2/2002 | Garst | |
| 6,406,719 | B1 | 6/2002 | Farrar | 424/489 |
| 6,565,777 | B2 | 5/2003 | Farrar | 264/4.1 |
| 6,677,304 | B2 | 1/2004 | Di Napoli | 514/9 |
| 6,713,081 | B2 | 3/2004 | Robinson | 424/427 |
| 6,809,077 | B2 | 10/2004 | Or | 514/11 |
| 6,814,966 | B1 | 11/2004 | Wax | |
| 6,828,356 | B2 | 12/2004 | Su | 523/105 |
| 6,872,382 | B1 | 3/2005 | Gamache | 424/78.04 |
| 6,923,988 | B2 | 8/2005 | Patel | 424/489 |
| 6,953,776 | B2 | 10/2005 | Di Napoli | 514/11 |
| 6,979,671 | B2 | 12/2005 | Or | 514/2 |
| 6,982,282 | B2 | 1/2006 | Lambert | 514/511 |
| 6,984,628 | B2 | 1/2006 | Bakhit | 514/21 |
| 6,998,385 | B2 | 2/2006 | Naicker | 514/11 |
| 7,001,615 | B1 | 2/2006 | Singh | 424/488 |
| 7,012,064 | B2 | 3/2006 | Or | 514/11 |
| 7,012,065 | B2 | 3/2006 | Or | 514/11 |
| 7,026,290 | B1 | 4/2006 | Domb | 514/11 |
| 7,033,604 | B2 | 4/2006 | Ueno | 424/427 |
| 7,048,946 | B1 | 5/2006 | Wong et al. | |
| 7,060,672 | B2 * | 6/2006 | Naicker et al. | 424/439 |
| 7,083,803 | B2 | 8/2006 | Peyman | 424/422 |
| 7,087,237 | B2 | 8/2006 | Peyman | 424/400 |
| 7,202,209 | B2 | 4/2007 | Chang et al. | |
| 7,214,664 | B2 | 5/2007 | Mitra | 514/19 |
| 7,276,476 | B2 | 10/2007 | Chang et al. | |
| 7,288,520 | B2 | 10/2007 | Chang et al. | |
| 7,297,679 | B2 | 11/2007 | Chang et al. | |
| 7,351,741 | B2 | 4/2008 | Weidner | 514/557 |
| 7,361,636 | B2 | 4/2008 | Molino | 514/11 |
| 7,378,391 | B2 | 5/2008 | Molino | 514/9 |
| 7,429,562 | B2 | 9/2008 | Naicker | 514/2 |
| 7,468,419 | B2 | 12/2008 | Wu et al. | |
| 7,501,393 | B2 | 3/2009 | Tien et al. | |
| 7,511,013 | B2 | 3/2009 | Molino et al. | |
| 7,557,082 | B2 | 7/2009 | Schiffman | |
| 7,605,275 | B2 | 10/2009 | Mudumba | |
| 7,632,807 | B2 | 12/2009 | Molino et al. | |
| 7,655,625 | B2 | 2/2010 | Brin | |
| 7,745,400 | B2 | 6/2010 | Feinerman et al. | |
| 7,833,966 | B2 | 11/2010 | Peyman | |
| 7,846,468 | B2 | 12/2010 | Wong | |
| 7,846,478 | B2 | 12/2010 | Ameye et al. | |
| 7,846,479 | B2 | 12/2010 | Fang | |
| 7,893,040 | B2 | 2/2011 | Loftsson | |
| 8,003,124 | B2 | 8/2011 | Varner | |
| 8,043,628 | B2 | 10/2011 | Wong | |
| 8,067,433 | B2 | 11/2011 | Chappell et al. | |
| 8,071,120 | B2 | 12/2011 | Wong | |
| 8,207,129 | B2 | 6/2012 | Schiffman | |
| 8,211,855 | B2 | 7/2012 | Chang | |
| 2001/0041671 | A1 | 11/2001 | Napoli | 514/9 |
| 2003/0018044 | A1 | 1/2003 | Peyman | 514/291 |
| 2003/0044452 | A1 | 3/2003 | Ueno | 424/449 |
| 2003/0143277 | A1 | 7/2003 | Ameye et al. | |
| 2003/0165545 | A1 | 9/2003 | Huth | |
| 2004/0048777 | A1 | 3/2004 | Weidner | 514/2 |
| 2004/0106546 | A1 | 6/2004 | Napoli | 514/11 |
| 2004/0110666 | A1 | 6/2004 | Or | 514/9 |
| 2004/0156913 | A1 | 8/2004 | Fang | 424/489 |
| 2004/0266669 | A1 | 12/2004 | Wu | 514/2 |
| 2005/0014691 | A1 | 1/2005 | Bakhit | 514/12 |
| 2005/0031697 | A1 | 2/2005 | Vehige et al. | |
| 2005/0048098 | A1 | 3/2005 | Wong et al. | |
| 2005/0059583 | A1 | 3/2005 | Acheampong | 514/11 |
| 2005/0063996 | A1 | 3/2005 | Peyman | 424/400 |
| 2005/0063997 | A1 | 3/2005 | Peyman | 424/400 |
| 2005/0119160 | A1 | 6/2005 | Keith | 514/2 |
| 2005/0152980 | A1 | 7/2005 | Ausborn | 424/489 |
| 2005/0181018 | A1 | 8/2005 | Peyman | 424/427 |
| 2005/0191334 | A1 | 9/2005 | Wong et al. | |
| 2005/0277584 | A1 | 12/2005 | Tien | 514/11 |
| 2006/0034799 | A1 | 2/2006 | Brines | 424/85.1 |
| 2006/0034892 | A1 | 2/2006 | Ueno | 424/427 |
| 2006/0052340 | A1 | 3/2006 | Tsuzuki | 514/57 |
| 2006/0067966 | A1 | 3/2006 | Wong et al. | |
| 2006/0069015 | A1 | 3/2006 | Molino | 514/9 |
| 2006/0069016 | A1 | 3/2006 | Molino | 514/9 |
| 2006/0074015 | A1 | 4/2006 | Molino | 514/11 |
| 2006/0110428 | A1 | 5/2006 | deJuan | 424/427 |
| 2006/0116428 | A1 | 6/2006 | Jimenez-Bayardo | 514/738 |
| 2006/0148686 | A1 | 7/2006 | Xia | 514/11 |
| 2006/0177430 | A1 | 8/2006 | Bhushan | 424/94.1 |
| 2006/0183698 | A1 | 8/2006 | Abelson | 514/35 |
| 2006/0198871 | A1 | 9/2006 | Wong | |
| 2006/0204543 | A1 | 9/2006 | Wong et al. | |
| 2006/0204548 | A1 | 9/2006 | Nivaggioli et al. | |
| 2006/0217309 | A1 | 9/2006 | Naicker et al. | |
| 2006/0228414 | A1 | 10/2006 | Cook | 424/469 |
| 2006/0257450 | A1 | 11/2006 | Mudumba | 424/427 |
| 2006/0257451 | A1 | 11/2006 | Varner | 424/427 |
| 2006/0280774 | A1 | 12/2006 | Wong et al. | |
| 2007/0015691 | A1 | 1/2007 | Chang | 514/11 |
| 2007/0015693 | A1 | 1/2007 | Chang et al. | |
| 2007/0020336 | A1 | 1/2007 | Loftsson et al. | |
| 2007/0043006 | A1 | 2/2007 | Bingaman | 514/171 |
| 2007/0078077 | A1 * | 4/2007 | Peyman | 514/2 |
| 2007/0087962 | A1 | 4/2007 | Tien | 514/11 |
| 2007/0092539 | A1 | 4/2007 | Jimenez-Bayardo | 424/400 |
| 2007/0105761 | A1 | 5/2007 | Chappell et al. | |
| 2007/0141115 | A1 | 6/2007 | Kunzler | 424/427 |
| 2007/0149447 | A1 | 6/2007 | Chang et al. | |
| 2007/0167358 | A1 | 7/2007 | Feinerman et al. | |
| 2007/0191266 | A1 | 8/2007 | Brin | |
| 2007/0219127 | A1 | 9/2007 | Walt | |
| 2007/0299004 | A1 | 12/2007 | Acheampong et al. | |
| 2008/0009436 | A1 | 1/2008 | Chang | 514/9 |
| 2008/0021101 | A1 | 1/2008 | Jimenez-Bayardo | 514/530 |
| 2008/0039378 | A1 | 2/2008 | Graham | 514/11 |
| 2008/0050420 | A1 | 2/2008 | Wong | |
| 2008/0050421 | A1 | 2/2008 | Wong | |
| 2008/0069859 | A1 | 3/2008 | Wong | |
| 2008/0070834 | A1 | 3/2008 | Chang | 514/11 |
| 2008/0124377 | A1 | 5/2008 | Wong et al. | |
| 2008/0146497 | A1 | 6/2008 | Graham et al. | |
| 2008/0207494 | A1 | 8/2008 | Chang et al. | |
| 2008/0207495 | A1 | 8/2008 | Graham | 514/11 |
| 2008/0249002 | A1 | 10/2008 | Molino et al. | |
| 2009/0062249 | A1 | 3/2009 | Wong | |
| 2009/0092665 | A1 | 4/2009 | Mitra et al. | |
| 2009/0131307 | A1 | 5/2009 | Tien et al. | |
| 2009/0148499 | A1 | 6/2009 | Wong et al. | |
| 2009/0196905 | A1 | 8/2009 | Spada et al. | |
| 2009/0264348 | A1 | 10/2009 | Schiffman | |
| 2010/0310642 | A1 | 12/2010 | Mitra et al. | |
| 2011/0300195 | A1 | 12/2011 | Mitra et al. | |

FOREIGN PATENT DOCUMENTS

| | | |
|---|---|---|
| EP | 0724452 | 5/2000 |
| WO | WO 9614829 | 5/1996 |
| WO | WO 00/40219 | 7/2000 |
| WO | WO 03/032949 | 4/2003 |
| WO | WO 03/033526 | 4/2003 |
| WO | WO 03/033527 | 4/2003 |
| WO | WO 03/051351 | 6/2003 |
| WO | WO 2004/089960 | 10/2004 |

| WO | WO 2004/096261 | 11/2004 |
| WO | WO 2006/001963 | 1/2006 |
| WO | WO 2006/028361 | 3/2006 |
| WO | WO 2006/036614 | 4/2006 |
| WO | WO 2006/086744 | 8/2006 |
| WO | WO 2008/002118 | 1/2008 |
| WO | WO 2009/048929 | 4/2009 |
| WO | WO 2010/144194 | 12/2010 |

OTHER PUBLICATIONS

Chang et al. The Effect of Water-Soluble Vitamin E on Cyclosporine Pharmacokinetics in Healthy Volunteers. Clinical Pharmacology & Therapeutics, 59(3):297-303, Mar. 1996.

Cosar et al. Topical Cyclosporine in Pediatric Keratoplasty. Eye & Contact Lens, vol. 29(2)103-107, Apr. 2003.

Dumont et al. The Immunosuppressive and Toxic Effects of FK-506 Are Mechanistically Related: Pharmacology of a Novel Antagonist of FK-506 and Rapamycin. Journal of Experimental Medicine, vol. 176(3):751-60, Sep. 1, 1992.

Feske et al. $Ca^{2+}$/Calcineurin Signalling in Cells of the Immune System. Biochemical and Biophysical Research Communications vol. 311(4):1117-1132, Nov. 28, 2003.

Gummert et al. Newer Immunosuppressive Drugs: A Review. Journal of the American Society of Nephrology, vol. 10(6):1366-80, Jun. 1999.

Hackett & McDonald. Ophthalmic Toxicology and Assessing Ocular Irritation. Dermatoxicology, 5th Edition. Ed. F.N. Marzulli and H.I. Maibach. Washington, D.C.: Hemisphere Publishing Corporation. pp. 299-305 and 557-566. 1996.

Henriksen et al. Bioadhesion of Hydrated Chitosans: An In Vitro and In Vivo Study. International Journal of Pharmaceutics. vol. 145(1-2):231-240, Dec. 6, 1996.

Izci et al. Histologic Characteristics and Local Cellular Immunity of the Gland of the Third Eyelid After Topical Ophthalmic Administration of 2% Cyclosporine for Treatment of Dogs With Keratoconjunctivitis Sicca. American Journal of Veterinary Research, vol. 63(5):688-694, May 2002.

Kaswan et al. Spontaneous Canine Keratoconjunctivitis Sicca. A Useful Model for Human Keratoconjunctivitis Sicca: Treatment With Cyclosporine Eye Drops. Archives of Ophthalmology, vol. 107(8):1210-1216, Aug. 1989.

Liu et al. Calcineurin is a Common Target of Cyclophilin-Cyclosporin A and FKBP-FK506 Complexes. Cell, vol. 66(4):807-815, Aug. 23, 1991.

Lukyanov et al. Polyethylene Glycol-Diacyllipid Micelles Demonstrate Increased Accumulation in Subcutaneous Tumors in Mice. Pharmaceutical Research. vol. 19(10):1424-1429, Oct. 2002.

Marszall. Measurement of effective HLB values using a non-ionic surfactant phenol titration method. Parfumerie, Kosmetik. vol. 60:444-448, Jan. 1979.

Mu et al. Mixed Micelles Made of Poly(Ethylene Glycol)—Phosphatidylethanolamine Conjugate and D-A-Tocopheryl Polyethylene Glycol 1000 Succinate as Pharmaceutical Nanocarriers for Camptothecin. International Journal of Pharmaceutics, vol. 306(1-2):142-149, Dec. 8, 2005.

Olivero et al. Clinical Evaluation of 1% Cyclosporine for Topical Treatment of Keratoconjunctivitis Sicca in Dogs. Journal of the American Veterinary Medical Association, vol. 199(8):1039-1042, Oct. 15, 1991.

Robert et al. Experimental-Method for Bioadhesive Testing of Various Polymers. Acta Pharmaceutica Technologica-International Journal of Drug Formulation and Biopharmaceutics, vol. 34(2):95-98, Jun. 1988.

Rommp. Chemistry Lexicon, 8th Edition. Franck'shce Verlagshandlung, Stuttgart, p. 1750, 1983.

Rusnak & Mertz. Calcineurin: Form and Function. Physiological Reviews, vol. 80(4):1483-1521, Oct. 2000.

Sugita et al. A New Calcineurin Inhibitor, Pimecrolimus, Inhibits the Growth of *Malassezia* Spp. Antimicrobial Agents and Chemotherapy, vol. 50(8):2897-2898, Aug. 2006.

Tobyn et al. Factors Affecting In-Vitro Gastric Mucoadhesion .1. Test Conditions and Instrumental Parameters. European Journal of Pharmaceutics and Biopharmaceutics. vol. 41(4):235-241, Aug. 1995.

Tobyn et al. Factors Affecting In-Vitro Gastric Mucoadhesion .2. Physical Properties of Polymers. European Journal of Pharmaceutics and Biopharmaceutics. vol. 42(1):56-61, Jan. 1996.

Wu and Hopkins. Characteristics of D-Alpha-Tocopheryl PEG 1000 Succinate for Applications as an Absorption Enhancer in Drug Delivery Systems. Pharmaceutical Technology, vol. 23(10):52-60. Oct. 1999.

Anglade, E. et al., Next-Generation Calcineurin Inhibitors for Ophthalmic Indications, *Expert Opin. Investig. Drugs*, vol. 16, No. 10, pp. 1525-1540 (Oct. 2007).

Booth, B. et al., Sustained-Release Ophthalmic Drug Delivery Systems for Treatment of Macular Disorders, *Drugs & Aging*, vol. 24, No. 7, pp. 581-602 (Jul. 2007).

delAmo, E. et al., Current and Future Ophthalmic Drug Delivery Systems: A Shift to the Posterior Segment, *Drug Discovery Today*, vol. 13, Nos. 3/4, pp. 135-143 (Feb. 2008).

Granelli-Piperno, A. et al., Lymphokine and Nonlymphokine mRNA Levels in Stimulated Human T Cells, *J. Exp. Med.*, vol. 163, pp. 922-937 (Apr. 1986).

Hackett et al., Assessing Ocular Irritation. *Dermatoxicology*, 5th Edition, edited by F.N. Marzulli and H.I. Maibach. Washington, D.C.: Taylor & Francis Publishers, Chapter 44, pp. 557-571 (1996).

Hackett et al., Opthalmic Toxicology. *Dermatoxicology*, 5th Edition, edited by F.N. Marzulli and H.I. Maibach. Washington, D.C.: Taylor & Francis Publishers, Chapter 23, pp. 299-306 (1996).

Hackett et al., Eye Irritation. *Dermatoxicology*, 4th Edition, edited by F.N. Marzulli and H.I. Maibach. Washington, D.C.: Hemisphere Publishing Corporation, Chapter 31, pp. 749-815 (1991).

Hu, X. et al., Biodegradable Amphiphilic Polymer-Drug Conjugate Micelles, *Expert Opin. Drug Deliv.*, vol. 6, No. 10, pp. 1079-1090 (Oct. 2009).

Hughes, P. et al., Topical and Systemic Drug Delivery to the Posterior Segments, *Advanced Drug Delivery Reviews*, vol. 57, pp. 2010-2032 (Nov. 10, 2005).

Kaur, I. et al., Ocular Preparations: The Formulation Approach, *Drug Development and Industrial Pharmacy*, vol. 28, No. 5, pp. 473-493 (May 2002).

Koevary, Steven, Pharmacokinetics of Topical Ocular Drug Delivery: Potential Uses for the Treatment of Diseases of the Posterior Segment and Beyond, *Current Drug Metabolism*, vol. 4, No. 3., pp. 213-222 (Jun. 2003).

Komai, Y. et al., The Three-Dimensional Organization of Collagen Fibrils in the Human Cornea and Sclera, *Investigative Ophthalmology & Visual Science*, vol. 32, No. 8, pp. 2244-2258 (Jul. 1991).

Loftsson, T., et al., Topical Drug Delivery to the Posterior Segment of the Eye: Anatomical and Physiological Considerations, *Pharmazie*, vol. 63, No. 3, pp. 171-179 (Mar. 2008).

Mainardes, R.M., Colloidal Carriers for Ophthalmic Drug Delivery, *Current Drug Targets*, vol. 6, No. 3, pp. 363-371 (May 2005).

Mannermaa, E. et al., Drug Transport in Corneal Epithelium and Blood-Retina Barrier: Emerging Role of Transporters in Ocular Pharmacokinetics, *Advanced Drug Delivery Reviews*, vol. 58, Issue 11, pp. 1136-1163 (Sep. 16, 2006).

Maurice, David M., PhD., Drug Delivery to the Posterior Segment From Drops, *Survey of Ophthalmology*, vol. 47, Supp. 1, pp. S41-S52 (Aug. 2002).

Rabinovich-Guilatt, L., et al., Cationic Vectors in Ocular Drug Delivery, *Journal of Drug Targeting*, vol. 12, No. 9-10, pp. 623-633 (Dec. 2004).

Stepkowski, Stanislaw M., Molecular Targets for Existing and Novel Immunosuppressive Drugs, *Expert Reviews in Molecular Medicine*, vol. 2, No. 4, pp. 1-23 (Jun. 21, 2000).

Torchilin, V.P., Micellar Nanocarriers: Pharmaceutical Perspectives, *Pharmaceutical Research*, vol. 24, No. 1, pp. 1-16 (Jan. 2007).

Borchard et al., "The Potential of Muco-Adhesive Polymers in Enhancing Intestinal Peptide Drug Absorption. III: Effects of Chitosan-Glutamate and Carbomer on Epithelial Tight Junctions In Vitro," *Journal of Controlled Release*, 39(2-3), pp. 131-138 (May 1996).

Burglassi et al., "Development and In Vitro/In Vivo Testing of Mucoadhesive Buccal Patches Releasing Benzydamine and Lidocaine," *International Journal of Pharmaceuticals*, 133(1-2), pp. 1-7 (May 14, 1996).

Fuongfuchat et al., "Rheological Studies of the Interaction of Mucins with Alginate and Polyacrylate," *Carbohydrate Research*, 284(1), pp. 85-99 (Apr. 18, 1996).

Rambali et al., "Influence of the Roll Compactor Parameter Settings and the Compression Pressure on the Buccal Bio-Adhesive Tablet Properties," *International Journal of Pharmaceuticals*, 220(1), pp. 129-140 (Jun. 4, 2001).

Weyenberg et al., "Characterization and In Vivo Evaluation of Ocular Minitablets Prepared with Different Bioadhesive Carbopol-Starch Components," *European Journal of Pharmaceutics and Biopharmaceutics*, 62(2), pp. 202-209 (Feb. 2006).

Pal Kaur and Smitha: *Penetration Enhancers and Ocular Bioadhesives: Two New Avenues for Ophthalmic Drug Delivery*, Drug Development and Industrial Pharmacy, 28(4), 353-369 (2002).

Lukyanov and Torchilin: *Micelles from lipid derivatives of water-soluble polymers as delivery systems for poorly doluble drugs*, Advanced Drug Delivery Reviews 56, 1273-1289, 2004.

International Search Report based on PCT/US08/79170 dated Dec. 31, 2008.

Langevin, "Micelles and Microemulsions," *Annual Review of Physical Chemistry*, 43, pp. 341-369 (Oct. 1992).

Swei and Talbot, "Viscosity Correlation for Aqueous Polyvinylpyrrolidone (PVP) Solutions," *Journal of Applied Polymer Science*, 90(4), pp. 1153-1155 (Aug. 26, 2003).

Mitra, "Role of Transporters in Ocular Drug Delivery System", *Pharmaceutical Research*, vol. 26, No. 5, 17, pp. 1192-1196, Mar. 2009.

Janoria et al., "Novel approaches to retinal drug delivery", *Expert Opinion on Drug Delivery, Informa Healthcare*, GB, vol. 4, pp. 371-388, Jul. 2007.

Extended European Search Report in EP Serial No. 10786539.6 mailed Nov. 9, 2012.

Hu, X. et al., Biodegradable Amphiphilic Polymer-Drug Conjugate Micelles, *Expert Opin. Drug Deliv.*, vol. 6, No. 10, pp. 1079-1090, Oct. 2009.

Langevin, D., "Micelles and Microemulsions," *Annual Review of Physical Chemistry*, 43, pp. 341-369, Oct. 1992.

Swei and Talbot, "Viscosity Correlation for Aqueous Polyvinylpyrrolidone (PVP) Solutions," *Journal of Applied Polymer Science*, 90(4), pp. 1153-1155, Aug. 26, 2003.

Gregory et al., Compared with Cyclosporine, ISA247 Significantly Prolongs Renal-Allograft Survival in a Nonhuman Primate Model, *Transplantation*, vol. 78, No. 5, pp. 681-685, 2004.

Lallemand et al., Cyclosporine A Delivery to the Eye: A Pharmaceutical Challenge, *European Journal of Pharmaceutics and Biopharmaceutics*, vol. 56, pp. 307-318, 2003.

Lee et al., Pharmacokinetics and Organ Distribution of Cyclosporin A incorporated in Liposomes and Mixed Micelle, *International Journal of Pharmaceutics*, 191, pp. 87-93, 1999.

Maeng et al., Organozirconium Chemistry on Cyclosporin: A Novel Process for the Highly Stereoselective Synthesis of (*E*)-ISA247 (Voclosporin) and Close Analogues, *Synthesis* vol. 44, pp. 63-68, 2012 (Advanced Online Publication: Nov. 22, 2011).

Winfield, Opthalmic Products, *Pharmaceutical Practice*, Chapter 26, pp. 264-269, Churchill Livingstone, 2004.

Office Action in U.S. Appl. No. 12/774,600 mailed Sep. 24, 2012.

Office Action in U.S. Appl. No. 13/213,451 mailed Oct. 15, 2012.

* cited by examiner

OPHTHALMIC COMPOSITIONS COMPRISING CALCINEURIN INHIBITORS OR MTOR INHIBITORS

RELATED APPLICATIONS

This application claims the benefit of and priority to U.S. Provisional Application Ser. No. 60/997,796, filed Oct. 8, 2007, U.S. Provisional Application Ser. No. 60/992,205, filed Dec. 4, 2007, U.S. Provisional Application Ser. No. 61/038,223, filed Mar. 20, 2008, and U.S. Provisional Application Ser. No. 61/099,420, filed Sep. 23, 2008, the entirety of these applications are hereby incorporated herein by reference.

FIELD

The embodiments disclosed herein relate to stable ophthalmic compositions comprising calcineurin inhibitors or mTOR inhibitors, and more particularly to methods for treating an ocular disease and/or condition using the disclosed compositions.

BACKGROUND

Disease and injury to the anterior surface of the eye are the leading causes of visits to physicians for medical eye care in the United States. These diseases and injuries rank among the most painful of eye conditions and can lead to disability and blindness. Major clinical problems of the surface of the eye include ocular surface drying, tear film abnormalities, and related complications; ocular surface wounds with resultant pathology and scarring; corneal dysfunction dystrophies and inherited disease; inflammatory disease; and external ocular infections. Eye diseases and injuries can have symptoms ranging from itchy, runny eyes to impaired vision. Therefore, it is important to address eye problems right away, as some diseases can progressively worsen or even trigger other serious problems. Most pharmacologic management of ocular disease includes the topical application of solutions to the surface of the eye as drops. Despite the relatively small proportion of a topically applied drug dose that ultimately reaches anterior segment ocular tissues, topical formulations remain effective, largely because of the very high concentrations of drugs that are administered.

Disease and injury to tissues of the posterior segment of the eye, including the retina and choroid, is involved in many of the most common blinding diseases in the industrialized world. Age-related macular degeneration (AMD) alone impacts more than 10 million Americans. Severe vision loss from AMD and other diseases affecting the posterior segment, including diabetic retinopathy, glaucoma, and retinitis pigmentosa accounts for most cases of irreversible blindness world wide. Currently, the treatment of posterior segment disease is to a significant extent limited by the difficulty in delivering effective doses of drugs to target tissues in the posterior eye.

SUMMARY

Ophthalmic compositions comprising calcineurin inhibitors or mTOR inhibitors are disclosed herein. The ophthalmic compositions of the present disclosure are aqueous solutions of mixed micelles. The ophthalmic compositions disclosed herein are biocompatible, and are particularly useful for topical application to the eye for the treatment of an eye condition. According to aspects illustrated herein, there is provided a pharmaceutical composition that includes a calcineurin inhibitor or an mTOR inhibitor; a first surfactant with an HLB index greater than about 10; and a second surfactant with an HLB index of greater than about 13, wherein an absolute difference between the HLB index of the first surfactant and the HLB index of the second surfactant is greater than about 3, and wherein the composition forms mixed micelles.

According to aspects illustrated herein, there is provided a pharmaceutical composition that includes a calcineurin inhibitor; vitamin E TPGS; and octoxynol 40, wherein the composition is suitable for topical application to ocular tissue.

According to aspects illustrated herein, there is provided a pharmaceutical composition that includes an mTOR inhibitor; vitamin E TPGS; and octoxynol 40, wherein the composition is suitable for topical application to ocular tissue.

According to aspects illustrated herein, there is provided a method of preparing a mixed micelle composition that includes mixing a calcineurin inhibitor or a mTOR inhibitor with a first surfactant having an HLB index greater than about 10 and a second surfactant having an HLB index of greater than about 13 in a solvent to form a solvent solution; evaporating the solvent solution to form a near-solid matter; hydrating the near-solid matter with an aqueous solution; and dissolving the near-solid mixture to produce the mixed micelle composition, wherein the composition is optically clear.

According to aspects illustrated herein, there is provided a method for treating an ocular disease in a patient in need thereof that includes administering topically to an eye of the patient a composition comprising a therapeutically effective amount of a calcineurin inhibitor or mTOR inhibitor, the composition further having vitamin E TPGS and octoxynol-40, wherein the composition is an aqueous solution of mixed micelles.

According to aspects illustrated herein, there is provided a method for treating, reducing, ameliorating, or alleviating an inflammatory ocular disease in an animal that includes providing a mixed micellar pharmaceutical composition having a calcineurin inhibitor or an mTOR inhibitor encapsulated in micelles, the micelles formed with a first surfactant with an HLB index greater than about 10 and a second surfactant with an HLB index of greater than about 13; and administering to the animal an amount of the pharmaceutical composition at a frequency sufficient to treat, reduce, ameliorate, or alleviate the inflammatory ocular disease.

According to aspects illustrated herein, there is provided a method for treating, reducing, ameliorating, or alleviating a back-of-the-eye condition or disorder in a subject that includes providing a mixed micellar pharmaceutical composition having a calcineurin inhibitor encapsulated in micelles formed with a first surfactant with an HLB index greater than about 10 and a second surfactant with an HLB index of greater than about 13; and administering to the subject an amount of the pharmaceutical composition at a frequency sufficient to treat, reduce, ameliorate, or alleviate the back-of-the-eye condition or disorder.

According to aspects illustrated herein, there is provided an artificial tear composition that includes an aqueous solution of mixed micelles, the mixed micelles formed from a vitamin E tocopherol polyethylene glycol succinate (TPGS) derivative and an ethoxylated octylphenol surfactant.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 3A shows the mean ocular tissue concentration of voclosporin in the cornea. FIG. 3B shows the mean ocular tissue concentration of voclosporin in the iris/ciliary body. FIG. 3C shows the mean ocular tissue concentration of voclosporin in the lacrimal gland. FIG. 3D shows the mean ocular tissue concentration of voclosporin in the lens.

FIG. 4A shows the mean ocular tissue concentration of voclosporin in the lower conjunctiva. FIG. 4B shows the mean ocular tissue concentration of voclosporin in the lower eyelid. FIG. 4C shows the mean ocular tissue concentration of voclosporin in the nictitating membrane. FIG. 4D shows the mean ocular tissue concentration of voclosporin in the sclera.

FIG. 5A shows the mean ocular tissue concentration of voclosporin in the upper conjunctiva. FIG. 5B shows the mean ocular tissue concentration of voclosporin in the upper eyelid. FIG. 5C shows the mean ocular fluid concentration of voclosporin in the aqueous humor. FIG. 5D shows the mean ocular fluid concentration of voclosporin in the vitreous humor.

FIG. 6A shows the mean ocular fluid concentration of voclosporin in tears. FIG. 6B shows the mean ocular tissue concentration of voclosporin in the submandibular lymph node. FIG. 6C shows the mean ocular tissue concentration of voclosporin in the optic nerve. FIG. 6D shows the mean ocular tissue concentration of voclosporin in the choroid/retina.

Figure 1:
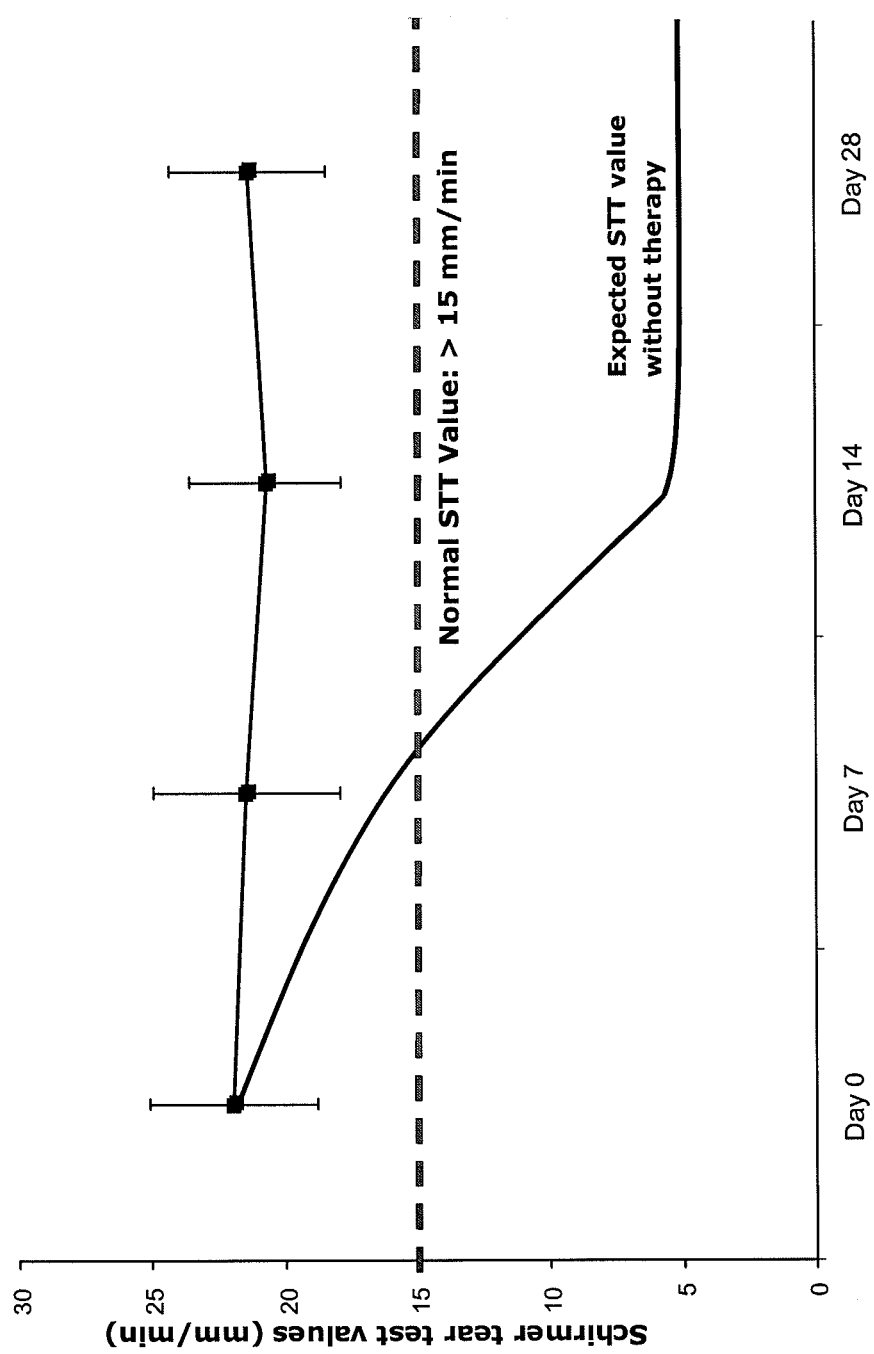
FIG. 1 shows a graphical representation of Mean Schirmer Tear Test (STT) values of canine KCS patients through 30 days of treatment with an embodiment of a mixed micellar formulation containing 0.2% voclosporin of the present disclosure.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The presently disclosed embodiments are directed towards pharmaceutical compositions comprising calcineurin inhibitors or mTOR inhibitors in a mixed micellar topical dosage form. The pharmaceutical compositions of the present disclosure have been found to treat, reduce, ameliorate and alleviate ocular conditions in a patient or subject. In an embodiment, the compositions can be used for the treatment of ocular diseases, including inflammatory ocular surface diseases. Examples of such diseases include, but are not limited to, dry eye syndrome (DES), Sjogren's syndrome, uveitis, conjunctivitis (pink eye), keratitis, keratoconjunctivitis, vernal keratoconjunctivitis (VKC), atopic keratoconjunctivitis (AKC), autoimmune disorders of the ocular surface, such as cicatrizing conjunctivitis, blepharitis, and scleritis.

In an embodiment, the compositions can be used for the treatment of a back-of-the eye condition and/or disorder. Examples of such conditions/disorders include, but are not limited to, posterior uveitis, age-related macular degeneration (AMD, wet and dry), diabetic eye conditions such as diabetic retinopathy (DR) and diabetic macular edema (DME), glaucoma, ocular hypertension, post-operative eye pain and inflammation, ocular neovascularization such as posterior segment neovascularization (PSNV), proliferative vitreoretinopathy (PVR), cytomegalovirus (CMV) retinitis, choroidal neovascular membranes (CNVM), vascular occlusive diseases, retinitis pigmentosa, optic neuritis, cicatrizing ocular surface diseases, ocular infections, inflammatory ocular diseases, ocular surface diseases, corneal diseases, retinal diseases such as epiretinal membrane, ocular manifestations of systemic diseases, hereditary eye conditions, and ocular tumors.

In an embodiment, the compositions can be used for preventing transplant rejection of, for example, corneal allografts following transplantation. It is well known that in inflammation T-lymphocytes play a critical role in mediating rejection of foreign tissues. Prevention of rejection is of paramount importance in maintaining the health of transplanted corneas. Rejection may occur in any of the layers comprising the cornea, for example, the corneal epithelium, the corneal stroma or the corneal endothelium. The functioning of the cornea can be compromised following endothelial rejection. The endothelial layer serves to maintain the cornea in a compact state, acting as a pump by removing water from the corneal stroma. If the function of the endothelial layer is compromised, disorientation of collagen fibers can ensue, and transparency of the cornea can be lost. Human endothelial cells are non-replicative, and as a consequence, donor cell loss in the setting of rejection is irreversible and may lead to diminished graft function and survival. Thus, the goal of either prevention or treatment of rejection in corneal transplant recipients is to minimize endothelial cell loss. The compositions of the present disclosure can be used for the prevention of rejection following corneal allograft transplantation.

A patient or subject to be treated by any of the compositions or methods of the present disclosure can mean either a human or a non-human animal. In an embodiment, the present disclosure provides methods for the treatment of an ocular disease in a human patient in need thereof. In an embodiment, the present disclosure provides methods for the treatment of an inflammatory ocular disease in a human patient in need thereof. In another embodiment, the present disclosure provides methods for the treatment of an ocular disease in a veterinary patient in need thereof, including, but not limited to dogs, horses, cats, rabbits, gerbils, hamsters, rodents, birds, aquatic mammals, cattle, pigs, camelids, and other zoological animals.

As used herein, the terms "ocular disease," "ocular condition," "eye disease," and "eye condition" refer to diseases/conditions of the eye(s) that can be sight threatening, lead to eye discomfort, and may signal systemic health problems.

As used herein, the term "anterior segment disease" refers to all disorders that affect the eye surface, anterior chamber, iris and ciliary body and lens of the eye. The eye surface is composed of the cornea, conjunctiva, eyelids, lacrimal and meibomian glands, and the interconnecting nerves.

As used herein, the terms "posterior segment eye disease" and "back-of-the-eye disease" refer to all disorders that affect the posterior segment of the eye. A posterior eye disease is a disease which primarily affects a posterior ocular site such as choroid or sclera, vitreous, vitreous chamber, retina, optic nerve, and blood vessels and nerves which vascularize or innervate a posterior ocular site.

As used herein, the terms "biocompatible" and "nonirritating" refer to the property of being biologically compatible by not producing a toxic, injurious or immunological response in living tissue. The compositions of the present disclosure are biocompatible. Similarly, none of the components of the compositions of the present disclosure are inherently irritating to ocular tissues.

As used herein, the term "emulsion" refers to a mixture of two or more immiscible liquids, where one liquid is dispersed in another. An emulsion, for example, an intimate mixture of oil and water, is generally of a cloudy or milky appearance.

As used herein, the term "micelle" refers to an aggregate (or cluster) of surfactant molecules. Micelles only form when the concentration of surfactant is greater than the critical micelle concentration (CMC). Surfactants are chemicals that are amphipathic, which means that they contain both hydrophobic and hydrophilic groups. Micelles can exist in different shapes, including spherical, cylindrical, and discoidal. A micelle comprising at least two different molecular species is a mixed micelle. The ophthalmic compositions of the present disclosure include an aqueous, clear, mixed micellar solution.

Polymeric micelles are exploited as pharmaceutical nanocarriers for the delivery of poorly water-soluble (i.e., water-insoluble) or hydrophobic drugs, which can be solubilized in the hydrophobic inner core of a micelle. Micelles can therefore serve to improve solubility and bioavailability of various hydrophobic drugs. The small size of micelles (typically about 10 to about 100 nm) allows for efficient accumulation of an associated active moiety into targeted tissues. Also, the small size of micelles allows the advantage of sterilization of micelles by filtration through membranes with the cut off size 0.22 μm. Micelles can be formed from one or more polymeric nonionic surfactants. Since the micelle size is smaller than visible light wavelengths, it is believed that the light is not scattered by the small micelles resulting in a transparent, clear solution.

As used herein, the term "optical clarity" refers to 90% or greater transmission of light of 400 nm wavelength in a 1.0 centimeter path. The clarity of the solution results from the micelle size which is typically smaller than the smallest wavelength of a visible light radiation (about 350 nm). In an embodiment, the ophthalmic compositions of the present disclosure are substantially clear with an absorption in general, below 0.1; preferably with absorption, below 0.05 measured at 400 nm.

The HLB (hydrophilic/lipophilic balance) index value is a concept introduced by Griffin in 1950 as a measure of the hydrophilicity or lipophilicity of nonionic surfactants. It can be determined experimentally by the phenol titration method of Marszall; see "Parfumerie, Kosmetik", Vol. 60, 1979, pp. 444-448; further literature references can be found in Rompp, Chemistry Lexicon, 8th Edition 1983, p. 1750. See also, for example, U.S. Pat. No. 4,795,643 (Seth).

Dry eye syndrome (DES, Chronic dry eye, Keratitis sicca; Xerophthalmia; Keratoconjunctivitis sicca) can be defined as a condition that includes a variety of disorders that result in a loss of, or altered composition of, the natural tear film, which maintains the surface of the eye. Without this tear film, vision is impaired and patients may suffer severe ocular discomfort. DES can be caused by excessive tear evaporation or by a reduction of tear production in the lacrimal gland, which is the site of tear production. Though the exact causes of this condition are unknown, there is evidence supporting the link between reduced tear production and lacrimal gland inflammation. Currently available medications for DES are leaving substantial room for more effective and better tolerated products.

DES may also be a symptom of Sjogren's syndrome which is an autoimmune disorder in which the glands that produce tears and saliva are destroyed. This leads to dry mouth, decreased tearing, and other dry mucous membranes.

Uveitis is an inflammation inside the eye affecting the uvea. The uvea is the layer of the eye between the sclera and the retina, and includes the iris, ciliary body and the choroid. The uvea supplies most of the blood supply to the retina. Uveitis can be considered an autoimmune disease resulting in chronic inflammation of the eye. There is substantial evidence indicating the involvement of T-lymphocytes, key cells involved in inflammatory processes, in the development of uveitis. The inflammation can cause areas of scarring on the choroid and retina that cause areas of vision loss. There are various forms of uveitis including anterior uveitis, pars planitis, and posterior uveitis. Serious complications may occur if uveitis is left untreated; including cataracts, glaucoma, retinal detachment, retinal edema and permanent vision loss.

Anterior uveitis (iritis) occurs in the front of the eye and is the most common form of uveitis. Par planitis is an inflammation of the pars plana, a narrow area between the iris and the choroid. This condition occurs more frequently in young men, but is usually not associated with another disease. Posterior uveitis (chondroitis) affects primarily the choroid; the back portion of the uveal tract. If the retina is also involved, it is called chorioretinitis. Posterior uveitis may occur in association with an autoimmune disease, or follow a systemic infection. In posterior uveitis, inflammation can last from months to years and may cause permanent vision damage, even with treatment.

Uveitis can cause vision impairment, ocular pain, and loss of vision. It is estimated that about 10% of new cases of blindness in the U.S. are caused by uveitis. Approximately 300,000 people suffer from uveitis in the U.S. alone, the majority of whom are affected by anterior uveitis. The only therapeutic class approved by the FDA for treatment of uveitis is corticosteroids, which are noted for multiple side effects, such as hypertension, hyperglycemia, and hypercholesterolemia, and in the eye, glaucoma and cataract formation.

Conjunctivitis (pink eye) describes a group of diseases that cause swelling, itching, burning, and redness of the conjunctiva, the protective membrane that lines the eyelids and covers exposed areas of the sclera, or white of the eye.

Keratitis is an inflammation of the cornea (clear portion in the front of the eye). Keratitis can be caused by an infection (bacterial, fungal, viral, parasite, etc.) or a non-infectious agent (e.g., certain types of auto-immune diseases are associated with a variety of non-infectious keratitises).

Keratoconjunctivitis refers to an inflammation of the cornea and conjunctiva.

Vernal keratoconjunctivitis (VKC) is a recurrent ocular inflammatory disease characterized by hard, elevated, cobblestone like bumps on the upper eyelid. There may also be swellings and thickening of the conjunctiva. The conjunctiva is the outermost membrane which lines the eyelids as well as the exposed parts of the eye, except for the cornea.

Atopic keratoconjunctivitis is the result of a condition called atopy. Atopy is a genetic condition whereby the immune system produces higher than normal antibodies in response to a given allergen.

Systemic immune mediated diseases such as cicatrizing conjunctivitis and other autoimmune disorders of the ocular surface represent a clinically heterogeneous group of conditions where acute and chronic autoreactive mechanisms can cause significant damage to the eye. When severe and affecting the epithelium and substantia propria of the conjunctiva, cicatrization can ensue, leading to significant mechanical alterations as a result of the fibrosis. These conditions, though generally infrequent, can be the cause of profound pathology and visual disability.

Blepharitis is a common condition that causes inflammation of the eyelids.

Scleritis is a serious inflammatory disease that affects the white outer coating of the eye, known as the sclera.

Calcineurin is a calcium/calmodulin-regulated protein phosphatase involved in intracellular signaling. Calcineurin inhibitors are substances which block calcineurin dephosphorylation of appropriate substrates, by targeting calcineurin phosphatase (PP2B, PP3), a cellular enzyme that is involved in gene regulation. Another class of compounds that exhibit this general therapeutic profile are the mTOR inhibitors. mTOR inhibitors target a molecular target known as "mammalian target of rapamycin" (mTOR). A prototypical compound of this class is sirolimus.

Age-related macular degeneration (AMD) is a disease associated with aging that gradually destroys sharp, central vision. AMD affects the macula, which is located at the center of the retina. AMD occurs in two forms: wet and dry. Wet AMD occurs when abnormal blood vessels behind the retina start to grow under the macula. These new blood vessels tend to be very fragile and often leak blood and fluid. The blood and fluid raise the macula from its normal place at the back of the eye. Damage to the macula occurs rapidly. Dry AMD occurs when the light-sensitive cells in the macula slowly break down, gradually blurring central vision in the affected eye.

Diabetes can affect the eye in a number of ways. Diabetic retinopathy (DR) is a complication of diabetes that results from damage to the blood vessels of the light-sensitive tissue at the back of the eye (the retina). At first, diabetic retinopathy may cause no symptoms or only mild vision problems. Eventually, however, diabetic retinopathy can result in blindness.

Diabetic macular edema (DME) is the swelling of the retina in diabetes mellitus due to leaking of fluid from blood vessels within the macula.

Ocular neovascularization is the abnormal or excessive formation of blood vessels in the eye. Ocular neovascularization has been shown in diabetic retinopathy and age-related macular degeneration (ARMD).

Proliferative vitreoretinopathy (PVR) is scar tissue formation within the eye. "Proliferative" because cells proliferate and "vitreoretinopathy" because the problems involve the vitreous and retina. In PVR scar tissue forms in sheets on the retina which contract. This marked contraction pulls the retina toward the center of the eye and detaches and distorts the retina severely. PVR can occur both posteriorly and anteriorly with folding of the retina both anteriorly and circumferentially.

The cytomegalovirus (CMV) is related to the herpes virus and is present in almost everyone. When a person's immune system is suppressed because of disease (HIV), organ or bone marrow transplant, or chemotherapy, the CMV virus can cause damage and disease to the eye and the rest of the body. CMV affects the eye in about 30% of the cases by causing damage to the retina. This is called CMV retinitis.

Optic neuritis occurs when the optic nerve becomes inflamed and the myelin sheath becomes damaged or is destroyed. Nerve damage that occurs in the section of the optic nerve located behind the eye, is called retrobulbar neuritis, which is another term sometimes used for optic neuritis.

Also known as macular pucker, epiretinal membrane is a scar-tissue like membrane that forms over the macula. It typically progresses slowly and affects central vision by causing blurring and distortion. As it progresses, the pulling of the membrane on the macula may cause swelling.

A calcineurin inhibitor of the present disclosure is preferably an immunophilin-binding compound having calcineurin inhibitory activity. Immunophilin-binding calcineurin inhibitors are compounds forming calcineurin inhibiting complexes with immunophilins, e.g. cyclophilin and macrophilin. Examples of cyclophilin-binding calcineurin inhibitors are cyclosporines or cyclosporine derivatives (hereinafter cyclosporines) and examples of macrophilin-binding calcineurin inhibitors are ascomycin (FR 520) and ascomycin derivatives (hereinafter ascomycins). A wide range of ascomycin derivatives are known, which are either naturally occurring among fungal species or are obtainable by manipulation of fermentation procedures or by chemical derivatization. Ascomycin-type macrolides include ascomycin, tacrolimus (FK506), sirolimus and pimecrolimus.

Cyclosporine, originally extracted from the soil fungus *Potypaciadium infilatum*, has a cyclic 11-amino acid structure and includes e.g. Cyclosporines A through I, such as Cyclosporine A, B, C, D and G. Cyclosporine binds to the cytosolic protein cyclophilin of immunocompetent lymphocytes, especially T-lymphocytes, forming a complex. The complex inhibits calcineurin, which under normal circumstances induces the transcription of interleukin-2 (IL-2). Cyclosporine also inhibits lymphokine production and interleukin release, leading to a reduced function of effector T-cells.

Voclosporin is a next-generation calcineurin inhibitor that is a more potent and less toxic semi-synthetic derivative of cyclosporine A. Like other molecules of this class, voclosporin reversibly inhibits immunocompetent lymphocytes, particularly T-lymphocytes, and also inhibits lymphokine production and release. This action is primarily mediated through inhibition of calcineurin, a phosphatase enzyme found in the cytoplasm of cells. Voclosporin has a single carbon extension with double bond that has been shown to extend deeper into the latch/regulatory region of calcineurin. In an embodiment, the compositions of the present disclosure comprise the trans-version of voclosporin, trans-ISA247 CAS RN 368455-04-3 which is described in, for example, US Patent Publication No.: 2006/0217309, which is hereby incorporated herein by reference. Further compositions of voclosporin are described, for example, in U.S. Pat. No. 7,060,672, which is hereby incorporated herein by reference.

Tacrolimus (FK506) is another calcineurin inhibitor which is also a fungal product, but has a macrolide lactone structure. Tacrolimus has been used as an immunosuppressant in conjunction with liver, kidney, heart, lung and heart/lung transplants. Tacrolimus has also been shown to inhibit the production of IL-2. Tacrolimus binds to an immunophilin (FK-binding protein 12, FKBP12), followed by binding of the complex to calcineurin to inhibit its phosphatase activity.

Sirolimus (rapamycin) is a microbial product isolated from the actinomycete *Streptomyces hygroscopicus*. Sirolimus binds to an immunophilin (FK-binding protein 12, FKBP12) forming a complex, which inhibits the mammalian target of rapamycin (mTOR) pathway through directly binding the mTOR Complex1 (mTORC1). Sirolimus inhibits the response to interleukin-2 (IL-2) and thereby blocks activation of T- and B-cells. By contrast, tacrolimus and cyclosporine inhibit the production of IL-2.

Pimecrolimus is a new calcineurin inhibitor which has been found to have antifungal properties against *Malassezia* spp., as does tacrolimus.

Calcineurin inhibitors such as cyclosporine A, voclosporin, ascomycin, tacrolimus, pimecrolimus, an analog thereof, or a pharmaceutically acceptable salt thereof, can be utilized in a mixed micellar composition of the present disclosure. In an embodiment, the calcineurin inhibitor is voclosporin.

mTOR inhibitors such as sirolimus (rapamycin), temsirolimus, everolimus, an analog thereof, or a pharmaceutically acceptable salt thereof, can be utilized in a mixed micellar composition of the present disclosure.

The present disclosure provides pharmaceutical compositions that include a calcineurin inhibitor or an mTOR inhibitor, a first surfactant with an HLB index greater than about 10, and a second surfactant with an HLB index of greater than about 13, wherein the pharmaceutical composition forms mixed micelles. Typically, the mixed micelles are provided in an aqueous solution such that topical application of the compositions is achieved. In an embodiment, an absolute difference between the HLB index of the first surfactant and the HLB index of the second surfactant is greater than about 3. The compositions can be used in topical application to the eye to treat a variety of ocular conditions, including both anterior segment and posterior segment conditions.

In an embodiment, a pharmaceutical composition of the present disclosure comprises cyclosporine A, a first surfactant with an HLB index greater than about 10, and a second surfactant with an HLB index of greater than about 13. In an embodiment, the composition comprises cyclosporine A, vitamin E TPGS and octoxynol-40. In an embodiment, a mixed micellar composition of the present disclosure comprises voclosporin, a first surfactant with an HLB index greater than about 10, and a second surfactant with an HLB index of greater than about 13. In an embodiment, the composition comprises voclosporin, vitamin E TPGS and octoxynol-40. In an embodiment, a mixed micellar composition of the present disclosure comprises tacrolimus, a first surfactant with an HLB index greater than about 10, and a second surfactant with an HLB index of greater than about 13. In an embodiment, the composition comprises tacrolimus, vitamin E TPGS and octoxynol-40. In an embodiment, a mixed micellar composition of the present disclosure comprises an mTOR inhibitor, a first surfactant with an HLB index greater than about 10, and a second surfactant with an HLB index of greater than about 13. In an embodiment, the mTOR inhibitor is selected from one of sirolimus, temsirolimus, everolimus, an analog thereof, or a pharmaceutically acceptable salt thereof. In an embodiment, the composition comprised sirolimus, vitamin E TPGS and octoxynol-40. In another embodiment, a mixed micellar composition of the present disclosure comprises pimecrolimus, a first surfactant with an HLB index greater than about 10, and a second surfactant with an HLB index of greater than about 13. In an embodiment, the composition comprises pimecrolimus, vitamin E TPGS and octoxynol-40 is disclosed.

In an embodiment of the present disclosure, two surfactants are used to generate a mixed micellar formulation of voclosporin, resulting in an increase in voclosporin's aqueous solubility and bioavailability. In an embodiment, the mixed micellar structure includes a first surfactant with an HLB index greater than about 10, and a second surfactant with an HLB index of greater than about 13. In an embodiment, an absolute difference between the HLB index of the first surfactant and the HLB index of the second surfactant is greater than about 3.

In an embodiment, the first surfactant having an HLB greater than about 10 is selected from various chemical derivatives of vitamin E with ester and ether linkages of various chemical moieties to polyethylene glycol of various lengths. Particularly preferred are vitamin E tocopherol polyethylene glycol succinate (TPGS) derivatives with PEG molecular weights between about 500 and 6000 Da. In a preferred embodiment, the vitamin E polymeric derivative with an HLB index greater than about 10 is vitamin E tocopherol polyethylene glycol 1000 succinate (Vitamin E TPGS, tocopherlosan). In an embodiment, the vitamin E TPGS is present in the composition from about 0.01 wt % to about 20 wt %/volume. In an embodiment, the vitamin E TPGS is present in the composition from about 0.1 wt % to about 10 wt %/volume. It should be understood that throughout the specification the term weight percent (wt %) refers to mass per unit volume, unless otherwise specified.

Vitamin E Tocopherol Polyethylene Glycol 1000 Succinate (Vitamin E TPGS) is an amphipathic excipient which is a water soluble derivative of natural-source vitamin E. Vitamin E TPGS, or PEGylated vitamin E, is a vitamin E derivative in which polyethylene glycol subunits are attached by a succinic acid diester at the ring hydroxyl of the vitamin E molecule. Vitamin E TPGS is a hydrophilic non-ionic surfactant with an HLB index of about 13. Various chemical derivatives of vitamin E TPGS including ester and ether linkages of various chemical moieties are included within the definition of vitamin E TPGS. In addition to serving as a source of water-soluble vitamin E, vitamin E TPGS has been suggested for use as an emulsifier, solubilizer, absorption enhancer, and a vehicle for lipid-soluble drug delivery formulations.

In an embodiment, the second surfactant has a HLB greater than 13 is a hydrophilic polyethylene glycol (PEG)-alkyl ether surfactant or polyethylene glycol (PEG)-alkyl aryl ether surfactant. In an embodiment, this surfactant is selected from a PEG 5-100 octyl phenyl ether which has an HLB greater than about 13. The PEG octylphenyl compound is selected from the group consisting of octoxynol-9, octoxynol-10, octoxynol-11, octoxynol-12, octoxynol-13, octoxynol-16, octoxynol-20, octoxynol-25, octoxynol-30, octoxynol-33, octoxynol-40, and octoxynol-70. In an embodiment, the PEG-alkyl phenyl ether surfactant is octoxynol-40. In an embodiment, the surfactant with an HLB greater than about 10 is selected from a PEG-5-100 nonyl phenyl ether; tyloxapol (ethoxylated p-tert-octylphenol formaldehyde polymer), a PEG-fatty acid monoester surfactant, a PEG-glycerol fatty acid ester, and a PEG-sorbiton fatty acid ester. PEG-Fatty acid monoester surfactants include, but are not limited to, PEG-15 oleate, PEG-20 laurate, PEG-20 oleate, PEG-20 stearate, PEG-32 laurate, PEG-32 oleate, PEG-32 stearate, PEG-40 laurate, PEG-40 oleate, and PEG-40 stearate. PEG-Glycerol fatty acid esters include, but are not limited to, PEG-15 glyceryl laurate PEG-20 glyceryl laurate, PEG-30 glyceryl laurate, PEG-40 glyceryl laurate, and PEG-20 glyceryl stearate. PEG-sorbiton fatty acid esters include, but are not limited to, PEG-4 sorbiton monolaurate, PEG-4 sorbiton monostearate, PEG-5 sorbiton monooleate, PEG-20 sorbiton monolaurate, PEG-20 sorbiton monopalmitate, PEG-20 sorbiton monostearate, and PEG-20 sorbiton monooleate. In an embodiment, the second surfactant with HLB greater than about 13 is octoxynol-40. Octoxynol-40 (IGEPAL CA-897) has an HLB index of about 18. In an embodiment, the octoxynol-40 is present in the composition from about 0.001 wt % to about 10 wt %/volume. In an embodiment, the octoxynol-40 is present in from about 0.01 wt % to about 5.0 wt %/volume.

Calcineurin inhibitors and mTOR inhibitors which can be formulated according to the present disclosure include, but are not limited to, cyclosporine A, voclosporin (LX211), ascomycin, tacrolimus (FK506), sirolimus, everolimus, and pimecrolimus, including their analogs, pharmaceutically acceptable salts, esters, and prodrugs. Further contemplated are mixtures of a calcineurin or an mTOR inhibitor with one or more drugs, vitamins, and diagnostic agents. A preservative may or may not be used to preserve the formulations. In an embodiment, a mixture of defined amounts of octoxynol-40 forms mixed micelles with vitamin E TPGS, creating stability and solubility for a water-insoluble drug that fills the inner core of the mixed micelle. In an embodiment, the mixed micellar composition comprises a calcineurin inhibitor, vitamin E TPGS and octoxynol-40. The mixed micellar formulation is a clear, homogenous aqueous solution of the calcineurin inhibitor or mTOR inhibitor. In an embodiment, the Vitamin E TPGS contributes to the solubilization of the calcineurin inhibitor or mTOR inhibitor and may reduce ocular discomfort in aqueous conditions. In an embodiment, the octoxynol-40 contributes to the reduction of ocular discomfort, and to the formation of a stable, mixed micellar formulation that is optically clear.

In the compositions of the presently disclosed embodiments, the calcineurin inhibitor or mTOR inhibitor is present at concentrations ranging from about 0.01 weight percent (wt %) to about 10 wt %, from about 0.1 to about 3.0 wt %. In an embodiment, the compositions of the present disclosure comprise voclosporin at about 0.2 to about 0.5 wt %, as illustrated in the examples. In an embodiment, the Vitamin E TPGS concentration is from about 0.01 to about 20 wt %, from about 0.1 to about 5 wt %. Octoxynol-40 or its homolog mixtures are present at concentrations from about 0.001 to about 10 wt %, from about 0.01 to about 3.0 wt %. In an embodiment, the total amount of surfactants in the compositions of the present disclosure is 30 percent or less of the total composition with the remaining major component being water.

In an embodiment, a composition of the present disclosure comprises about 0.2 wt % of voclosporin, about 2.5 wt % of vitamin E TPGS, and about 2.0 wt % octoxynol-40. In an embodiment. a composition of the present disclosure comprises about 0.5 wt % of voclosporin, about 3.5 wt % of vitamin E TPGS, and about 2.0 wt % octoxynol-40. In another embodiment, a composition of the present disclosure comprises about 2.0 wt % voclosporin.

Site-specific delivery to the back-of-the-eye, including the choroid, and particularly the retina, is one of the challenges facing researchers in the field of therapeutic ophthalmology. There is growing but unmet need for drug carriers that reach the retina at appropriate therapeutic levels following topical administration. As will be shown in the Examples that follow, it has been found that after topical administration of a composition of the presently disclosed embodiments, the calcineurin inhibitor or mTOR inhibitor drug is able to reach the back of the eye, thus providing a treatment for back-of-the-eye ocular conditions.

The compositions of the present disclosure can be used as a topically applied drug delivery platform for delivery of a variety of hydrophobic, water-insoluble drugs, such as a calcineurin inhibitor or mTOR inhibitor to the back-of-the-eye for various back-of-the-eye conditions. Suitable classes of water-insoluble drugs include, but are not limited to, peptides, eicosanoids (e.g. prostacyclins and prostaglandins), anti-inflammatory drugs, autonomic drugs (e.g. beta-blockers, alpha-blockers, beta-agonists, and alpha-agonists), biologics, gene therapy agents (e.g. viral vectors), anti-infectives (e.g. antifungals, antibiotics, and antivirals), retinoids, RNAi, photo sensitizers, steroids (e.g., estrogens and derivatives thereof), mixture drugs, immuno-modulators, chemotherapeutic agents, G-coupled protein receptor antagonists, receptor tyrosine kinase (RTK) inhibitors, growth hormone inhibitors, integrin inhibitors, Sdfl/CXCR4 pathway inhibitors, and nACh receptor antagonists. Preferably, the water-insoluble drug is a calcineurin inhibitor or an mTOR inhibitor.

The compositions of the present disclosure can be used as a topically applied drug delivery platform for delivery of a corticosteroid to the back-of-the-eye to treat, for example, DME. Examples of corticosteroids include, but are not limited to, prednisolone, hydrocortisone, triamcinolone and budesonide.

The compositions of the present disclosure can be used as a topically applied drug delivery platform for delivery of a non-steroidal anti-inflammatory drug (NSAID) to the back-of-the-eye to treat, for example, DME. Examples of NSAIDs include, but are not limited to, Cox-2 inhibitors such as celecoxib, ruboxistaurin and nimesulide.

The compositions of the present disclosure can be used as a topically applied drug delivery platform for delivery of an anti-growth factor molecule to the back-of-the-eye to treat, for example, AMD. Examples of anti-growth factor molecules include, but are not limited to, vascular endothelial growth factor (VEGF) inhibitors such as, pegaptanib (macugen), ranibizumab (lucentis), and bevacizumab (avastin).

In an embodiment, a mixed micellar composition of the present disclosure having either a calcineurin inhibitor or mTOR inhibitor that fills the inner core of the mixed micelle, can be used in topical application to the eye in a method to treat a back-of-the-eye ocular condition. In an embodiment, calcineurin inhibitor or mTOR inhibitor is present in the composition at concentrations from about 0.01 weight percent (wt %) to about 10 wt %, preferably from about 0.1 wt % to about 3.0 wt %. In an embodiment, the calcineurin inhibitor or mTOR inhibitor is voclosporin, and the voclosporin is present in the composition at a concentration from about 0.2 wt % to about 0.5 wt %. In an embodiment, Vitamin E TPGS is present in the composition at concentrations from about 0.01 wt % to about 20 wt %, preferably from about 0.1 wt % to about 5 wt %. In an embodiment, Octoxynol-40 or its homolog mixtures are present in the composition at concentrations from about 0.001 wt % to about 10 wt %, preferably from about 0.01 wt % to about 3.0 wt %. Preferably, the total amount of surfactants in the compositions of the presently disclosed embodiments is about 30 percent or less of the total composition with the remaining major component being water.

In an embodiment, a mixed micellar composition of the presently disclosed embodiments comprises about 0.2 wt % of voclosporin, about 2.5 wt % of vitamin E TPGS, and about 2.0 wt % octoxynol-40. In an embodiment, a mixed micellar composition of the presently disclosed embodiments comprises about 0.5 wt % of voclosporin, about 3.5 wt % of vitamin E TPGS, and about 2.0 wt % octoxynol-40. In another embodiment, a mixed micellar composition of the presently disclosed embodiments comprises voclosporin at about 2.0 wt %.

At present, most ocular diseases are treated with the topical application of solutions administered as eye drops for water-soluble drugs and as ointments or aqueous suspensions for water-insoluble drugs. These dosage forms account for approximately 90% of currently marketed formulations. The cornea represents a primary pathway for ocular penetration of topically applied drugs. Drug absorption primarily takes place through the cornea and into the aqueous humor and diffuses to the posterior segment. Drug can diffuse into the iris root and subsequently into the posterior chamber aqueous humor and into the posterior tissues. Drug can enter directly through the pars plana without encountering the blood-retinal barrier. Drug can diffuse across the sclera by lateral diffusion followed by penetration of Bruch's membrane and the retinal pigment epithelium (RPE). To a lesser extent, drug can be absorbed into the systemic circulation either through the conjunctival vessels or via nasolacrimal duct and gain systemic access to the retinal vessels.

As shown in the Examples below, therapeutic levels of voclosporin were noticed 24-hours post-administration of a pharmaceutical composition of the present disclosure, indicating that once daily (QD) dosing with the aqueous mixed micellar compositions of the presently disclosed embodiments is possible. As shown in the Examples, voclosporin, given in the mixed micellar composition of the present disclosure, can be detected at high levels in the choriod/retina, while low levels of voclosporin are detected in the vitreous humor. The calcineurin inhibitor voclosporin is reaching the back of the eye when topically applied in the mixed micellar formulations described herein.

The compositions of the present disclosure may also contain other components such as, but not limited to, additives, adjuvants, buffers, tonicity agents, bioadhesive polymers, and preservatives. In any of the compositions of this disclosure for topical to the eye, the mixtures are preferably formulated at about pH 5 to about pH 8. This pH range may be achieved by the addition of buffers to the composition as described in the examples. In an embodiment, the pH range in the composition in a formulation is about pH 6.6 to about pH 7.0. It should be appreciated that the compositions of the present disclosure may be buffered by any common buffer system such as phosphate, borate, acetate, citrate, carbonate and borate-polyol complexes, with the pH and osmolality adjusted in accordance with well-known techniques to proper physiological values. The mixed micellar compositions of the present disclosure are stable in buffered aqueous solution. That is, there is no adverse interaction between the buffer and any other component that would cause the compositions to be unstable.

Tonicity agents include, for example, mannitol, sodium chloride, xylitol, etc. These tonicity agents may be used to adjust the osmolality of the compositions. In one aspect, the osmolality of the formulation is adjusted to be in the range of about 250 to about 350 mOsmol/kg. In a preferred aspect, the osmolality of the formulation is adjusted to between about 280 to about 300 mOsmol/kg.

An additive such as a sugar, a glycerol, and other sugar alcohols, can be included in the compositions of the present disclosure. Pharmaceutical additives can be added to increase the efficacy or potency of other ingredients in the composition. For example, a pharmaceutical additive can be added to a composition of the present disclosure to improve the stability of the calcineurin inhibitor or mTOR inhibitor, to adjust the osmolality of the composition, to adjust the viscosity of the composition, or for another reason, such as effecting drug delivery. Non-limiting examples of pharmaceutical additives of the present disclosure include sugars, such as, trehalose, mannose, D-galactose, and lactose. In an embodiment, the sugars can be incorporated into a composition prior to hydrating the thin film (i.e., internally). In another embodiment, the sugars can be incorporated into a composition during the hydration step (i.e., externally) (see Example 17). In an embodiment, an aqueous, clear, mixed micellar solution of the present disclosure includes additives such as sugars.

In an embodiment, compositions of the present disclosure further comprise one or more bioadhesive polymers. Bioadhesion refers to the ability of certain synthetic and biological macromolecules and hydrocolloids to adhere to biological tissues. Bioadhesion is a complex phenomenon, depending in part upon the properties of polymers, biological tissue, and the surrounding environment. Several factors have been found to contribute to a polymer's bioadhesive capacity: the presence of functional groups able to form hydrogen bridges (—OH, COOH), the presence and strength of anionic charges, sufficient elasticity for the polymeric chains to interpenetrate the mucous layer, and high molecular weight. Bioadhesion systems have been used in dentistry, orthopedics, ophthalmology, and in surgical applications. However, there has recently emerged significant interest in the use of bioadhesive materials in other areas such as soft tissue-based artificial replacements, and controlled release systems for local release of bioactive agents. Such applications include systems for release of drugs in the buccal or nasal cavity, and for intestinal or rectal administration.

In an embodiment, a composition of the present disclosure includes at least one bioadhesive polymer. The bioadhesive polymer can enhance the viscosity of the composition and thereby increase residence time in the eye. Bioadhesive polymers of the present disclosure include, for example, carboxylic polymers like Carbopol® (carbomers), Noveon® (polycarbophils), cellulose derivatives including alkyl and hydroxyalkyl cellulose like methylcellulose, hydroxypropylcellulose, carboxymethylcellulose, gums like locust beam, xanthan, agarose, karaya, guar, and other polymers including but not limited to polyvinyl alcohol, polyvinyl pyrollidone, polyethylene glycol, Pluronic® (Poloxamers), tragacanth, and hyaluronic acid; phase-transition polymers for providing sustained and controlled delivery of enclosed medicaments to the eye (e.g., alginic acid, carrageenans (e.g., Eucheuma), xanthan and locust bean gum mixtures, pectins, cellulose acetate phthalate, alkylhydroxyalkyl cellulose and derivatives thereof, hydroxyalkylated polyacrylic acids and derivatives thereof, poloxamers and their derivatives, etc. Physical characteristics in these polymers can be mediated by changes in environmental factors such as ionic strength, pH, or temperature alone or in combination with other factors. In an embodiment, the optional one or more bioadhesive polymers is present in the composition from about 0.01 wt % to about 10 wt %/volume, preferably from about 0.1 to about 5 wt %/volume. In an embodiment, the compositions of the present disclosure further comprise at least one hydrophilic polymer excipient selected from, for example, PVP-K-30, PVP-K-90, HPMC, HEC, and polycarbophil. In an embodiment, the polymer excipient is selected from PVP-K-90, PVP-K-30 or HPMC. In an embodiment, the polymer excipient is selected from PVP-K-90 or PVP-K-30.

In an embodiment, if a preservative is desired, the compositions may optionally be preserved with any well-known system such as benzyl alcohol with/without EDTA, benzalkonium chloride, chlorhexidine, Cosmocil® CQ, or Dowicil® 200.

The ophthalmic compositions can be administered topically to the eye as biocompatible, aqueous, clear mixed micellar solutions. The compositions have the drugs incorporated and/or encapsulated in micelles which are dispersed in an aqueous medium.

In an embodiment, the present disclosure provides a method of preparing a mixed micelle composition that includes mixing a calcineurin or mTOR inhibitor with a first surfactant having an HLB index greater than 10 in a solvent to form a solvent solution; evaporating the solvent solution to form a near-solid matter; hydrating the near-solid matter with an aqueous solution comprising a second surfactant having an HLB index greater than 13 to form a mixture; and dissolving the mixture to produce the mixed micelle composition, where the resulting composition is optically clear.

Suitable solvents that can be used in preparing the mixed micelle compositions of the present disclosure include short-chain alcohols, for example, methanol, ethanol, n-propanol, isopropanol, and butanol, as well as, chloroform, acetone, methylene chloride, dimethyl dulfoxide, dimethyl formamide and propylene glycol. The combination of two or three short chain alcohols may be used. Volatile organic solvents like chloroform and acetone may be used in combination with short chain alcohols. In an embodiment, the present disclosure provides a method of preparing a mixed micelle composition that includes mixing a calcineurin inhibitor with vitamin E TPGS in a short-chain alcohol to form a short-chain alcoholic solution; evaporating the short-chain alcoholic solution to form a near-solid matter; hydrating the near-solid matter with an aqueous solution comprising octoxynol-40 to form a mixture; and dissolving the mixture to produce the mixed micelle composition, where the resulting composition is optically clear.

In an embodiment, the short-chain alcohol is ethanol. In an embodiment, the present disclosure provides a method of preparing a mixed micelle composition that includes mixing a calcineurin inhibitor with vitamin E TPGS and octoxynol-40 in ethanol to form an ethanolic solution. In an embodiment, the ethanol is 95% ethanol. In another embodiment, the method provides for evaporating the ethanolic solution to form a near-solid matter. The near-solid matter may be resultant from rotary vacuum evaporation of the ethanolic solution, in which case the near-solid matter may be a thin film. The near-solid matter can also be resultant from evaporation of the ethanolic solution by, for example, lyophilization, freeze-drying, spray-drying, or by use of large and small scale evaporators, such as film evaporators, centrifugal evaporators, and vortex evaporators. The near-solid matter will be essentially free of ethanol (about <2% EtOH), but may contain up to about 5% water. In an embodiment, the method provides for hydrating the near-solid matter with an aqueous solution; and dissolving the mixture to produce the mixed micelle composition, wherein the resulting composition is optically clear. The dissolving step may be performed by sonication, mixing, vortexing, stirring, mixing by rotary motion in a rotary evaporator and/or shaking the near-solid matter in the aqueous solution, or by other methods known in the art. In an embodiment, the method further comprises mixing a bioadhesive polymer into the aqueous solution prior to the hydrating step. In an embodiment, the bioadhesive polymer is selected from PVP-K-30, PVP-K-90, HPMC, HEC, and polycarbophil. In an embodiment, the bioadhesive polymer is selected from PVP-K-30 or PVP-K-90. In an embodiment, the calcineurin inhibitor in the mixed micellar composition is voclosporin. In an embodiment, the voclosporin is present from about 0.001% to about 10% in the mixed micelle composition.

Pharmaceutically acceptable packaging materials for the compositions include, but are not limited to, polypropylene, polystyrene, low density polyethylene (LDPE), high density polyethylene (HDPE), polycarbonate, polyvinylidine chloride, and other materials known to those skilled in the art. The compositions can be packaged aseptically employing blow-fill-seal technology. Blow-fill-seal (BFS) describes an aseptic filling process in which hollow containers are blow molded, filled with sterile product, and sealed, all in one continuous machine cycle. The technology is an alternative to conventional aseptic filling and capping operations, often providing cost savings through high output and process efficiency. In an embodiment, the compositions of the present disclosure are filled to single-use bottles, packets, vials, ampoules, LDPE BFS containers, or HDPE BFS containers.

In an embodiment, multiple doses can be supplied as a plurality of single-use packages. In another embodiment, the compositions are conveniently packaged in a bottle, container or device that allows for metered application, including containers equipped with a dropper for topical ophthalmic application.

While the precise regimen is left to the discretion of the clinician, it is recommended that the compositions of the present disclosure be topically applied by placing one to two drops, or more, in each eye 1 to 4 times daily. For example, the composition may be applied 1, 2, 3, 4, 5, 6, 7 or 8 times a day, or more. In an embodiment, the composition are topically applied by placing one to two drops in each eye once or twice daily.

Artificial tears are lubricant eye drops used to treat, among other things, the dryness and irritation associated with deficient tear production in keratoconjunctivitis sicca (dry eyes). Artificial tears can also be used to moisten contact lenses, as well as, moisten eyes during an eye examination. Typically, artificial tears contain water, salts and polymers but lack the proteins found in natural tears. Various artificial tears are available over-the-counter that contain ingredients such as carboxymethyl cellulose, hydroxypropyl methylcellulose (a.k.a. HPMC or hypromellose), and hydroxypropyl cellulose. Adverse effects have been shown in the known over-the-counter artificial tears, which are usually a consequence of the carboxymethyl cellulose component and other similar lubricants. These adverse effects include, for example, eye pain, irritation, continued redness, or vision changes.

In one aspect, unique biocompatible artificial tear compositions are disclosed herein. The artificial tear compositions of the present disclosure are formulated as sterile, mixed micellar, aqueous solutions that include micelles formed from a first surfactant with an HLB index greater than about 10, and a second surfactant with an HLB index of greater than about 13. In an embodiment, the aqueous solution includes various ingredients chosen from one of hydrophilic polymer excipients, tonicity agents, buffers, preservatives, co-solvents or antioxidants. The biocompatible artificial tear compositions can be used to treat irritation, redness, swelling, allergic reaction, irritation due to contact lens use, and corneal scratches and abrasions of the eyes.

Various hydrophilic polymer excipients may be employed including, but not limited to, PVP-K-30, PVP-K-90, HPMC, HEC, and polycarbophil. In an embodiment, the hydrophilic polymer excipient is PVP-K-90.

Various tonicity agents may be employed to adjust the tonicity of the artificial tear compositions, preferably to that of natural tears. For example, sodium chloride, potassium chloride, magnesium chloride, calcium chloride and/or mannitol may be added to the compositions to approximate physiological tonicity. In an embodiment, the tonicity agent is sodium chloride. Such an amount of tonicity agent will vary, depending on the particular agent to be added. In general, however, the compositions will have a tonicity agent concentration of about 0.1-1.5% w/v.

An appropriate buffer system (e.g., sodium phosphate, sodium acetate, sodium citrate, sodium borate or boric acid in water) may be added to prevent pH drift under storage conditions. The particular concentration will vary, depending on the agent employed. In general, such a concentration will range from about 0.02 to 2.0% w/v. In an embodiment, the buffer system includes sodium phosphate. Further, the sodium phosphate may include both monosodium phosphate (i.e., monobasic) and disodium phosphate (i.e., dibasic). In an embodiment, the pH of the buffer system is adjusted such that an artificial tear composition of the presently disclosed embodiments ranges from about 6.5 to about 7.5.

Preservatives can be added to the artificial tear compositions of the present disclosure to increase the compositions shelf life and to facilitate the use of multi-dose bottles. Examples of preservatives include, but are not limited to, Benzalkonium Chloride (BAC), Chlorobutanol, GenAqua (Sodium Perborate) and Polyquad (Polyquatemium-1).

A representative formulation for an artificial tear composition according to the presently disclosed embodiments is shown in Example 16. Although specific concentration values are listed, those skilled in the art will recognize that the concentrations of the various ingredients can be varied. Similarly, it may not be necessary to include all of the ingredients listed in Example 16 in each artificial tear composition.

A method of preparing a mixed micelle composition includes mixing a calcineurin inhibitor or a mTOR inhibitor with a first surfactant having an HLB index greater than about 10 and a second surfactant having an HLB index of greater than about 13 in a solvent to form a solvent solution; evaporating the solvent solution to form a near-solid matter; hydrating the near-solid matter with an aqueous solution; and dissolving the near-solid mixture to produce the mixed micelle composition, wherein the composition is optically clear.

A method for treating an ocular disease in a patient in need thereof includes administering topically to an eye of the patient a composition comprising a therapeutically effective amount of a calcineurin inhibitor or mTOR inhibitor, the composition further having vitamin E TPGS and octoxynol-40, wherein the composition is an aqueous solution of mixed micelles.

A method for treating, reducing, ameliorating, or alleviating an inflammatory ocular disease in an animal includes providing a mixed micellar pharmaceutical composition having a calcineurin inhibitor or an mTOR inhibitor encapsulated in micelles, the micelles formed with a first surfactant with an HLB index greater than about 10 and a second surfactant with an HLB index of greater than about 13; and administering to the animal an amount of the pharmaceutical composition at a frequency sufficient to treat, reduce, ameliorate, or alleviate the inflammatory ocular disease.

A method for treating, reducing, ameliorating, or alleviating a back-of-the-eye condition or disorder in a subject includes providing a mixed micellar pharmaceutical composition having a calcineurin inhibitor encapsulated in micelles formed with a first surfactant with an HLB index greater than about 10 and a second surfactant with an HLB index of greater than about 13; and administering to the subject an amount of the pharmaceutical composition at a frequency sufficient to treat, reduce, ameliorate, or alleviate the back-of-the-eye condition or disorder.

EXAMPLES

In general, all reagents used are commercially available and used without further purification unless indicated otherwise. Voclosporin (voclosporin, LX211, ISA247) was obtained from Isotechnika, Inc., Edmonton, Alberta, Canada. The stock obtained from Isotechnika was stored by Lux Biosciences at the New Jersey Center for Biomaterials; Cyclosporine A was obtained from Xenos Bioresources, Inc., Santa Barbara, Calif.; Sirolimus and Tacrolimus were obtained from Haorui Pharma-Chem, Inc. Vitamin E TPGS (NF Grade) was obtained from Eastman Chemical Company, IGEPAL CA-897 (Octoxynol-40) was obtained from Rhodia, Inc., Distilled Deionized Water was prepared in house by use of EASY Pure UV Compact Ultra Pure Water System, (Barnstead, Iowa). Kollidon® 30 (PVP), and Kollidon® 90 F (Povidone K 90) were obtained from BASF. Hydroxyethyl Cellulose, 100 cps, and 5000 cps were obtained from Spectrum, Methocel®, HPMC was obtained from Colorcon, Noveon®, Polycarbophil was obtained from Lubrizol Advanced Materials.

Example 1

General Preparation of a Basic Formulation

In order to make formulations at drug concentration of 0.02, 0.2, 0.4, 0.5, and 1.0 wt %, the following protocols were employed. Drug basic formulations were made in the ratios shown in Table 1. In a first protocol, for example, calcineurin inhibitor and vitamin E TPGS required for 50 mL were calculated, weighed, then mixed in 5 mL 95% ethanol, until a clear solution was obtained. The ethanolic solution was evaporated under vacuum to get a thin film near-solid matter. Deionized water, 25 mL, was mixed with octoxynol-40 and the solution was added to the thin film near-solid matter and sonicated for approximately 20 min to ensure complete formation of mixed micelles. The prepared 2× formulations were stored at room temperature. Alternatively, in a second protocol, amounts of drug, vitamin E TPGS and octoxynol-40 required for 50 mL were calculated, weighed, then mixed in 5 mL 95% ethanol, and evaporated under vacuum to form a thin film near-solid matter. The thin film near-solid matter was then dissolved in 25 mL deionized water and sonicated or mixed by rotary motion in a rotary evaporator for approximately 20 min to ensure complete formation of mixed micelles. The prepared 2× formulations were stored at room temperature.

TABLE 1

Basic 2X Formulations (wt %/volume).

| Label/Ingredients | 1 | 2 | 3 |
|---|---|---|---|
| Drug | 0.4 | 0.8 | 1.0 |
| Vitamin E TPGS | 4.0 | 6.0 | 7.0 |
| Octoxynol-40 | 1.0 | 1.0 | 1.0 |

Example 2

General Preparation of Formulations

Basic 2× Formulations shown in Table 1 were prepared as described in the second protocol described in Example 1. Basic formulations were prepared where the calcineurin or mTOR inhibitor was voclosporin, cyclosporine A, sirolimus and tacrolimus. In one preparation for 50 mL of formulation; a buffer mixture was prepared by dissolving amounts of components shown in Table 2 in 25 mL of deionized water to prepare a 2× buffer. The 2× buffer mixture was prepared both with and without added preservatives.

TABLE 2

Buffer Mixture.

| Components | Amount for 50 mL | Amount for 50 mL | Amount for 50 mL | Amount for 50 mL |
|---|---|---|---|---|
| Sodium Phosphate, Dibasic | 0.4048 g | 0.4048 g | 0.4048 g | 0.4048 g |
| Sodium Phosphate, Monobasic | 0.4645 g | 0.4645 g | 0.4645 g | 0.4645 g |
| EDTA | 10 mg | N.A. | 10 mg | N.A. |
| Benzalkonium chloride | 10 mg | N.A. | N.A. | 10 mg |

N.A. = not added

The required amount of polymer excipient shown in Table 3A was dispersed in 2.5 mL 2× buffer mixture and gently vortexed to get a clear solution. The basic 2× formulation was added in equal volume and mixed to get uniform solution. The pH of the solution was adjusted with NaOH or HCl to a target of about 6.8. The osmolality of the solution was adjusted with NaCl to be in the range of about 280-300 mOsmol/kg. The formulation was sterilized by a nylon membrane filter (0.22 μm) and then stored at room temperature until use.

TABLE 3A

Formulations.

| Label/Ingredients | 1 | 2 | 3 | 4 | 5 | 6 |
|---|---|---|---|---|---|---|
| Basic Formulation (2X) | 2.5 mL | 2.5 mL | 2.5 mL | 2.5 mL | 2.5 mL | 2.5 mL |
| Buffer Mixture (2X) | | 2.5 mL | 2.5 mL | 2.5 mL | 2.5 mL | 2.5 mL |
| PVP-K-30 (1.8%) | | 90 mg | | | | |
| PVP-K-90 (1.2%) | | | 60 mg | | | |
| HPMC (0.5%) | | | | 25 mg | | |
| HEC (0.5%) | | | | | 25 mg | |
| Polycarbophil (0.5%) | | | | | | 25 mg |
| Water | 2.5 mL | | | | | |
| Total Approx. Vol. | 5 mL | 5 mL | 5 mL | 5 mL | 5 mL | 5 mL |

In an alternative procedure for preparation of 100 mL of formulations, the basic 2× formulations shown in Table 1 were prepared using voclosporin. In order to make formulations at voclosporin concentrations of 0.2, 0.4 and 0.5 wt %/volume, appropriate amounts of drug, vitamin E TPGS and octoxynol-40 required for 100 mL were calculated, weighed, then mixed in 10 mL 95% ethanol, and evaporated under vacuum for approximately 12 hours to form a thin film near-solid matter. The thin film near-solid matter was then dissolved in 50 mL deionized water and sonicated, or mixed by rotary motion in a rotary evaporator, for approximately 20 minutes to ensure complete formation of mixed micelles; then stored at room temperature. The required amount of polymer excipient shown in Tables 3B and 3C was dispersed in 40 mL deionized water and stirred to get a clear polymer solution. The other components shown in Tables 3B and 3C were added to the 50 mL basic 2× formulation and stirred well to get clear buffered solution. The clear buffered solution was slowly transferred into the clear polymer solution and mixed well. The pH of the solution was adjusted with NaOH or HCl to a target of about 6.8. The osmolality of the solution was maintained in the range of 280-300 mOsmol/kg. The volume was brought up to 100 mL with water. The formulation was sterilized by a nylon membrane filter (0.22 μm) and then stored at room temperature until use.

TABLE 3B

Formulations.

| Label/Ingredients | 1 | 2 | 3 | 4 | 5 | 6 |
|---|---|---|---|---|---|---|
| Basic Formulation (2X) | 50 mL | 50 mL | 50 mL | 50 mL | 50 mL | 50 mL |
| Povidone-K-30 | | 1.8 g | | | | |
| Povidone-K-90 | | | 1.2 g | | | |
| Hydroxy propyl methyl cellulose | | | | 0.5 g | | |
| Hydroxyethyl cellulose | | | | | 0.5 g | |
| Polycarbophil | | | | | | 0.9 g |
| Sodium phosphate, dibasic heptahydrate | 0.81 g | 0.81 g | 0.81 g | 0.81 g | 0.81 g | 0.81 g |
| Sodium phosphate, monobasic | 0.93 g | 0.93 g | 0.93 g | 0.93 g | 0.93 g | 0.93 g |
| Sodium chloride | 0.2 g | 0.2 g | 0.2 g | 0.2 g | 0.2 g | 0.2 g |
| Water up to | 100 mL | 100 mL | 100 mL | 100 mL | 100 mL | 100 mL |

TABLE 3C

| Label/Ingredients | Formulations. | | | | | |
|---|---|---|---|---|---|---|
| | 1 | 2 | 3 | 4 | 5 | 6 |
| Basic Formulation (2X) | 50 mL | 50 mL | 50 mL | 50 mL | 50 mL | 50 mL |
| Povidone-K-30 | | 1.8 g | | | | |
| Povidone-K-90 | | | 1.2 g | | | |
| Hydroxy propyl methyl cellulose | | | | 0.5 g | | |
| Hydroxyethyl cellulose | | | | | 0.5 g | |
| Polycarbophil | | | | | | 0.9 g |
| Sodium phosphate, dibasic heptahydrate | 0.81 g | 0.81 g | 0.81 g | 0.81 g | 0.81 g | 0.81 g |
| Sodium phosphate, monobasic | 0.93 g | 0.93 g | 0.93 g | 0.93 g | 0.93 g | 0.93 g |
| Sodium chloride | 0.2 g | 0.2 g | 0.2 g | 0.2 g | 0.2 g | 0.2 g |
| Benzylkonium chloride | 0.02 g | 0.02 g | 0.02 g | 0.02 g | 0.02 g | 0.02 g |
| EDTA | 0.02 g | 0.02 g | 0.02 g | 0.02 g | 0.02 g | 0.02 g |
| Water up to | 100 mL | 100 mL | 100 mL | 100 mL | 100 mL | 100 mL |

One optimized formulation with voclosporin concentration at 0.2% wt %/vol. is shown in Table 3D.

TABLE 3D

| Formulation at 0.2 wt %/volume Voclosporin. | |
|---|---|
| Ingredient | Amount |
| Voclosporin (LX211) | 0.2 g |
| Vitamin E TPGS | 2.0 g |
| Octoxynol-40 | 2.0 g |
| PVP-K-90 | 1.2 g |
| Sodium Phosphate, Dibasic | 0.81 g |
| Sodium Phosphate, Monobasic | 0.93 g |
| Sodium Chloride | 0.2 g |
| Water up to | 100 mL |

Unless otherwise stated, data below are for formulations at approximately 0.2% 5 voclosporin. The viscosity of the formulation was measured using cone and plate type viscometer. The clarity of the formulation was measured at 400 nm as described. Osmolality, pH, viscosity and absorbance at 400 nm for various formulations with 0.2% voclosporin are shown in Table 4A.

TABLE 4A

| | Formulation Characteristics. | | | | |
|---|---|---|---|---|---|
| | Osmolality (mOsmol/kg) | | | | |
| Label/Ingredients | Before addition of NaCl | After addition of NaCl | pH | Viscosity (Poise) | Absorbance at 400 nm |
| Basic Formulation (1X) | 010 | — | — | 0.06 | 0.025 |
| Basic Formulation (2X) + Buffer Mixture (2X) | 218 | — | 6.83 | 0.07 | 0.021 |
| B. For + BM + PVP-K-30 | 248 | 347 | 6.85 | 0.07 | 0.032 |
| B. For + BM + PVP-K-90 | 224 | 303 | 6.81 | 0.08 | 0.034 |
| B. For + BM + HPMC | 228 | 311 | 6.82 | 0.11 | 0.025 |
| B. For + BM + HEC | 237 | 283 | 6.80 | 0.08 | 0.031 |
| B. For + BM + Polycarbophil | 248 | 289 | 6.83 | 0.08 | 0.046 |

A Cyclosporine A (CsA) formulation was prepared in the concentrations shown in Table 4B a similar fashion as described in the second protocol in Example 1.

TABLE 4B

| CsA Formulation. | |
|---|---|
| Label/Ingredients | wt %/vol |
| Drug (CsA) | 0.05 |
| Vitamin E TPGS | 3 |
| Octoxynol-40 | 0.02 |
| Hydroxy Ethyl Cellulose | 0.2 |
| Benzalkonium Chloride | 0.01 |
| EDTA | 0.01 |
| Sodium Chloride | 0.86 |
| Water | 100 |

The CsA formulation was adjusted to pH 6.88 and osmolality was 320 mOsm/kg.

Example 3

Determination of Drug Content

Each formulation was analyzed for drug content by HPLC. The HPLC mobile phase consisted of acetonitrile/water/trifluoroacetic acid (75:25:0.1 v/v/v) at a flow rate of 1 mL/min with elution of the compound of interest from a reversed-phase phenyl column (5 microns, 15×4.6 mm). The absorbance of the drug was measured at 210 nm with an UV detector and compared with a standard curve of the target drug at various known concentrations. Observed peak for voclosporin eluted at approximately 5.5 min.

Example 4

Filtration Efficiency Test

Various types of membranes were tested for use in filter sterilization of formulations containing 0.2 wt % voclosporin. Membranes of 0.22 µM pore size were of various materials including nylon, teflon, and polycarbonate. Recovery from membranes was evaluated by HPLC determination of drug content described above and compared to centrifuged sample. Results for comparative filtration efficiency tests are shown in Tables 5A and 5B. Generally, nylon, teflon, and polycarbonate membranes of 0.22 µM were each found acceptable for filter sterilization.

TABLE 5A

Filtration Efficiency Test 1.

| Formulation | Area | Conc. (µg/mL) | Exp. Conc. (µg/mL) | % Recovery | Amount of drug in 50 mL (g) | Drug content (in percent) |
|---|---|---|---|---|---|---|
| Centrifuged Sample ||||||| 
| 1 | 4619728 | 2108.93 | 2200 | 95.86 | 0.105446 | 0.211 |
| 2 | 4571834 | 2089.58 | 2200 | 94.98 | 0.104479 | 0.209 |
| 3 | 4589872 | 2096.87 | 2200 | 95.31 | 0.104843 | 0.210 |
| Nylon Membrane ||||||| 
| 1 | 4537680 | 2075.78 | 2200 | 94.35 | 0.103789 | 0.208 |
| 2 | 4512464 | 2065.60 | 2200 | 93.89 | 0.10328 | 0.207 |
| Teflon Membrane ||||||| 
| 1 | 4581475 | 2093.48 | 2200 | 95.16 | 0.104674 | 0.209 |
| 2 | 4567613 | 2087.88 | 2200 | 94.90 | 0.104394 | 0.209 |
| 3 | 4639411 | 2116.88 | 2200 | 96.22 | 0.105844 | 0.212 |

TABLE 5B

Filtration Efficiency Test 2.

| Formulation | Area | Conc. (µg/mL) | Exp.Conc (µg/mL) | % Recovery | Amount of drug in 50 mL (g) | Drug content (in percent) |
|---|---|---|---|---|---|---|
| Centrifuged Sample ||||||| 
| 1 | 4531917 | 2073.45 | 2200 | 94.25 | 0.103673 | 0.207 |
| 2 | 4506733 | 2063.28 | 2200 | 93.79 | 0.103164 | 0.206 |
| 3 | 4514394 | 2066.38 | 2200 | 93.93 | 0.103319 | 0.207 |
| Polycarbonate Membrane ||||||| 
| 1 | 4491373 | 2057.08 | 2200 | 93.50 | 0.102854 | 0.206 |
| 2 | 4522797 | 2069.77 | 2200 | 94.08 | 0.103489 | 0.207 |
| 3 | 4482973 | 2053.68 | 2200 | 93.35 | 0.102684 | 0.205 |

Formulations at 0.2 wt % voclosporin with various bioadhesive polymer excipients were prepared as described above in Table 3C. Formulation characteristics were measured and drug content was determined by HPLC after filtration through a 0.22 µm nylon membrane. Results are shown in Table 6.

TABLE 6

Drug Content in 0.2 wt % Voclosporin Formulations.

| Parameter | 1X Basic Formulation | PVP-K-30 | PVP-K-90 | HPMC | HEC | PC |
|---|---|---|---|---|---|---|
| pH (before adjustment) | 6.36 | 6.40 | 6.38 | 6.41 | 6.31 | 4.60 |
| pH (after adjustment) | 6.80 | 6.81 | 6.80 | 6.82 | 6.82 | 6.80 |
| Osmolality (mOsm/kg) | 325 | 328 | 303 | 280 | 297 | 330 |
| Viscosity (Poise) | 0.11 | 0.12 | 0.13 | 0.17 | 0.16 | 0.19 |
| Drug Content (%) by HPLC | 0.203 | 0.202 | 0.192 | 0.191 | 0.173 | 0.183 |

Example 5

Clarity of the Formulations

The clarity of the formulations was measured visually and by recording the absorbance of the sample at 400 nm using an UV-visible spectrophotometer. One milliliter of formulation and corresponding drug free vehicles were placed in a plastic cuvette and absorbance was recorded at 400 nm. Water was used as blank. In a preferred aspect, the mixed micellar formulation is a clear formulation with absorbance at 400 nm of less than about 0.1. Absorbance at 400 nm is shown for various formulations in Table 4A, and in dilution experiments in Tables 9-14.

Visual clarity was also used as a guideline in formulation trials. For example, Tables 7 and 8 show visual clarity at various wt % of voclosporin, vitamin E TPGS and octoxynol-40 in various 1× basic formulations, prepared as described in the second protocol in Example 1.

TABLE 7

Formulation Trials.

| Label/Ingredients | 1 | 2 | 3 | 4 |
|---|---|---|---|---|
| Drug (Voclosporin) (wt %) | 2.0 | 2.0 | 2.0 | 2.0 |
| Vitamin E TPGS (food grade) (wt %) | 4.5 | 5.0 | 5.5 | 6.0 |
| Octoxynol-40 (wt %) | 3.0 | 3.0 | 3.0 | 3.0 |
| Water up to (mL) | 100 | 100 | 100 | 100 |
| Visual clarity | milky | milky | milky | milky |

In Table 7, food grade vitamin E TPGS was used at the concentrations shown; all samples were milky. In Table 8, samples 1 and 2 were visually clear, but samples 3 and 4 contained undissolved drug.

TABLE 8

Formulation Trials.

| Label/Ingredients | 1 | 2 | 3 | 4 |
|---|---|---|---|---|
| Drug (Voclosporin) (wt %) | 0.75 | 1.0 | 1.5 | 2.0 |
| Vitamin E TPGS (wt %) | 6.0 | 6.0 | 6.0 | 6.0 |
| Octoxynol-40 (wt %) | 4.0 | 4.0 | 4.0 | 4.0 |
| Water up to (mL) | 100 | 100 | 100 | 100 |
| Visual clarity | clear | clear | cloudy | cloudy |

Example 6

Dilution Study of Voclosporin Formulations in Artificial Tears

Voclosporin formulations were evaluated in dilution studies. The goal was to subject formulations to dilution under conditions similar to the eye. The voclosporin concentration was 0.2 wt % in each formulation tested. The formulations as described in Table 3A were each mixed 1:1, 1:5 and 1:10 with various brands of artificial tears available over the counter (OTC) in the pharmacy. Systane® (Lubricant Eye Drops, Alcon, Inc.; Visine® (Lubricant Eye Drops, Pfizer, Inc.; Refresh Tears® (Lubricant Eye Drops), Allergan, Inc.; and Hypo Tears® (Lubricant Eye Drops), Novartis, were employed. The measurements were taken under ambient conditions. The data (absorbance at 400 nm) are shown in Tables 9 to 14A. Results showed no increase in turbidity and hence no precipitation of voclosporin out of solution.

TABLE 9

Sample Absorbance at 400 nm, pre-dilution.

| Sample No. | Formulations | Absorbance (400 nm) |
|---|---|---|
| 1 | PVP-K-30 | 0.020 |
| 2 | PVP-K-90 | 0.018 |
| 3 | HPMC | 0.021 |
| 4 | HEC | 0.019 |
| 5 | Polycarbophil | 0.192 |
| 6 | Water | 0.000 |
|   | Tears Fluid |   |
| 7 | Refresh Tears | 0.000 |
| 8 | Visine Tears | 0.017 |
| 9 | Systane Tears | 0.023 |
| 10 | Hypo Tears | 0.002 |

TABLE 10

Sample Absorbance at 400 nm, post-dilution.

| Sample No: | Formulation | Type of tear fluid | Dilution factor | Absorbance (400 nm) |
|---|---|---|---|---|
| 11 | PVP-K-30 | Refresh Tears | 2× | 0.020 |
| 12 |   |   | 5× | 0.014 |
| 13 |   |   | 10× | 0.002 |
| 14 |   | Visine Tears | 2× | 0.011 |
| 15 |   |   | 5× | 0.005 |
| 16 |   |   | 10× | 0.002 |
| 17 |   | Systane Tears | 2× | 0.019 |
| 18 |   |   | 5× | 0.019 |
| 19 |   |   | 10× | 0.021 |
| 20 |   | Hypo Tears | 2× | 0.013 |
| 21 |   |   | 5× | 0.005 |
| 22 |   |   | 10× | 0.041 |

TABLE 11

Sample Absorbance at 400 nm, post-dilution.

| Sample No: | Formulation | Type of tear fluid | Dilution factor | Absorbance (400 nm) |
|---|---|---|---|---|
| 23 | PVP-K-90 | Refresh Tears | 2× | 0.012 |
| 24 |   |   | 5× | 0.007 |
| 25 |   |   | 10× | 0.004 |
| 26 |   | Visine Tears | 2× | 0.013 |
| 27 |   |   | 5× | 0.006 |
| 28 |   |   | 10× | 0.003 |
| 29 |   | Systane Tears | 2× | 0.020 |
| 30 |   |   | 5× | 0.020 |
| 31 |   |   | 10× | 0.031 |
| 32 |   | Hypo Tears | 2× | 0.010 |
| 33 |   |   | 5× | 0.005 |
| 34 |   |   | 10× | 0.003 |

TABLE 12

Sample Absorbance at 400 nm, post-dilution.

| Sample No: | Formulation | Type of tear fluid | Dilution factor | Absorbance (400 nm) |
|---|---|---|---|---|
| 35 | HPMC | Refresh Tears | 2× | 0.010 |
| 36 |   |   | 5× | 0.004 |
| 37 |   |   | 10× | 0.001 |
| 38 |   | Visine Tears | 2× | 0.009 |

TABLE 12-continued

Sample Absorbance at 400 nm, post-dilution.

| Sample No: | Formulation | Type of tear fluid | Dilution factor | Absorbance (400 nm) |
|---|---|---|---|---|
| 39 | | | 5× | 0.005 |
| 40 | | | 10× | −0.001 |
| 41 | | Systane Tears | 2× | 0.018 |
| 42 | | | 5× | 0.021 |
| 43 | | | 10× | 0.021 |
| 44 | | Hypo Tears | 2× | 0.009 |
| 45 | | | 5× | 0.004 |
| 46 | | | 10× | 0.002 |

TABLE 13

Sample Absorbance at 400 nm, post-dilution.

| Sample No: | Formulation | Type of tear fluid | Dilution factor | Absorbance (400 nm) |
|---|---|---|---|---|
| 47 | HEC | Refresh Tears | 2× | 0.009 |
| 48 | | | 5× | 0.004 |
| 49 | | | 10× | 0.002 |
| 50 | | Visine Tears | 2× | 0.010 |
| 51 | | | 5× | 0.004 |
| 52 | | | 10× | 0.002 |
| 53 | | Systane Tears | 2× | 0.020 |
| 54 | | | 5× | 0.020 |
| 55 | | | 10× | 0.020 |
| 56 | | Hypo Tears | 2× | 0.010 |
| 57 | | | 5× | 0.004 |
| 58 | | | 10× | 0.003 |

TABLE 14A

Sample Absorbance at 400 nm, post-dilution.

| Sample No: | Formulation | Type of tear fluid | Dilution factor | Absorbance (400 nm) |
|---|---|---|---|---|
| 59 | Polycarbophil | Refresh Tears | 2× | 0.052 |
| 60 | | | 5× | 0.078 |
| 61 | | | 10× | 0.054 |
| 62 | | Visine Tears | 2× | 0.046 |
| 63 | | | 5× | 0.086 |
| 64 | | | 10× | 0.065 |
| 65 | | Systane Tears | 2× | 0.038 |
| 66 | | | 5× | 0.053 |
| 67 | | | 10× | 0.047 |
| 68 | | Hypo Tears | 2× | 0.030 |
| 69 | | | 5× | 0.013 |
| 70 | | | 10× | 0.008 |

Further dilution studies were performed on the formulation shown in Table 3B, column 1, with buffered saline as diluent. Diluted formulation was characterized and data are shown in Table 14B. Micellar stability was confirmed to at least 20 fold dilution in buffered saline.

TABLE 14B

Micellar Stability Upon Dilution.

| Formulation | Dilution Factor | Appearance | pH | Osmolality (mOsm/kg) | Particle Size (nm) | PD | DST (° C.) | RS Time |
|---|---|---|---|---|---|---|---|---|
| No polymer | 0X | Clear | 6.78 | 326 | 10.6 | 0.037 | 55 | 3 min |
| | 4X | Clear | 6.87 | 340 | 12.2 | 0.161 | 60 | 3 min 40 sec |
| | 20X | Clear | 7.08 | 300 | 20.8 | 0.264 | 65 | 2 min |
| | 100X | Clear | 7.25 | 301 | 339.6 | 0.537 | — | — |

DST—Dissociation Temperature,
RS—Restabilization,
PD—Polydispersity

Example 7

Dissociation Temperature for the Drug Free Formulations and Formulations Containing Voclosporin Formulations shown in Table 3A were tested to determine dissociation temperature with and without 0.2 wt % voclosporin/volume. A water bath at a constant temperature of ~60° C. was prepared and used for testing of samples with drug. A glass vial containing the formulation was inserted into the water bath with a thermometer inserted in the formulation. As soon as some turbidity was visually observed, a temperature reading was taken. The turbid solutions were cooled to room temperature and the drug went back into the mixed micelles with the result that all solutions became clear again. The time for re-stabilization (reestablishment of visual clarity) was recorded. Data for samples with voclosporin are shown in Table 15. A heat block was used to heat and test samples without drug in a similar fashion. Data for samples without voclosporin are shown in Table 16.

The data shows that in the absence of voclosporin, the dissociation temperature of the micellar formulations generally is about 20-40 degrees celsius higher than the dissociation temperature of the micellar formulation in the presence of voclosporin (with the exception of the HPMC-containing formulation). The decrease in the dissociation temperature of the drug-containing micellar formulations indicates that the drug is incorporated into the micelles, and thereby solubilized.

TABLE 15

Dissociation Temperature of Formulation with 0.2 wt % Voclosporin.

| Sample No: | Formulations with 0.2% Voclosporin. | Temperature (° C.) | Time Required for Restabilization |
|---|---|---|---|
| 1 | Formulation without polymer (basic) | 44 | 6 min |
| 2 | PVP-K-30 | 46 | 5 min 30 sec |
| 3 | PVP-K-90 | 45 | 4 min 30 sec |
| 4 | HPMC | 44 | 2 min |
| 5 | HEC | 43 | 5 min |
| 6 | Polycarbophil | 43 | ND |

ND = Not Determined

TABLE 16

Dissociation Temperature of Formulation without Voclosporin.

| Sample No: | Drug free Formulations | Temperature (° C.) |
|---|---|---|
| 7 | PVP-K-30 | 92 |
| 8 | PVP-K-90 | 90 |
| 9 | HPMC | 46 |
| 10 | HEC | 90 |
| 11 | Polycarbophil | 75 |

An additional thermal dissociation experiment was performed wherein vials containing 1 mL of 0.2% voclosporin formulations (basic, HPMC, and PVP-K-90) were heated in a water bath maintained at 50° C. for about 5 minutes. The mixed micelles were destabilized and the solution became turbid or milky white. The solutions were cooled to room temperature and the drug went back into the mixed micelles with the result that all solutions became clear again. The time for re-stabilization was recorded. The PVP-K-90 sample was recycled a second time with the same results.

Generally, formulations with an increased wt % of octoxynol-40 exhibited an increase in the dissociation temperature and decreased the regeneration time (the time required for re-stabilization), as shown in Tables 17 and 18.

TABLE 17

Dissociation Temperatures in Basic Formulations with 0.2 wt % Voclosporin and various wt % Octoxynol-40.

| Sample No: | Concentration of Octoxynol-40 | Dissociation Temperature (° C.) | Time required for re-stabilization |
|---|---|---|---|
| 1 | 0.5% | 46 | 7 min 30 sec |
| 2 | 1.0% | 53 | 6 min 10 sec |
| 3 | 1.5% | 55 | 5 min 30 sec |
| 4 | 2.0% | 55 | 3 min 20 sec |
| 5 | 2.5% | 56 | 3 min |

TABLE 18

Dissociation Temperatures in Basic Formulations with 0.5 wt % Voclosporin and various wt % Octoxynol-40.

| Sample No: | Concentration of Octoxynol-40 | Dissociation Temperature (° C.) | Time required for re-stabilization |
|---|---|---|---|
| 1 | 0.5% | 46 | Not stabilized |
| 2 | 1.0% | 46 | 6 min |
| 3 | 1.5% | 47 | 5 min |
| 4 | 2.0% | 48 | 7 min |
| 5 | 2.5% | 49 | 7 min 30 sec |
| 6 | 3.0% | 49 | 7 min 30 sec |

Another dissociation temperature experiment where the concentration of octoxynol-40 was increased from 0.5% to 2.5% in the PVP-K-90 formulation with 0.2 wt % voclosporin resulted in an increase in dissociation temperature from 45° C. to 55° C. The formulation reestablished to a clear solution within 3 minutes after cooling.

Addition of further excipients was evaluated to determine the effect on dissociation temperature. Addition of 5% PEG 400 to formulations as prepared in Table 3B with 0.2 wt % voclosporin resulted in similar dissociation temperatures and slightly increased time required for re-stabilization, as shown in Table 19.

TABLE 19

Dissociation Temperature: Effect of Addition of 5% (v/v) PEG 400.

| Sample No. | Formulations with Voclosporin | Dissociation Temperature (° C.) | Time Required for re-stabilization |
|---|---|---|---|
| 1 | Formulation without polymer + 5% PEG 400 | 42 | 6 min |
| 2 | PVP-K-90 + 5% PEG 400 | 44 | 6 min |
| 3 | HPMC + 5% PEG 400 | 42 | 2 min 45 sec |
| 4 | HEC + 5% PEG 400 | 39 | 6 min |

Addition of 1% HPMC to formulations as prepared in Table 3B with 0.2 wt % voclosporin and PVP-K-90 resulted in similar dissociation temperatures, but a decreased time required for re-stabilization, as shown in Table 20.

TABLE 20

Dissociation Temperature: Effect of Addition of 1% HPMC to PVP-K-90 Formulation.

| Sample No. | Formulation with Voclosporin | Dissociation Temperature (° C.) | Time Required for re-stabilization |
|---|---|---|---|
| 1 | PVP-K-90 + HPMC | 43 | 3 min 45 sec |

Example 8

Particle Size Measurements

The mean particle size and polydispersity index of the mixed micelles are measured using dynamic light scattering technique (Brookhaven 90Plus particle size analyzer, Holtsville, N.Y.), taking the average of three measurements. The different solutions were placed in disposable plastic cells. A sample volume of 200 μL was used for determining the particle size. Particle size and polydispersity for formulations as prepared in Example 2 with 0.2 wt % voclosporin are shown in Table 21. The formulation with 0.2 wt % voclosporin and PVP-K-90 exhibited an average micelle diameter of 13.3 nm with a very narrow size distribution and a polydispersity of 0.005. In contrast, the formulation with 0.2 wt % voclosporin and HEC exhibited an average micelle diameter of 23.8, but a broad, bimodal particle size distribution resulted in a large polydispersity of 0.482.

TABLE 21

Particle Size Analysis.

| Sample No. | Formulation with 0.2 wt % Voclosporin | Diameter (nm) | Polydispersity |
|---|---|---|---|
| 1 | Formulation without polymer | 8.0 | 0.657 |
| 2 | PVP-K-30 | 19.8 | 0.206 |
| 3 | PVP-K-90 | 13.3 | 0.005 |
| 4 | HPMC | 32.9 | 0.317 |
| 5 | HEC | 23.8 | 0.482 |

Particle size, polydispersity, dissociation temperature and re-stabilization time for formulations with 0.2 wt % and 0.5 wt % voclosporin in formulations with 2% octoxynol-40 are shown in Tables 22 and 23.

TABLE 22

Characteristics of Formulations Containing 0.2 wt % Voclosporin with 2% Octoxynol-40.

| Sample No | Formulations | Osmolality (mOsm/kg) | Particle Size (nm) | Polydispersity index | Dissociation Temperature (° C.) | Time required for re-stabilization |
|---|---|---|---|---|---|---|
| 1 | Formulation without Buffer & polymer | 75 | 9.9 | 0.103 | 57 | 2 min |
| 2 | Formulation without polymer | 231 | 11.1 | 0.157 | 58 | 2 min 40 sec |
| 3 | Formulation containing 3% OC-40 without polymer | 248 | 10.5 | 0.083 | 65 | 3 min |
| 4 | PVP-K-30 (1.8%) | 256 | 11.6 | 0.147 | 58 | 3 min |
| 5 | PVP-K-90 (1.2%) | 266 | 12.5 | 0.156 | 59 | 3 min 20 sec |
| 6 | HPMC (0.3%) | 275 | 97.3 | 0.160 | 53 | 3 min |
| 7 | HEC (0.3%) | 233 | 83.9 | 0.166 | 59 | 2 min 50 sec |

TABLE 23

Characteristics of Formulations Containing 0.5 wt % Voclosporin with 2% Octoxynol-40.

| Sample No | Formulations | Osmolality (mOsm/kg) | Particle Size (nm) | Polydispersity index | Dissociation Temperature (° C.) | Time required for re-stabilization |
|---|---|---|---|---|---|---|
| 1 | Formulation without Buffer & polymer | 178 | 9.6 | 0.030 | 49 | 14 min |
| 2 | Formulation without polymer | 275 | 10.6 | 0.055 | 46 | 12 min |
| 3 | Formulation containing 3% Octoxynol-40 without polymer | 358 | 11.0 | 0.115 | 44 | 13 min |
| 4 | PVP-K-30 (1.8%) | 284 | 12.7 | 0.189 | 47 | 12 min |
| 5 | PVP-K-90 (1.2%) | 281 | 21.8 | 0.251 | 48 | 12 min 50 sec |

Example 9

Determination of Drop Weight and Volume

In order to determine the amount of calcineurin inhibitor delivered per drop, the drop weight and volume was determined for each formulation. Since the drop size is dependent on the surface tension of the formulation, two formulations, as described in Table 3A, containing 0.2 wt % voclosporin/volume were tested for delivered drop size and volume. The formulation containing PVP-K-90, and the formulation containing HPMC, 0.5 mL each, were filled individually into 0.8 mL capacity BFS (blow-fill-seal) containers provided by a manufacturing vendor. The bottle material was LDPE and the study was conducted under ambient conditions. Ten drops of each formulation was squeezed into a tared dish and weighed. Similarly ten drops of formulations were squeezed in to the measuring cylinder and volume was recorded. Data is shown in Tables 24 and 25.

TABLE 24

Weight of 10 Drops.

| | Weight of 10 drops (g) | |
|---|---|---|
| Sample No | PVP-K-90 | HPMC |
| 1 | 0.2843 | 0.2851 |
| 2 | 0.2829 | 0.2843 |
| 3 | 0.2838 | 0.2848 |
| Average | 0.2836 | 0.2847 |

TABLE 25

Volume of 10 Drops.

| | Volume of 10 drops (mL) | |
|---|---|---|
| Sample No | PVP-K-90 | HPMC |
| 1 | 0.29 | 0.30 |
| 2 | 0.28 | 0.29 |
| 3 | 0.28 | 0.29 |
| Average | 0.283 | 0.293 |

Example 10

Stability Studies

Stability and formulation compatibility studies were performed in three types of bottles suitable for pharmaceutical delivery. Known volumes of the six formulations of Example 1 were transferred to three different types of containers i.e., LDPE, polypropylene and polyvinylchloride and stored at room temperature. At predetermined time intervals (0, 6, 24 and 48 hr) the samples were withdrawn from the containers and analyzed for the drug content by HPLC method. None of the formulations stored in various types of containers exhibited a decrease in drug content during the study period.

Example 11

Local Tolerability in Rabbits of Formulations Comprising a Calcineurin Inhibitor A study was conducted in rabbits to test the tolerance of mixed micellar formulations containing voclosporin (1× basic formulation, Table 3A, column 1, at either 0.2 wt % or 0.5 wt % voclosporin, one rabbit each) against saline solution. Healthy young adult New Zealand albino rabbits (3-4 Kg) were used for the study. One drop (approximately 30 µL) of saline was placed in one eye and a drop of formulation with voclosporin was placed in the other eye of the rabbit. No difference was noticed in the following observed parameters: blinking of the eye, lacrimation, pupil size, redness, movement of the eye.

Example 12

Local Tolerability in Rabbits of Formulations Comprising a Calcineurin Inhibitor Further studies were conducted in rabbits to test the tolerance of various mixed micellar formulations. Formulations F1-F16 as shown in Tables 26 and 27 were used for these studies.

TABLE 26

| | Formulations F1 to F8. | | | | | | | |
|---|---|---|---|---|---|---|---|---|
| Code | F1 | F2 | F3 | F4 | F5 | F6 | F7 | F8 |
| Voclosporin | 0.2% | 0.2% | 0.2% | 0.2% | 0.2% | 0.2% | 0.2% | 0.2% |
| Vitamin E TPGS | 2% | 2% | 3.5% | 3.5% | 2% | 2% | 3.5% | 3.5% |
| OX-40 | 2% | 3% | 2% | 3% | 2% | 3% | 2% | 3% |
| PVP-K-90 | — | — | — | — | 0.6% | 0.6% | 0.6% | 0.6% |

TABLE 27

| | Formulations F9 to F16. | | | | | | | |
|---|---|---|---|---|---|---|---|---|
| Code | F9 | F10 | F11 | F13 | F14 | F14 | F15 | F16 |
| Voclosporin | 0.2% | 0.2% | 0.2% | 0.2% | 0.02% | 0.02% | 0.02% | 0.02% |
| Vitamin E TPGS | 2% | 2% | 3.5% | 3.5% | 2% | 2% | 3.5% | 3.5% |
| OX-40 | 2% | 3% | 2% | 3% | 2% | 3% | 2% | 3% |
| PVP-K-90 | 1.2% | 1.2% | 1.2% | 1.2% | 1.2% | 1.2% | 1.2% | 1.2% |

Healthy young adult New Zealand albino rabbits (3-4 Kg) were used for the study. One drop (approximately 30 µL) of a formulation with voclosporin (LX211) was placed in an eye of the rabbit. Each formulation was tested in triplicate.

Both eyes of each animal were examined by a board-certified veterinary ophthalmologist using a hand-held slit lamp and indirect ophthalmoscope. Both control and test eyes were graded according to conjunctival congestion, swelling, and discharge, aqueous flare, iris light reflex and involvement, corneal cloudiness severity and area, pannus, fluorescein examination and lens opacity using the Hackett/McDonald scoring system (see, for example, Hackett, R. B. and McDonald, T. O. *Ophthalmic Toxicology* and *Assessing Ocular Irritation*. Dermatoxicology, 5$^{th}$ Edition. Ed. F. N. Marzulli and H. I. Maibach. Washington, D.C.: Hemisphere Publishing Corporation. 1996; 299-305 and 557-566.). In the fluorescein examination, approximately one drop of 0.9% sodium chloride, USP, was applied to the end of a fluorescein impregnated strip and then applied to the superior sclera of the left and right eyes (one fluorescein impregnated strip is used for each animal). After an approximate 15 second exposure, the fluorescein dye was gently rinsed from each eye with 0.9% sodium chloride, USP. The eyes were then examined using a slit lamp with a cobalt blue filtered light source. For the lenticular examination approximately one drop of a short-acting mydriatic solution was instilled onto each eye in order to dilate the pupil. After acceptable dilation has occurred, the lens of each eye was examined using a slit-lamp biomicroscope.

The crystalline lens is readily observed with the aid of the slit-lamp biomicroscope, and the location of lenticular opacity can readily be discerned by direct and retro illumination. The location of lenticular opacities can be arbitrarily divided into the following lenticular regions beginning with the anterior capsule: Anterior subcapsular, Anterior cortical Nuclear Posterior cortical, Posterior subcapsular, Posterior capsular. The lens is evaluated routinely during ocular evaluations and graded as either 0 (normal) or 1 (abnormal). The presence of lenticular opacities should be described and the location noted. Results for various formulations are shown in Tables 28 to 31.

TABLE 28

Tolerability Test Results in Rabbit Eyes for Various Formulations at 0.2 wt % Voclosporin.

| Rabbit # | | Pre Treatment | | | | 1 Hour | | | | 24 Hour | | | | 72 Hour | | | |
|---|---|---|---|---|---|---|---|---|---|---|---|---|---|---|---|---|---|
| | | F1 | F2 | F3 | F4 | F1 | F2 | F3 | F4 | F1 | F2 | F3 | F4 | F1 | F2 | F3 | F4 |
| I59 | 0% | 0 | 0 | | | 1 | 1 | | | 0 | 0 | | | 0 | 0 | | |
| I60 | PVP- | | | 0 | 0 | | | 0 | 0 | | | 0 | 0 | | | 0 | 0 |
| I61 | K-90 | 0 | | 0 | | 1 | | 0 | | 0 | | 0 | | 0 | | 1 | |
| I62 | | | 1 | | 1 | | 1 | | 1 | | 1 | | 2 | | 2 | | 0 |
| I63 | | 0 | | 0 | 0 | | | 0 | 0 | | | 0 | 0 | | | | 0 |
| I64 | | | 0 | 0 | | | 0 | 1 | | | 0 | 0 | | | 0 | 0 | |

TABLE 29

Tolerability Test Results in Rabbit Eyes for Various Formulations at 0.2 wt % Voclosporin.

| Rabbit # | | Pre Treatment | | | | 1 Hour | | | | 24 Hour | | | | 72 Hour | | | |
|---|---|---|---|---|---|---|---|---|---|---|---|---|---|---|---|---|---|
| | | F5 | F6 | F7 | F8 | F5 | F6 | F7 | F8 | F5 | F6 | F7 | F8 | F5 | F6 | F7 | F8 |
| I65 | 0.6% | 0 | 0 | | | 0 | 0 | | | 0 | 0 | | | 0 | 0 | | |
| I66 | PVP- | | | 1 | 1 | | | 1 | 1 | | | 0 | 0 | | | 0 | 0 |
| I67 | K-90 | 0 | | 0 | | 1 | | 2 | | 0 | | 0 | | 0 | | 0 | |
| I68 | | | 0 | | 0 | | 0 | | 0 | | 1 | | 0 | | 0 | | 0 |
| I69 | | 0 | | | 0 | 1 | | | 1 | 1 | | | 1 | 1 | | | 0 |
| I70 | | | 0 | 0 | | | 1 | 1 | | | 0 | 0 | | | 0 | 0 | |

TABLE 30

Tolerability Test Results in Rabbit Eyes for Various Formulations at 0.2 wt % Voclosporin.

| Rabbit # | | Pre Treatment | | | | 1 Hour | | | | 24 Hour | | | | 72 Hour | | | |
|---|---|---|---|---|---|---|---|---|---|---|---|---|---|---|---|---|---|
| | | F9 | F10 | F11 | F12 | F9 | F10 | F11 | F12 | F9 | F10 | F11 | F12 | F9 | F10 | F11 | F12 |
| I71 | 1.2% | 0 | 0 | | | 0 | 0 | | | 0 | 0 | | | 0 | 0 | | |
| I72 | PVP- | | | 0 | 0 | | | 1 | 0 | | | 0 | 0 | | | 0 | 0 |
| I73 | K-90 | 0 | | 0 | | 0 | | 0 | | 0 | | 0 | | 0 | | 0 | |
| I74 | | | 0 | | 0 | | 0 | | 0 | | 0 | | 0 | | 0 | | 0 |
| I75 | | 0 | | | 0 | 0 | | | 0 | | | 0 | 0 | | | 0 | 0 |
| I76 | | | 0 | 0 | | | 0 | 1 | | | 0 | 0 | | | 0 | 0 | |

TABLE 31

Tolerability Test Results in Rabbit Eyes for Various Formulations at 0.02 wt % Voclosporin

| Rabbit # | | Pre Treatment | | | | 1 Hour | | | | 24 Hour | | | | 72 Hour | | | |
|---|---|---|---|---|---|---|---|---|---|---|---|---|---|---|---|---|---|
| | | F13 | F14 | F15 | F16 | F13 | F14 | F15 | F16 | F13 | F14 | F15 | F16 | F13 | F14 | F15 | F16 |
| I77 | 1.2% | 0 | 0 | | | 0 | 1 | | | 0 | 0 | | | 0 | 0 | | |
| I78 | PVP- | | | 0 | 0 | | | 2 | 0 | | | 0 | 0 | | | 0 | 0 |
| I79 | K-90 | 0 | | 0 | | 0 | | 0 | | 0 | | 0 | | 0 | | 0 | |
| I80 | | | 0 | | 0 | | 0 | | 0 | | 0 | | 1 | | 0 | | 0 |
| I35 | | 0 | | | 0 | 0 | | | 0 | 0 | | | 0 | 0 | | | 0 |
| I36 | | | 0 | 0 | | | 0 | 1 | | | 1 | 1 | | | 0 | 2 | |

Example 13

Topical Voclosporin Clinical Study in Dogs with KCS

An open label, single group, pilot efficacy study evaluating topical voclosporin was designed and conducted. The study was intended to document the efficacy of 0.2 wt % voclosporin in a composition according to the presently disclosed embodiments for the treatment of canine keratoconjunctivitis sicca (KCS). The study covered assessment of tear production (as measured by the Schirmer Tear Test (STT)), the response of clinical observation of the cornea, and participating ophthalmologists' overall assessment of efficacy.

Dogs diagnosed with chronic (>3 months in duration) immune-mediated KCS were selected from the clinic populations of the North Carolina State Veterinary Teaching Hospital. Diagnosis of immune-mediated KCS was made by exclusion of other causes of KCS. Dogs selected to be entered into this study had demonstration of residual lacrimal function and have shown response to commercially available topical cyclosporine.

In this study, there was no washout period and animals were switched directly from topical cyclosporine A (0.2% cyclosporine in petrolatum, USP; corn oil, NF; and Amerchol® CAB base (Optimmune® Schering Plough Animal Health)) to 0.2 wt % voclosporin in a mixed micellar composition according to the presently disclosed embodiments, given topically every 12 hours. Physical and ophthalmic examinations were performed at 0, 7, 14, and 28 days. The study was designed such that a favorable response to the voclosporin would be considered a maintenance or increase of STT value compared to pre-study values.

Six dogs were entered and completed the study. For these 6 dogs, the mean STT at day 0 was 21.9±SD 3.2 mm/min; at 7 days of therapy STT was 22.4±4.0 mm/min; at 14 days STT was 20.3±2.5 mm/min, and at 30 days STT was 21.0±1.9 mm/min. This clearly indicates that voclosporin has maintained the STT in these dogs for 30 days. See mean STT values in FIG. 1. All dogs have been comfortable without any signs of side effects or irritation associated with the medication. No adverse effects were noted in any animal during the 30 days treatment period.

Example 14

Robustness and Stability of Formulations

The robustness of a formulation according to the present disclosure containing 0.2 wt % voclosporin was tested by subjecting the samples to multiple heat/cool cycles, refrigeration cycles, vigorous shaking or extended exposure to the sun light.

Thermal Cycling:

A set of glass vials containing formulation were placed in a water bath with temperature set at ~70° C. The samples were heated until the cloudiness appeared and then were cooled at room temperature for the solution to become clear, which constituted one round of thermal cycling. The thermal cycling was repeated 5 or 10 times. After completion of the 5 or 10 thermal cycles, the samples were analyzed for dissociation temperature followed by regeneration time and micellar size determination as described above.

Refrigeration Cycling:

A set of samples were subjected to the refrigerated conditions. The samples were placed in a refrigerator (4° C.) for 12 hours and then brought to room temperature and maintained at room temperature for 12 hours. The thermal cycling was repeated 5 or 10 times. After completion of the 5 or 10 cycles, samples were analyzed for dissociation temperature, followed by regeneration time and micellar size determination as described above.

Vigorous Shaking:

Samples were placed on shaking platform and the shaker was operated at ~75 rpm at room temperature. Samples were withdrawn after 4 hours or 24 hours and analyzed for dissociation temperature, regeneration time and micellar size as described above.

Sunlight Exposure:

Solutions were placed under direct sunlight for 4 hours. Post exposure, the sample were analyzed for dissociation temperature, followed by the regeneration time and micellar size as described above.

The mixed micellar formulation according to the present disclosure containing 0.2 wt % voclosporin was subjected to various stress conditions (heat/cool cycles, refrigeration/ambient cycles, vigorous shaking and exposure to the sun light). The mixed micellar composition according to the presently disclosed embodiments containing 0.2 wt % voclosporin did not exhibit changes in the dissociation temperature, regeneration time and micelle size as shown in Table 32.

TABLE 32

Effect of stress on dissociation temperature, regeneration time and micelle size, average of three replicate samples.

| No | Description of Test | Dissociation temperature (° C.) | Regeneration time (min) | Micellar size (nm) | PDI |
|---|---|---|---|---|---|
| 1 | Samples before subjected to any stress | 54.0 ± 1.0 | 2.5 | 13.3 ± 0.2 | 0.193 ± 0.004 |
| 2 | Samples subjected to 5 cycles of heat/cool | 57.3 ± 0.6 | 3.0 | 16.0 ± 1.6 | 0.198 ± 0.020 |
| 3 | Samples subjected to 10 cycles of heat/cool | 57.0 ± 1.0 | 3.0 | 15.9 ± 1.4 | 0.211 ± 0.10 |
| 4 | Samples subjected to 5 refrigeration/ambient cycles | 55.0 ± 1.0 | 2.6 ± 0.3 | 13.6 ± 0.4 | 0.195 ± 0.011 |
| 5 | Samples subjected to 10 refrigeration/ambient cycles | 55.0 ± 1.7 | 3.0 | 13.3 ± 0.8 | 0.189 ± 0.10 |
| 6 | Samples subjected to 4 hours of shaking on a shaking platform | 54.6 ± 0.6 | 3.0 ± 0.1 | 14.2 ± 0.7 | 0.193 ± 0.008 |
| 7 | Samples subjected to 24 hours of shaking on a shaking platform | 54.6 ± 0.6 | 2.8 ± 0.3 | 14.1 ± 0.4 | 0.193 ± 0.003 |
| 8 | Samples subjected to 4 hours of sun light | 54.6 ± 0.6 | 2.8 ± 0.3 | 13.7 ± 0.4 | 0.194 ± 0.005 |

Stability Study:

Solutions in triplicate were transferred into clean glass vials and stored at different temperatures (45° C., 30° C., RT and 4° C.). At predetermined time intervals (0, 7, 14 and 30 days) samples were withdrawn and assessed for change in color, phase separation, pH, drug content, dissociation temperature, regeneration time and micellar size.

Samples stored at 30° C., RT and 4° C. for up to 30 days did not show changes in color, phase, pH, drug content, dissociation temperature, regeneration time and micellar size. Solutions stored at 45° C. formed precipitates indicating thermal instability of the formulation at high temperatures.

Example 15

Preparation and Micellar Characterization of Formulations Containing Various Calcineurin or mTOR Inhibitors

TABLE 33

Formulations containing various calcineurin and mTOR inhibitors.

| Ingredient | Amount for 100 mL | | |
|---|---|---|---|
| Cyclosporine A | 0.2 g | — | — |
| Sirolimus | — | 0.2 g | — |
| Tacrolimus | — | — | 0.2 g |
| Vitamin E TPGS | 2.5 g | 2.5 g | 2.5 g |
| Octoxynol-40 | 2.0 g | 2.0 g | 2.0 g |
| PVP-K-90 | 1.2 g | 1.2 g | 1.2 g |
| Sodium Phosphate, Dibasic | 0.81 g | 0.81 g | 0.81 g |
| Sodium Phosphate, Monobasic | 0.93 g | 0.93 g | 0.93 g |
| Sodium Chloride | 0.2 g | 0.2 g | 0.2 g |
| Water up to | 100 ml | 100 ml | 100 ml |

Calculated amounts of drug(s), vitamin E TPGS and octoxynol-40 required for 10 mL were weighed, then mixed in 4 mL 95% ethanol, and evaporated under vacuum to form a thin film near-solid matter. The thin film near-solid matter was then dissolved in 5 mL deionized water and sonicated approximately 40 minutes to ensure complete formation of mixed micelles. The prepared basic formulations were stored at room temperature.

A buffer mixture containing sodium phosphate, dibasic, sodium phosphate, monobasic and sodium chloride was prepared by dissolving in deionized water. Stock solution PVP-K-90 was prepared in water. The required volume of polymer solution and buffer solution was added to the basic formulations and gently vortexed to get a clear solution. The pH of the solution was adjusted with NaOH or HCl to a target of about 6.8. The formulation was sterilized by a nylon membrane filter (0.22 μm) and then stored at room temperature until use. The micellar size of formulations was measured by using dynamic light scattering technique (Brookhaven 90Plus particle size analyzer, Holtsville, N.Y.), taking the average of three measurements. The results of the study are described below. The formulations were found to be clear and transparent at room temperature. The micellar size and polydispersity (PDI) index of the formulations are given in Table 34.

TABLE 34

Observed micelle size and PDI of the formulations

| Formulation containing | Micelle Size (nm) | PDI |
|---|---|---|
| Cyclosporine | 12.6 ± 0.2 | 0.119 ± 0.004 |
| Sirolimus | 13.9 ± 0.1 | 0.198 ± 0.002 |
| Tacrolimus | 13.8 ± 0.2 | 0.199 ± 0.005 |

Example 16

Artificial Tear Compositions

TABLE 35

Biocompatible Artificial Tear Composition

| Ingredient | Amount |
|---|---|
| Voclosporin | 0 |
| Vitamin E TPGS | 2.5 g |
| Octoxynol-40 | 2.0 g |
| PVP-K-90 | 1.2 g |
| Sodium Phosphate, Dibasic | 0.81 g |

TABLE 35-continued

Biocompatible Artificial Tear Composition

| Ingredient | Amount |
|---|---|
| Sodium Phosphate, Monobasic | 0.93 g |
| Sodium Chloride | 0.2 g |
| Water up to | 100 mL |

To show that none of the components of the artificial tear compositions of the present disclosure are inherently irritating to ocular tissues, a study was performed to determine ocular tolerability and toxicity of the artificial tears.

New Zealand White (NZW) rabbits (5 female/5 male) were topically administered one approximately 35 μl drop or the artificial tear composition of the present disclosure to each eye at 1 hour intervals, for a maximum of up to 8 times per day. Animals were sacrificed following 14 days of artificial tear administration. The following parameters were evaluated during the study: morbidity/mortality, physical examination, clinical observations, body weights, feed consumption, macro- and microscopic ocular observations, electroretinography (ERG), intraocular pressure measurement (IOP), and upon necropsy, histopathology was performed on the following tissues: eyes, thymus, mandibular, rostral and caudal lymph nodes, spleen. All animals were healthy and showed no findings outside the normal range. Eye related examination reports are provided in further details below:

Microscopic Ocular Grading:

The microscopic ocular grading system was applied to ocular findings following use of the slit lamp biomicroscope which included insertion of a blue filter to assess for fluorescein dye retention. No lesions were noted by indirect ophthalmoscopy performed pre-dose, and after 14 days of artificial tear composition application (8 times per day).

Tonometry (IOP) Data Observations:

Mean tonometry (Tono-pen) readings of intraocular pressures (IOPs) in rabbits performed pre-test and after 14 days of artificial tear composition application were between 11-17 mm/Hg pressure and were within the normal physiologic range (10-20/mm Hg). In conclusion, no IOP effects were observed in association with topical treatments administered (8 times per day).

ERG Data Observations:

Bilateral full-field flash ERGs were performed in rabbits utilizing the ISCEV protocol and the HMsERG unit. Preliminary evaluation of maximum a- and b-wave amplitudes for high intensity stimulation with 10 cd·s/m2, and 30 Hz flicker stimulation, also using 10 cd·s/m2, both under scotopic conditions, did not show any findings after 14 days of artificial tear composition application (8 times per day).

Histopathology Observations

There were no histopathologic findings after 14 days of artificial tear composition application (8 times per day)

Example 17

Mixed Micellar Formulations Containing Sugar Additives

Sugar additives, such as trehalose, mannose, D-galactose and lactose were added to the various formulations of the present disclosure and stability studies were carried out at different temperatures. Sugars were added to the formulations during the rehydration step (externally), or added prior to the creation of the thin-film (internally). The formulations were found to be stable in the presence of the adjuvant sugars.

Formulations containing decreased concentration of octoxynol-40 with sugar were also prepared where sugar was added during the preparation of basic formulation (internally). Studies were carried out with 0.05% and 0.1% octoxynol-40 and 0.5% and 1.0% sugar for stability studies. The results obtained during the studies showed that the formulation remained stable until 35 days at 30° C.

TABLE 36

Compositions of formulations (sugars added internally).

| Voclosporin | 0.2% | 0.2% | 0.2% | 0.2% |
|---|---|---|---|---|
| Vitamin E TPGS | 2.5 | 2.5 | 2.5 | 2.5 |
| Octoxynol-40 | 0.05% | 0.1% | 0.05% | 0.1% |
| Trehalose | 0.5% | 0.5% | 1.0% | 1.0% |
| Water up to | 100 ml | 100 ml | 100 ml | 100 ml |

Method:

Calculated amounts of drug (about 0.2%, i.e., 200 mg), vitamin E TPGS (about 2.5%, i.e., 2.5 g) and octoxynol-40 (about 0.05/0.1%, i.e., 50/100 mg) required for 100 mL of the formulation were weighed. Two hundred milligrams of drug, about 2.5 g of TPGS and about 50/100 mg of octoxynol-40 were dissolved in about 2 ml, about 1 ml and about 50/100 μL of 95% ethanol, respectively. For sugar, about 1 g of trehalose was dissolved in about 4.5 ml of water/ethanol mixture (about 2.5 ml water+about 2.0 ml ethanol) separately and mixed with other contents. Same water:ethanol ratio was used for preparing formulations containing different amounts of sugar. The mixture was then evaporated under vacuum overnight to form a thin film. The thin film was then dissolved in about 45 mL deionized water and sonicated for approximately 45 min to ensure complete formation of mixed micelles.

The rehydrating solution containing sodium phosphate, dibasic (about 0.8092%), sodium phosphate, monobasic (about 0.9287%), sodium chloride (about 0.18%) and the polymer PVP-K 90 (about 1.2%) was prepared by dissolving amounts in about 45 mL of deionized water. This polymer solution was then added to the previously prepared micelles in a measuring cylinder and the volume was made up to about 100 mL with de-ionized water (q.s.). Finally the pH of the formulation was adjusted with NaOH or HCl to about 6.8. The formulation was sterilized by a nylon membrane filter (0.22 μm).

During stability studies, at predetermined time intervals samples were withdrawn, centrifuged and the supernatant solution was collected for analysis of drug content.

Results:

The formulations were found to be clear and transparent at room temperature before the start of stability studies. Micellar size observed was in the range of 12-14 nm. Example formulations with octoxynol-40 and trehalose are as follows:

TABLE 37A

Formulations with sugar additives.

| Code | Formulation Label |
|---|---|
| B | 0.05% OC-40 + 0.5% trehalose |
| C | 0.1% OC-40 + 0.5% trehalose |
| E | 0.05% OC-40 + 1.0% trehalose |
| F | 0.1% OC-40 + 1.0% trehalose |

TABLE 37B

Percentage drug remaining of different formulations at 30° C.

| | \multicolumn{9}{c}{Day} |
|---|---|---|---|---|---|---|---|---|---|
| | 0 | 2 | 4 | 6 | 8 | 13 | 18 | 25 | 35 |
| B | 100.00 | 103.11 | 98.26 | 98.20 | 98.72 | 101.59 | 98.85 | 107.14 | 95.40 |
| C | 100.00 | 98.43 | 94.55 | 95.50 | 96.66 | 98.65 | 94.88 | 93.84 | 95.21 |
| E | 100.00 | 96.37 | 97.22 | 99.04 | 97.61 | 99.38 | 95.88 | 93.12 | 91.75 |
| F | 100.00 | 99.54 | 98.33 | 100.33 | 99.00 | 100.97 | 95.11 | 95.79 | 97.27 |

Example 18

Ocular Distribution and Pharmacokinetics of 0.2 wt %/vol. Voclosporin in Mixed Micellar Formulations of the Present Disclosure The purpose of this study was to assess the temporal distribution and potential accumulation with repeat dosing, gender difference, and potential melanin binding of a 0.2% $^{14}$C-radiolabeled voclosporin composition (ophthalmic solution) of the present disclosure after ocular application by determining radioactivity in ocular tissues, tears, and blood in New Zealand White (NZW) and Dutch Belted (DB) rabbits.

Methods:

NZW rabbits (30 females/8 males) were used in a single dose (SD) and 7-day repeat dose (RD) study (see Table 38). DB rabbits (16 females) were used in a single dose study (see Table 39). Animals were either not treated (controls) or given a single or a daily topical ocular dose for 7 days (35 µL of 0.2% $^{14}$C-voclosporin in a mixed micellar formulation to one or both eyes). Blood and ocular tissue radioactivity levels were assessed at designated time points via combustion followed by liquid scintillation counting. No mortality, morbidity or evidence of clinical irritation occurred in any of the rabbits.

TABLE 38

Ocular Tissue Distribution of $^{14}$C-Voclosporin in Mixed Micellar Composition.

| Group ID | No. of Animals/group | $^{14}$C-Dose Administration[a] | Matrices Collected | Sample Collection Time (Time of euthanasia) |
|---|---|---|---|---|
| 1[b] | 2 ♀ 2 ♂ | None | Tear, Blood, Ocular Tissues/Fluids | Pre-dose |
| 2[c] | 12 ♀ 6 ♂ | 35 µL/eye, once, Ocular (bilateral) | Tear, Blood, Ocular Tissues/Fluids (SD group) | ♀: 0.5, 1, 2, 4, 8, and 24 hr ♂: 1, 4, and 24 hr After the dose administration (2 animals/time point) |
| 3 | 2 ♀ | 35 µL/eye, once, Ocular (unilateral) | Tear, Blood, Ocular Tissues/Fluids | 1 hr after the dose administration |
| 4[d] | 2 ♀ | 35 µL/eye, once daily, bilateral for 6 days | Tear, Blood Ocular Tissues/Fluids | Just prior to 7$^{th}$ dose administration in the next group |
| 5[e] | 12 ♀ | 35 µL/eye, once daily, bilateral for 7 days | Tear, Blood Ocular Tissues/Fluids (RD group) | 0.5, 1, 2, 4, 8, and 24 hr after the last dose administration (2 animals/time point) |

[a]The topical dose formulation contained 0.2% voclosporin. The target dose was ~3 µCi/35 µL and 70 ng voclosporin.
[b]Used as predose concentration for Treatment Group 2 (SD group).
[c]Used for pharmacokinetic assessment (SD group).
[d]Used as predose concentration for Treatment Group 5 (RD group).
[e]Used for pharmacokinetic assessment (MD group).

TABLE 39

Ocular Tissue Distribution of $^{14}$C-voclosporin in Mixed Micellar Composition

| Group ID | No. of Animals/group | $^{14}$C-Dose Administration[a] | Matrices Collected | Sample Collection Time (Time of Euthanasia) |
|---|---|---|---|---|
| 1[b] | 2 ♀ | None | Tear, Blood, Ocular Tissues/Fluids | Pre-dose |
| 2[c] | 12 ♀ | 35 µL/eye, once, Ocular (bilateral) | Tear, Blood, Ocular Tissues/Fluids (SD group) | 0.5, 1, 2, 4, 8, and 24 hr after the dose administration (2 animals/time point) |
| 3 | 2 ♀ | 35 µL/eye, once, Ocular (unilateral) | Tear, Blood, Ocular Tissues/Fluids | 1 hr after dose administration |

[a]The topical dose formulation contained 0.2% voclosporin. The target dose was ~3 µCi/35 µL and 70 ng voclosporin/dose.
[b]Used as predose concentration for Treatment Group 2 (SD group).
[c]Used for pharmacokinetic assessment (SD group).

At each sampling point, a t-test was used to compare the tissue concentrations within or between the two strains of rabbits. SigmaStat® 3.5 (Systat, Inc., San Jose, Calif.) was used for the statistical analyses (p<0.05). Non-compartmental analysis was performed on the mean tissue $^{14}$C-voclosporin concentration-time data. Pharmacokinetic analysis $t_{1/2}$ (see Table 40). All but one blood sample were below the lower limit of quantification (LLOQ) (3.06 ng eq/mL) in the radioactivity assay. Notably, single dose administration resulted in therapeutic levels (higher than 10 ng equivalent drug/gram tissue) in all ocular tissues (with the exception of aqueous/vitreous humor and lens), with negligible systemic exposure.

TABLE 40

Pharmacokinetic Parameters of $^{14}$C-voclosporin-derived radioactivity following a single or repeat (QD for 7 days), bilateral ocular administration of $^{14}$C-voclosporin in a mixed micellar formulation to female NZW rabbits.

| Ocular Tissue(s)/Fluids & Blood | $C_{max}$ (ng eq./g) | | | AUC (hr * ng eq./g) | | | $T_{max}$ (hr) | | $t_{1/2}$ (hr) | |
|---|---|---|---|---|---|---|---|---|---|---|
| | SD | RD | Ratio | SD | RD | Ratio | SD | RD | SD | RD |
| Aqueous Humor | 6 | 13 | 2.3 | 45 | 96 | 2.1 | 0.5 | 0.5 | — | 14 |
| Choroid/Retina | 48 | 76 | 1.6 | 472 | 897 | 1.9 | 1.0 | 2.0 | 23 | — |
| Cornea | 1203 | 3382 | 2.8 | 23166 | 54624 | 2.4 | 8.0 | 0.5 | — | — |
| Iris/Ciliary Body | 20 | 119 | 5.8 | 382 | 1952 | 5.1 | 24.0 | 1.0 | — | — |
| Lacrimal Gland | 31 | 120 | 3.9 | 416 | 1109 | 2.7 | 2.0 | 4.0 | — | 6 |
| Lens | 4 | 26 | 6.7 | 47 | 356 | 7.5 | 24.0 | 0.5 | — | — |
| Lower Bulbar Conjunctiva | 1810 | 2929 | 1.6 | 12029 | 16585 | 1.4 | 0.5 | 0.5 | 10 | 7 |
| Lower Eyelid | 20814 | 41635 | 2.0 | 207630 | 358791 | 1.7 | 1.0 | 0.5 | — | — |
| Nictitating Membrane | 1716 | 2468 | 1.4 | 12135 | 15964 | 1.3 | 0.5 | 0.5 | 7 | 8 |
| Optic Nerve | 83 | 164 | 2.0 | 569 | 1805 | 3.2 | 0.5 | 0.5 | — | 16 |
| Sclera | 223 | 367 | 1.6 | 2646 | 3825 | 1.4 | 0.5 | 0.5 | — | 16 |
| Submandibular Lymph Node | 74 | 120 | 1.6 | 893 | 1190 | 1.3 | 2.0 | 2.0 | — | — |
| Tear | 20246 | 30904 | 1.5 | 168259 | 230878 | 1.4 | 0.5 | 0.5 | — | 7 |
| Upper Bulbar Conjunctiva | 2235 | 3170 | 1.4 | 14782 | 19944 | 1.3 | 0.5 | 0.5 | 7 | 7 |
| Upper Eyelid | 9896 | 17500 | 1.8 | 114651 | 98656 | 0.9 | 1.0 | 0.5 | — | 4 |
| Vitreous Humor | 2 | 2 | 1 | 27 | 23 | 0.9 | 8.0 | 4.0 | — | — |
| Blood | BQL | BQL | NC | NC | NC | NC | NC | NC | NC | NC |

SD = Single dose;
RD = Repeat Dose;
Ratio = Repeat Dose/Single Dose.;
— = Insufficient tissue concentrations to determine $t_{1/2}$;
BQL = Below Quantifiable Limit (<0.1 ng/mL);
NC = Not calculated.

was performed using WinNonlin 5.2 (Pharsight, Corporation, Mountain View, Calif.). $C_{max}$ and $T_{max}$, and where calculable AUC and $t_{1/2}$, were reported.

Figure 2:
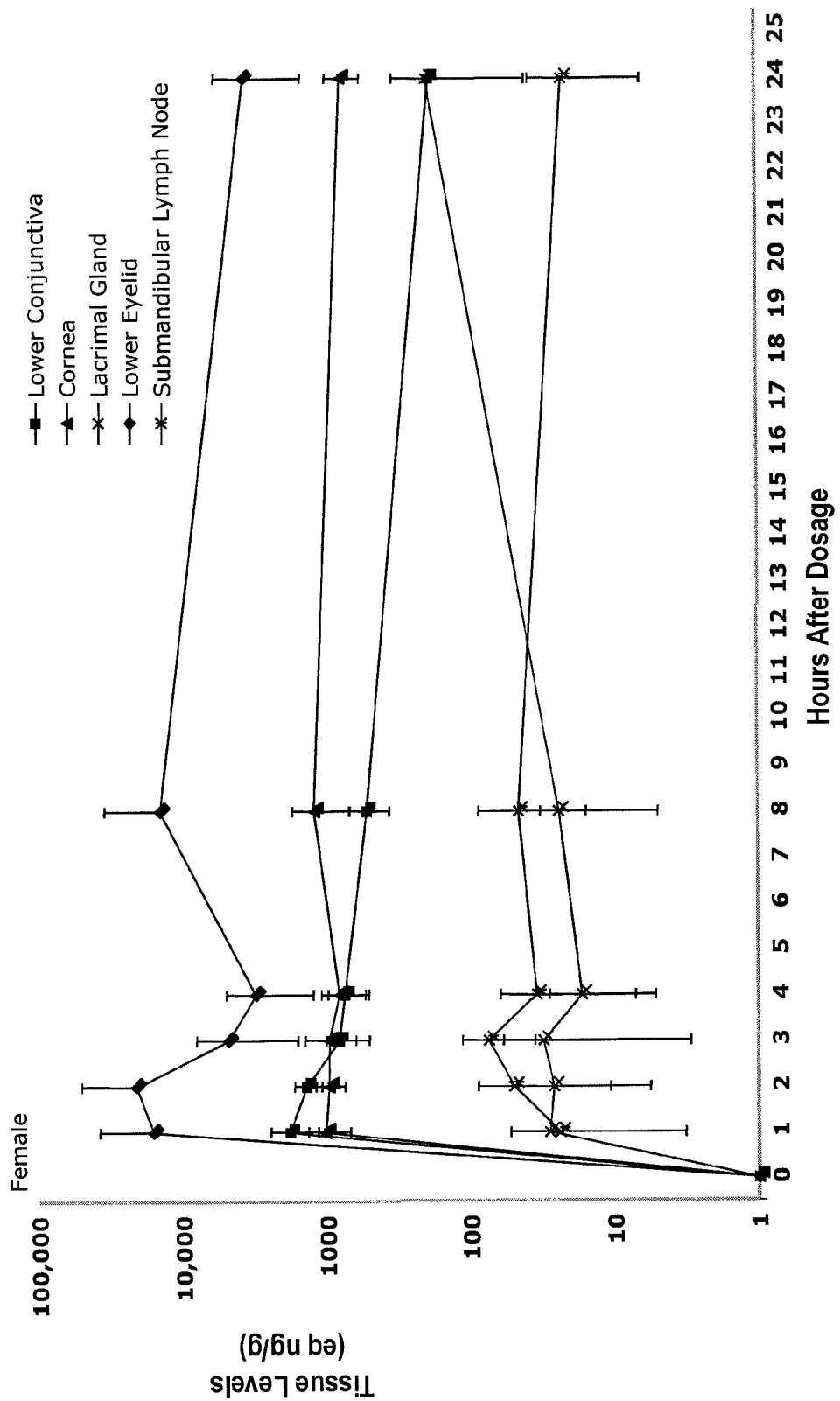
FIG. 2 shows tissue levels of voclosporin after a single (1 day) topical dose of a mixed micellar pharmaceutical composition of the presently disclosed embodiments having $^{14}$C-voclosporin to female New Zealand White Rabbits. Therapeutic levels of voclosporin were noticed even at the 24-hour mark, supporting once daily (QD) dosing is possible with the aqueous mixed micellar composition of the presently disclosed embodiments. The experiment included male rabbits also with similar result (data not shown).

Pharmacokinetic Parameters:

Selected pharmacokinetic parameters ($C_{max}$, AUC, $T_{max}$, and $t_{1/2}$) for $^{14}$C-voclosporin-derived radioactivity are summarized in Tables 40 and 41 for NZW and DB rabbits, respectively. After a single dose, there was rapid penetration of drug (measured as radioactivity) into ocular tissues with the highest concentrations (>1 mg eq/g tissue) occurring in the eyelids, conjunctiva, cornea, nictitating membrane and tears, and the lowest concentrations (1-11 ng eq/g tissue) in the aqueous and vitreous humor, and the lens. The remaining ocular tissues achieved various levels (20-223 ng eq/g tissue) of voclosporin and/or related residue. FIG. 2 shows the tissue levels of $^{14}$C-voclosporin after a single (1 day) topical dose of the 0.2% $^{14}$C-voclosporin mixed micellar formulation to female New Zealand White Rabbits. Therapeutic levels of voclosporin were noticed at the 24-hour mark, supporting once daily (QD) dosing is possible with the aqueous mixed micellar composition of the presently disclosed embodiments.

Following repeat dosing of up to 7 days, based on limited available information generated in this study (lower bulbar conjunctiva, nictitating membrane, and upper bulbar conjunctiva), there was no apparent change in $^{14}$C-voclosporin

TABLE 41

Pharmacokinetic Parameters of $^{14}$C-voclosporin-derived radioactivity following a single bilateral ocular administration of $^{14}$C-voclosporin in a mixed micellar formulation according to the present disclosure to female DB Rabbits.

| Ocular Tissue(s)/Fluids & Blood | $C_{max}$ (ng eq./g) | $T_{max}$ (hr) | $t_{1/2}$ (hr) | AUC (hr * ng eq./g) |
|---|---|---|---|---|
| Aqueous Humor | 11 | 0.5 | — | 56 |
| Choroid/Retina | 49 | 1.0 | — | 92 |
| Cornea | 1519 | 8.0 | — | 27844 |
| Iris/Ciliary Body | 30 | 24.0 | — | 541 |
| Lacrimal Gland | 75 | 1.0 | — | 335 |
| Lens | 2 | 24.0 | — | 26 |
| Lower Bulbar Conjunctiva | 2080 | 1.0 | 15 | 13107 |
| Lower Eyelid | 69055 | 4.0 | — | 512473 |
| Nictitating Membrane | 2400 | 1.0 | 12 | 13091 |
| Optic Nerve | 192 | 1.0 | 16 | 1127 |
| Sclera | 220 | 1.0 | — | 3502 |
| Submandibular Lymph Node | 86 | 4.0 | — | 635 |
| Tear | 57476 | 1.0 | — | 262299 |
| Upper Bulbar Conjunctiva | 2491 | 1.0 | 14 | 14296 |
| Upper Eyelid | 8245 | 4.0 | — | 68063 |
| Vitreous Humor | 1 | 1.0 | — | 16 |
| Blood | BQL | NC | NC | NC |

TABLE 42

Comparative $C_{max}$ of $^{14}$C-voclosporin derived radioactivity in NZW and DB rabbits after single topical ocular administration of $^{14}$C-voclosporin.

| Ocular Tissue(s)/Fluids & Blood | New Zealand White (Study No. S08861) $C_{max}$ (ng eq./g) | Dutch Belted (Study No. S08862) $C_{max}$ (ng eq./g) |
|---|---|---|
| Aqueous humor | 6 | 11 |
| Choroid/Retina | 48 | 49 |
| Cornea | 1203 | 1519 |
| Iris/Ciliary Body | 20 | 30 |
| Lacrimal Gland | 31 | 75 |
| Lens | 4 | 2 |
| Lower Bulbar Conjunctiva | 1810 | 2080 |
| Lower Eyelid | 20814 | 69055 |
| Nictitating membrane | 1716 | 2400 |
| Optic Nerve | 83 | 192 |
| Sclera | 223 | 220 |
| Submandibular Lymph Node | 74 | 86 |
| Tear | 20246 | 57476 |
| Upper Bulbar Conjunctiva | 2235 | 2491 |
| Upper Eyelid | 9896 | 8245 |
| Vitreous Humor | 2 | 1 |
| Blood | BQL | BQL |

TABLE 43

Ocular tissues/fluids distribution ($C_{max}$) of $^{14}$C-voclosporin in NZW Rabbits.

| Ocular Tissue(s)/Fluids & Blood | $^{14}$C-voclosporin (0.2%, $^{14}$C-voclosporin aqueous solution) Single dose $C_{max}$ (ng eq./g)$^a$ | Once a day (QD) 7 Days $C_{max}$ (ng eq./g)$^a$ |
|---|---|---|
| Aqueous humor | 6 | 13 |
| Choroid/Retina | 48 | 76 |
| Cornea | 1203 | 3382 |
| Iris/Ciliary Body | 20 | 119 |
| Lacrimal Gland | 31 | 120 |
| Lens | 4 | 26 |
| Lower Conjunctiva | 1810 | 2929 |
| Lower Eyelid | 20814 | 41635 |
| Nictitating membrane | 1716 | 2468 |
| Optic Nerve | 83 | 164 |
| Sclera | 223 | 367 |
| Submandibular Lymph Node | 74 | 120 |
| Tear | 20246 | 30904 |
| Upper Conjunctiva | 2235 | 3170 |
| Upper Eyelid | 9896 | 17500 |
| Vitreous Humor | 2 | 2 |
| Blood | BQL | BQL |

Figure 3A:
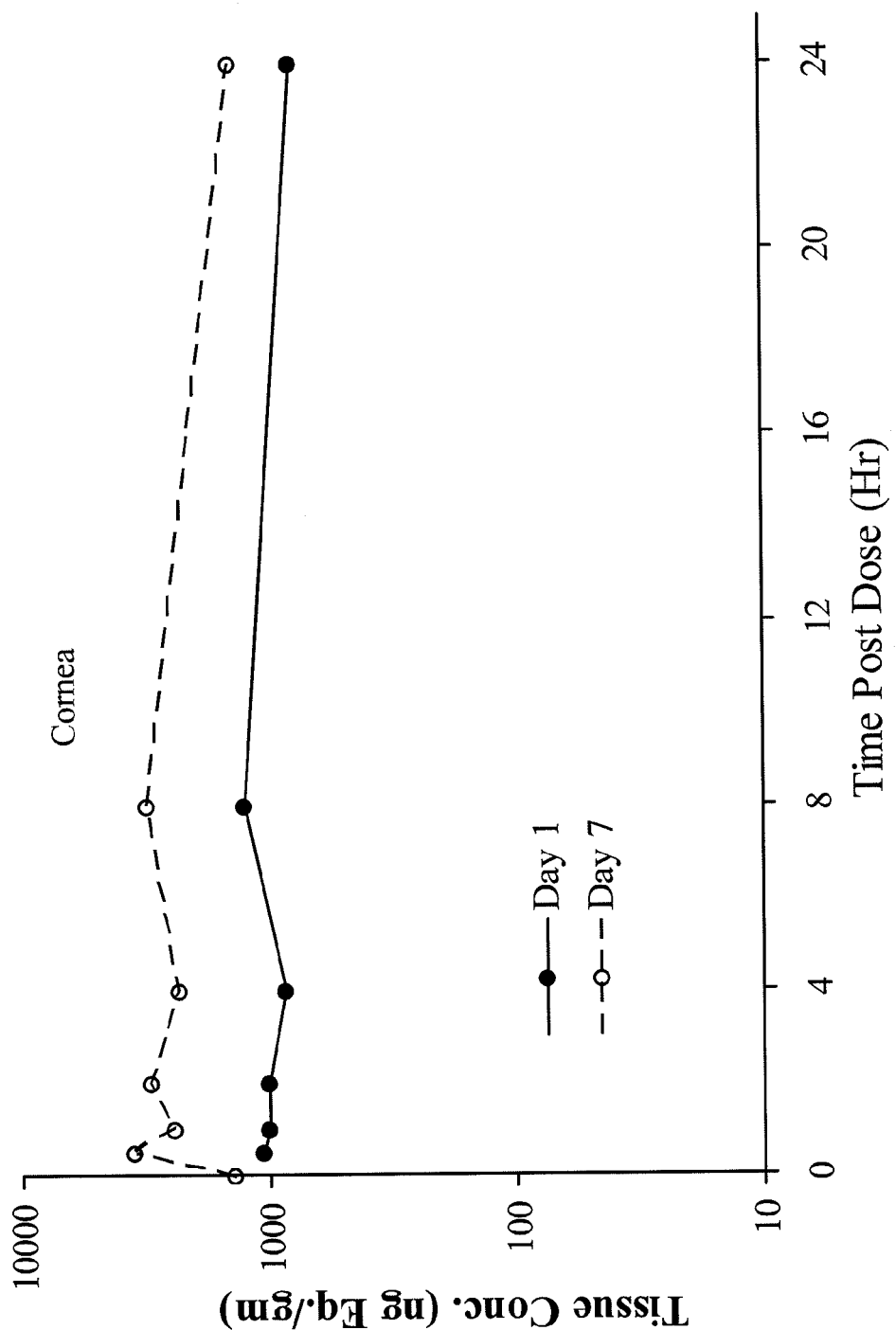
FIGS. 3A-D show mean ocular tissue concentrations of voclosporin after a single (1 day) or repeat (7 days), bilateral, once daily, topical dose of a mixed micellar pharmaceutical composition of the presently disclosed embodiments having $^{14}$C-voclosporin to female New Zealand White Rabbits.
Figure 3B:
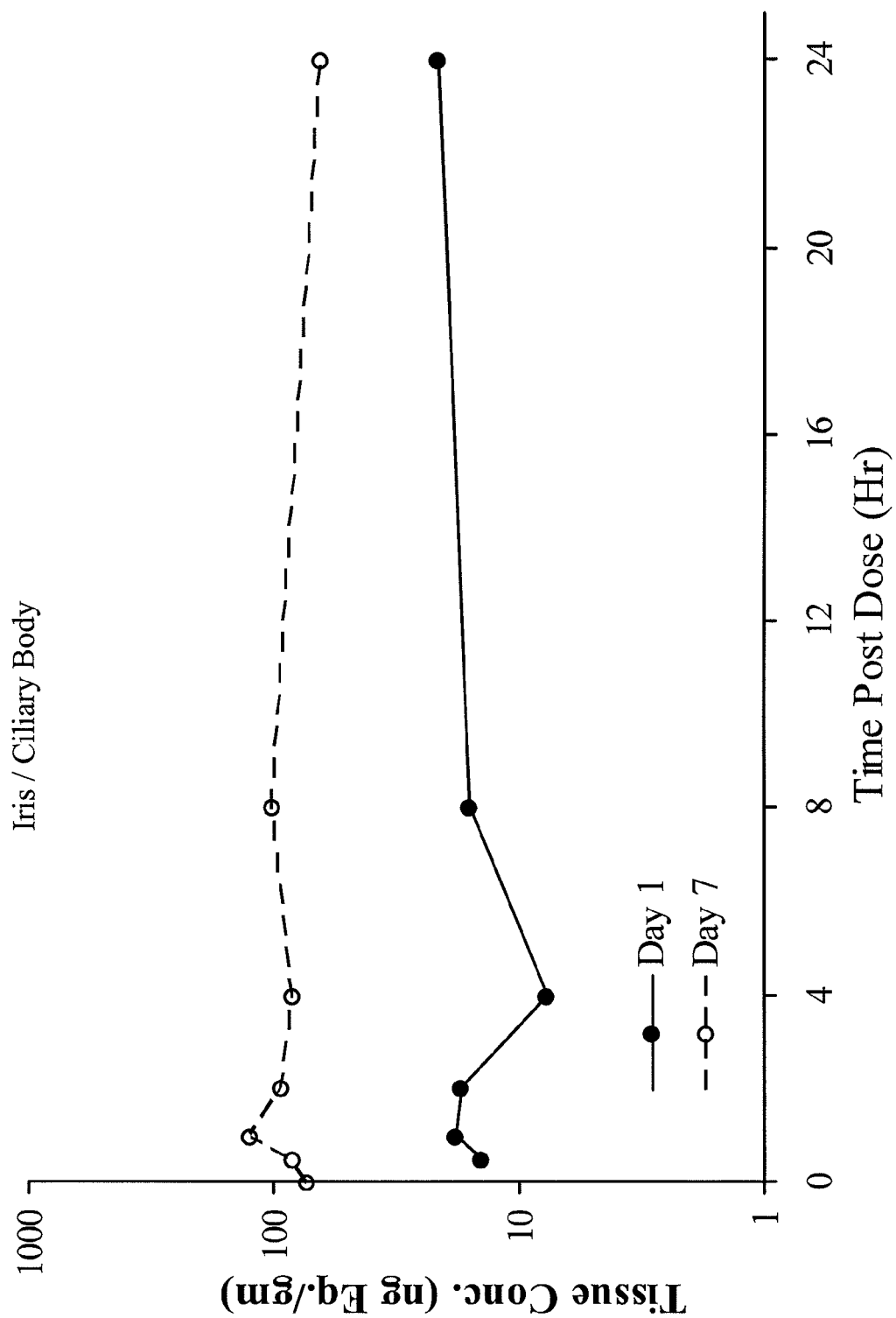
Figure 3C:
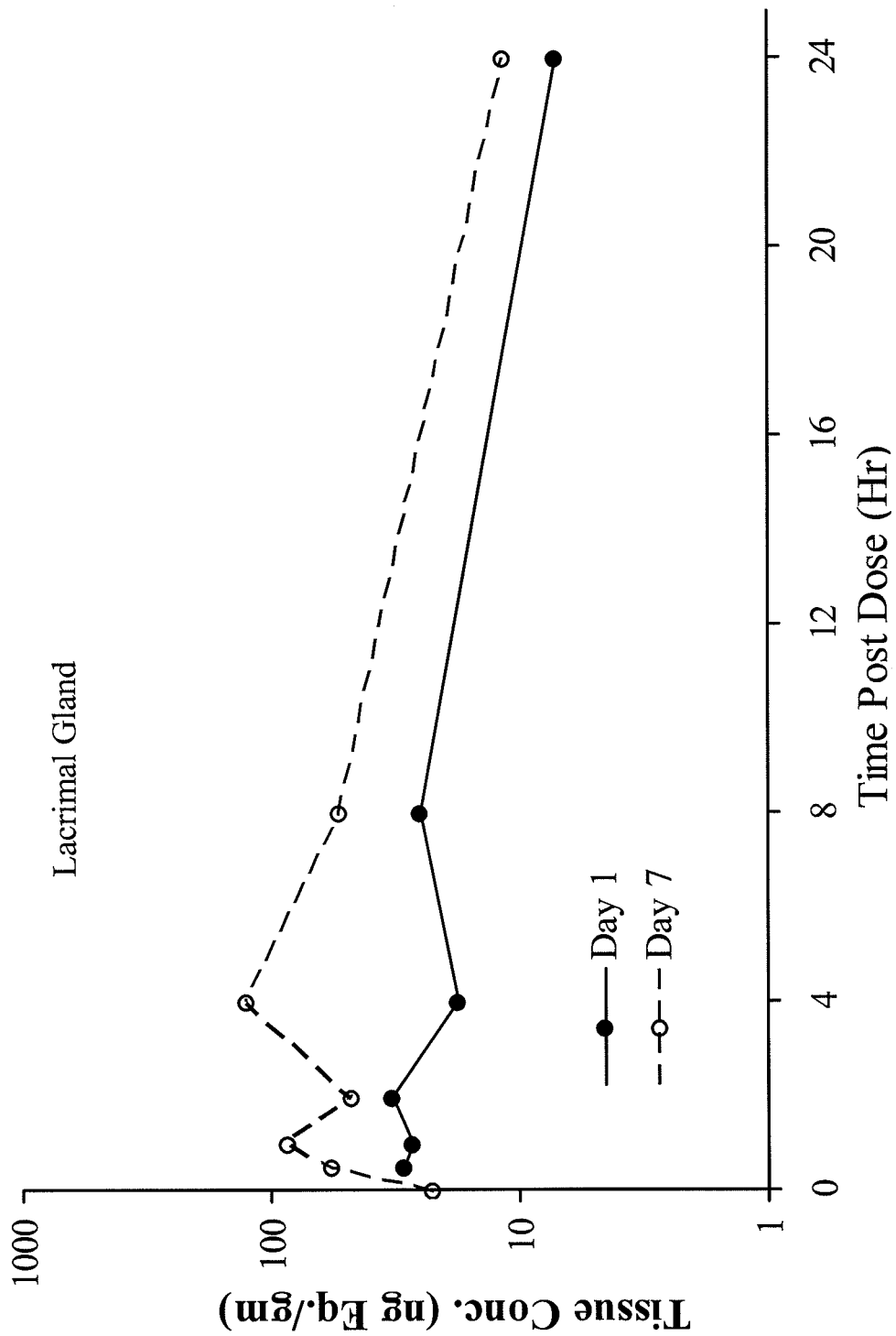
Figure 3D:
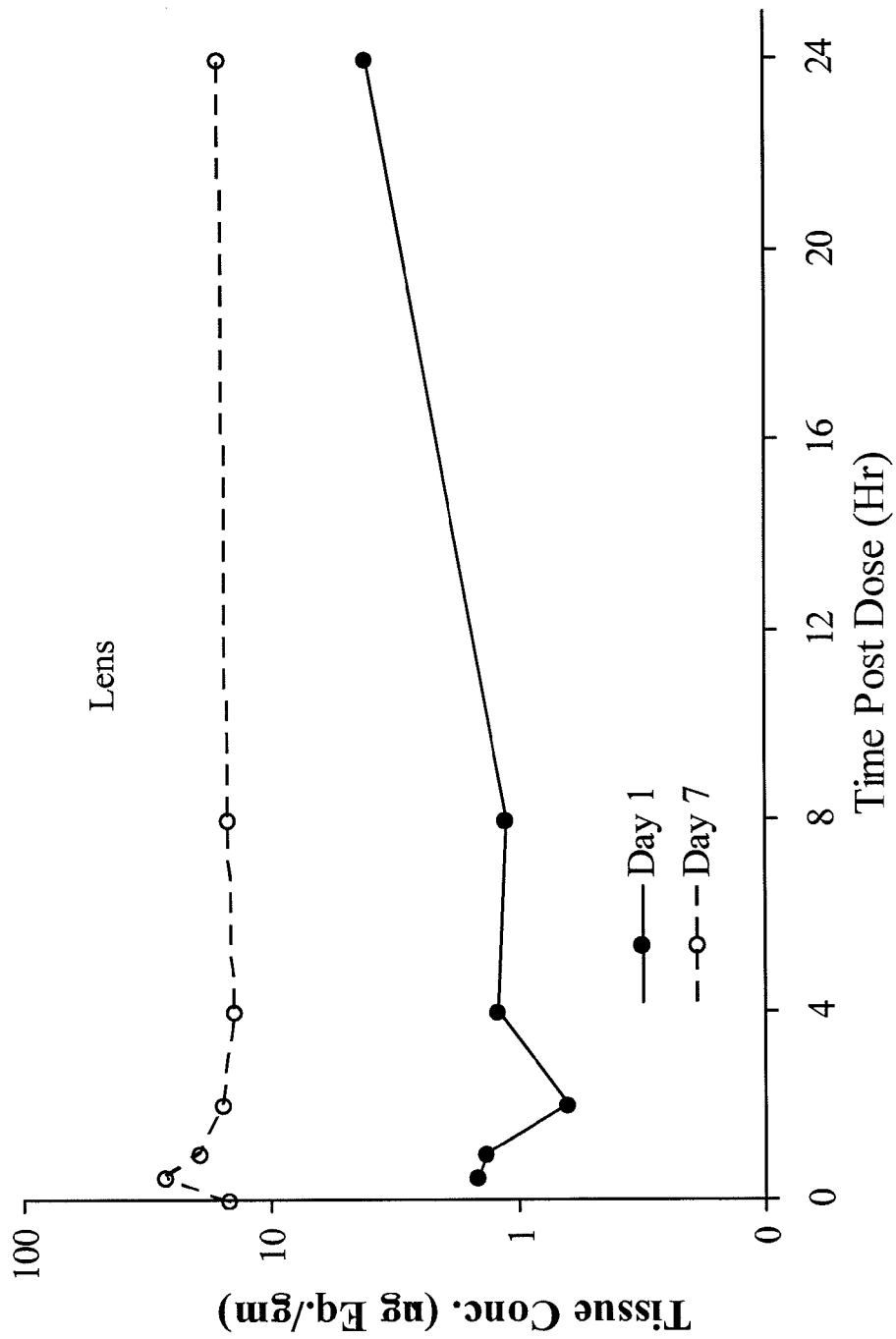

FIGS. 3A-D show mean ocular tissue concentrations of $^{14}$C-voclosporin after a single (1 day) or repeat (7 days), bilateral, once daily, topical dose of the 0.2% $^{14}$C-voclosporin mixed micellar formulation to female New Zealand White Rabbits (FIG. 3A, cornea; FIG. 3B, iris/ciliary body; FIG. 3C, lacrimal gland; and FIG. 3D, lens).

Figure 4A:
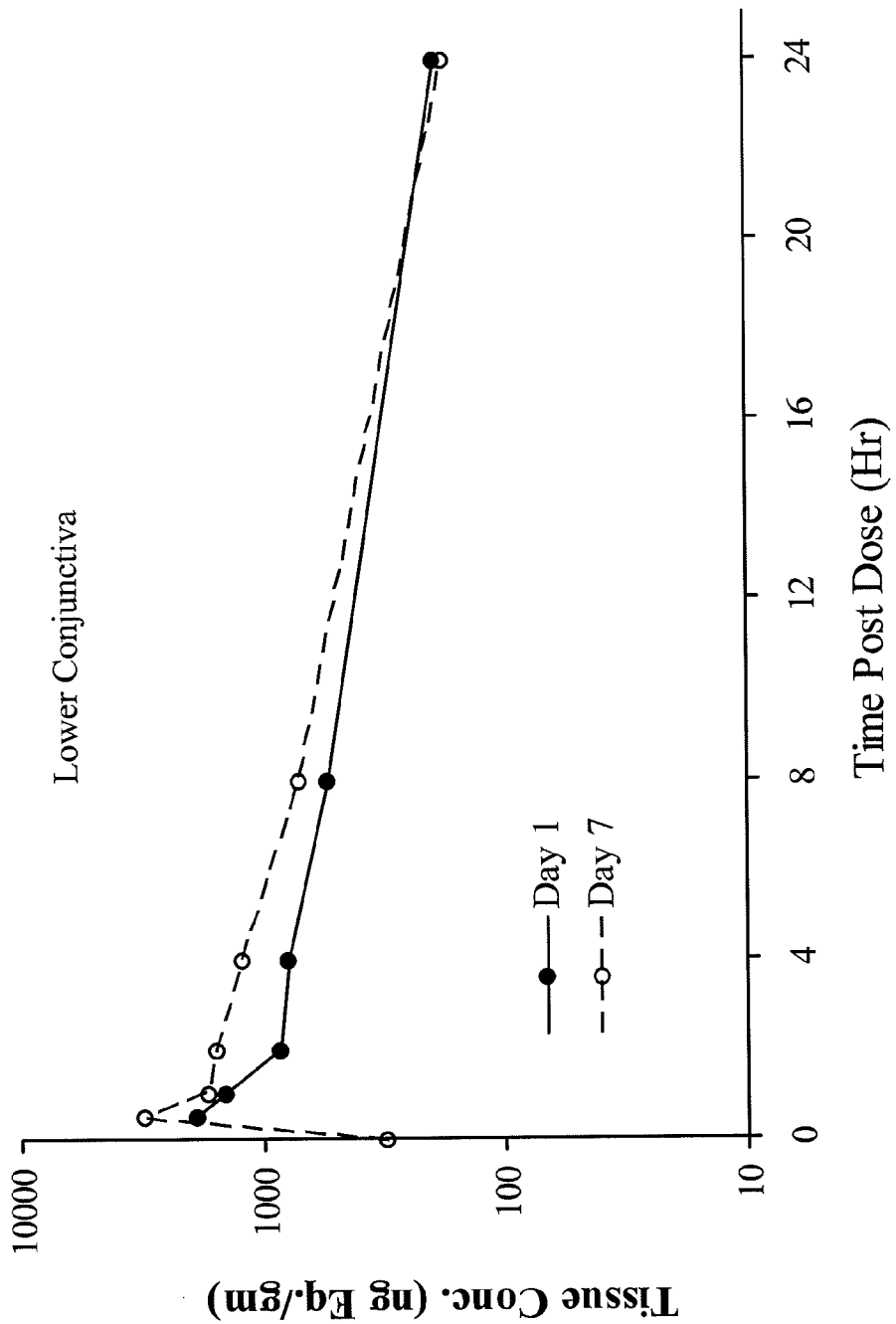
FIGS. 4A-D show mean ocular tissue concentrations of voclosporin after a single (1 day) or repeat (7 days), bilateral, once daily, topical dose of a mixed micellar pharmaceutical composition of the presently disclosed embodiments having $^{14}$C-voclosporin to female New Zealand White Rabbits.
Figure 4B:
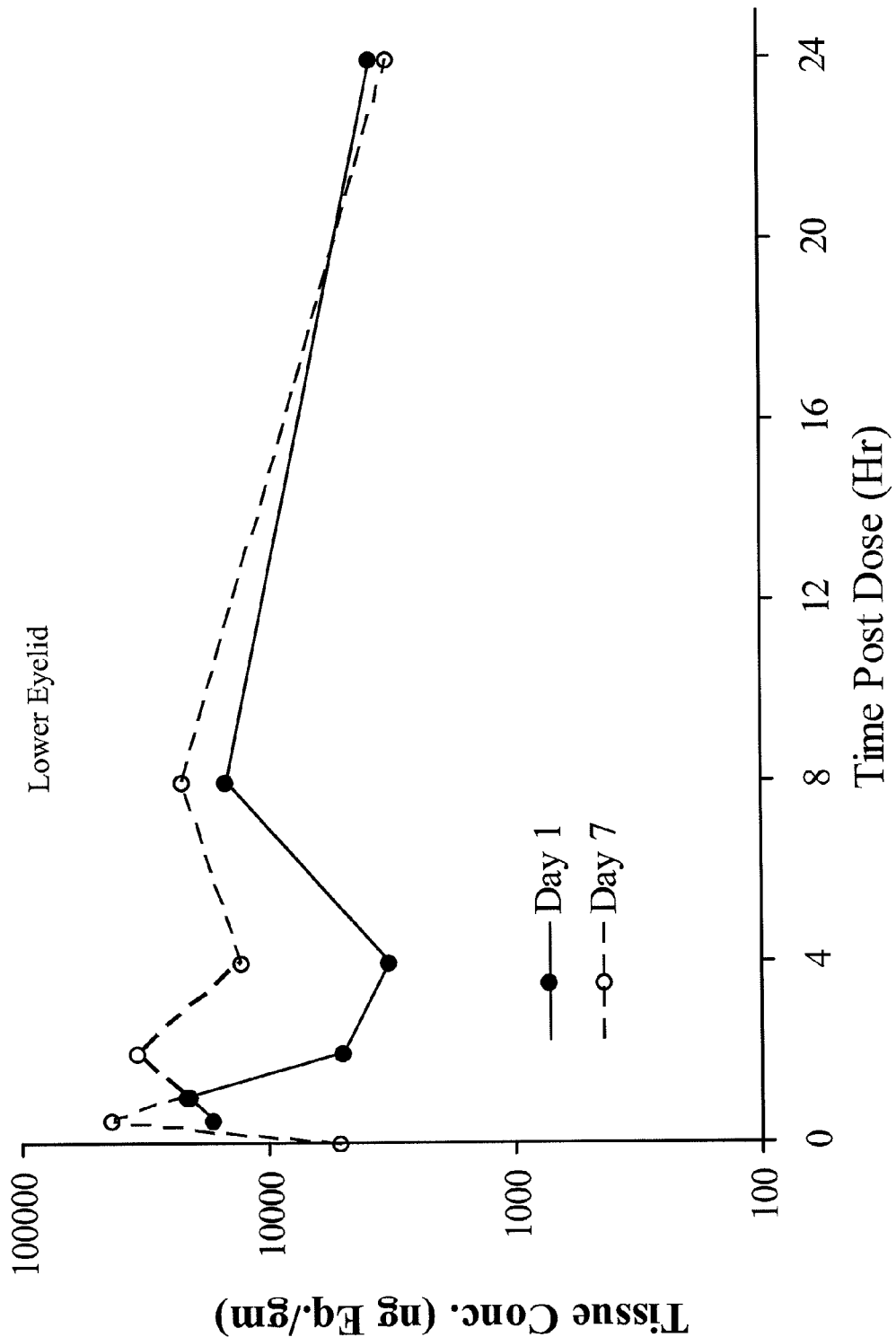
Figure 4C:
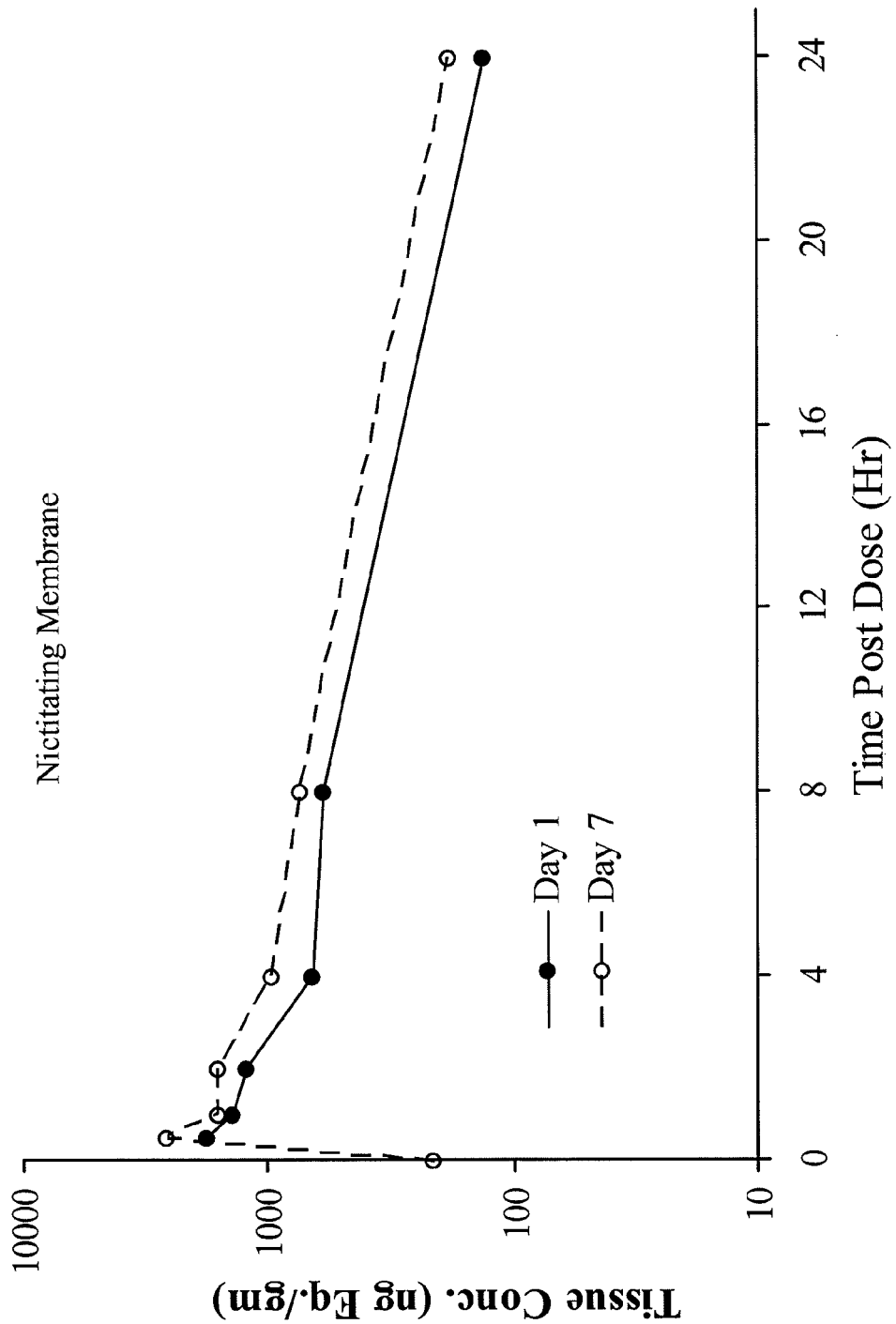
Figure 4D:
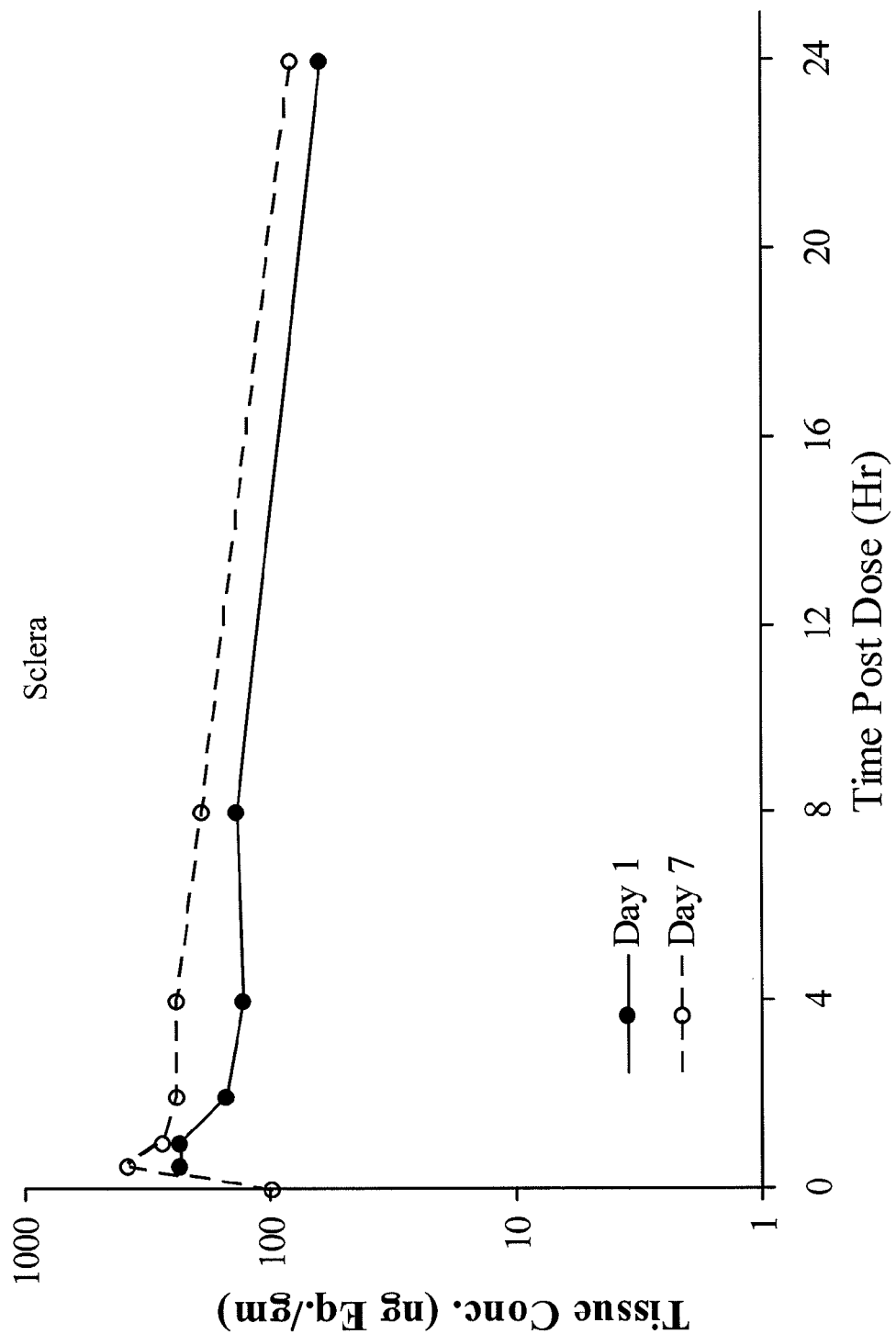

FIGS. 4A-D show mean ocular tissue concentrations of $^{14}$C-voclosporin after a single (1 day) or repeat (7 days), bilateral, once daily, topical dose of the 0.2% $^{14}$C-voclosporin mixed micellar formulation to female New Zealand White Rabbits (FIG. 4A, lower conjunctiva; FIG. 4B, lower eyelid; FIG. 4C, nictitating membrane; and FIG. 4D, sclera).

Figure 5A:
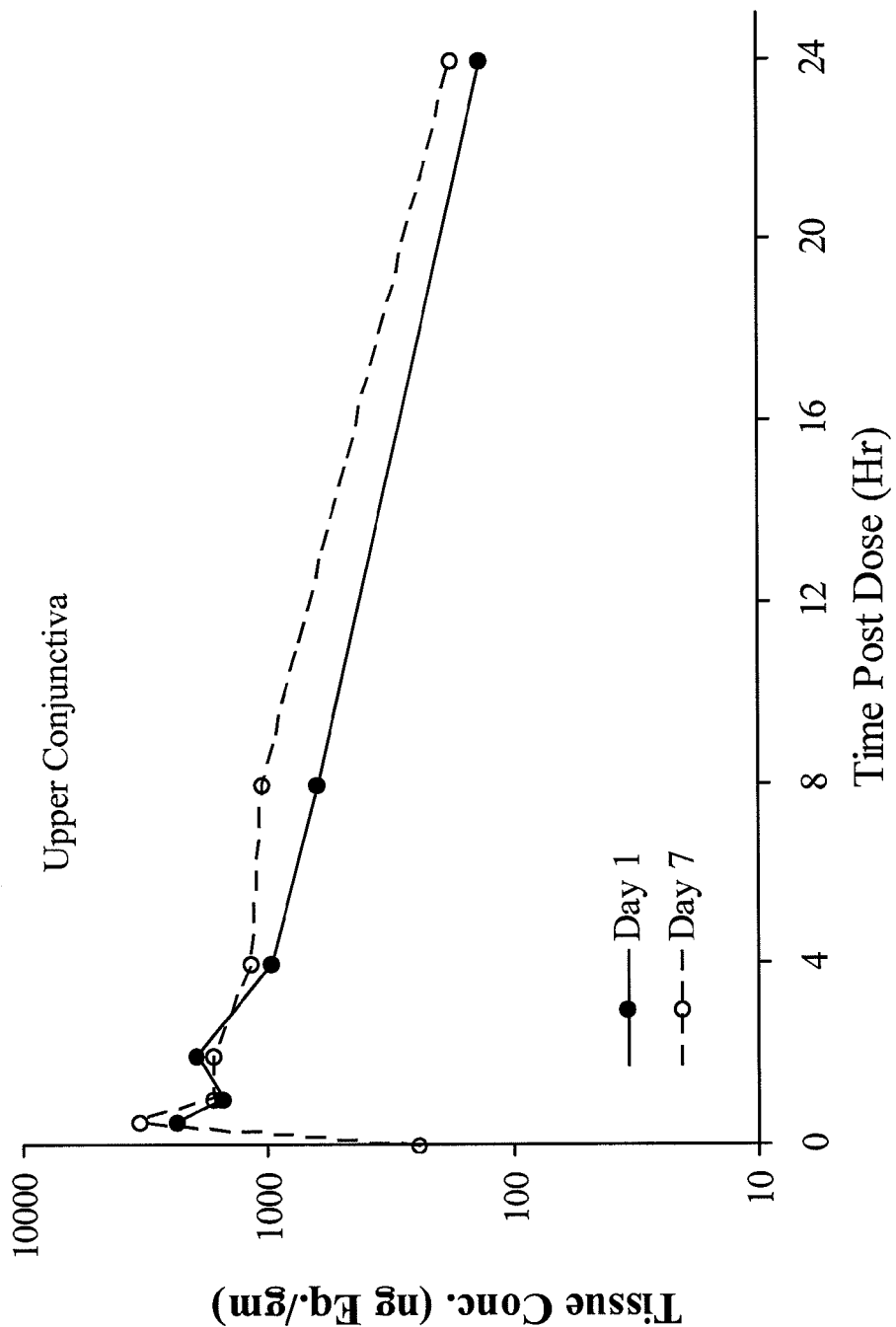
FIGS. 5A-D show mean ocular tissue and fluid concentrations of voclosporin after a single (1 day) or repeat (7 days), bilateral, once daily, topical dose of a mixed micellar pharmaceutical composition of the presently disclosed embodiments having $^{14}$C-voclosporin to female New Zealand White Rabbits.
Figure 5B:
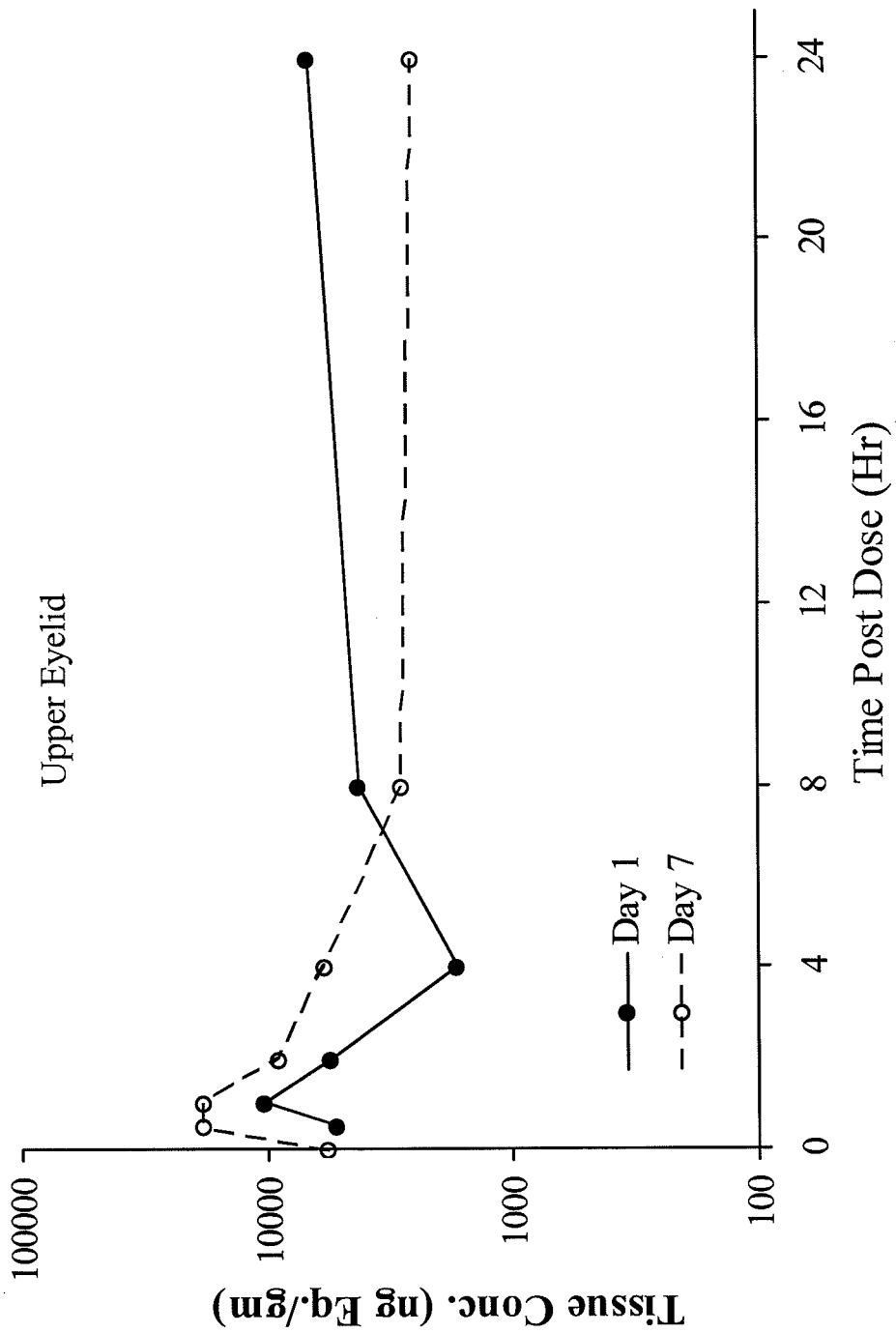
Figure 5C:
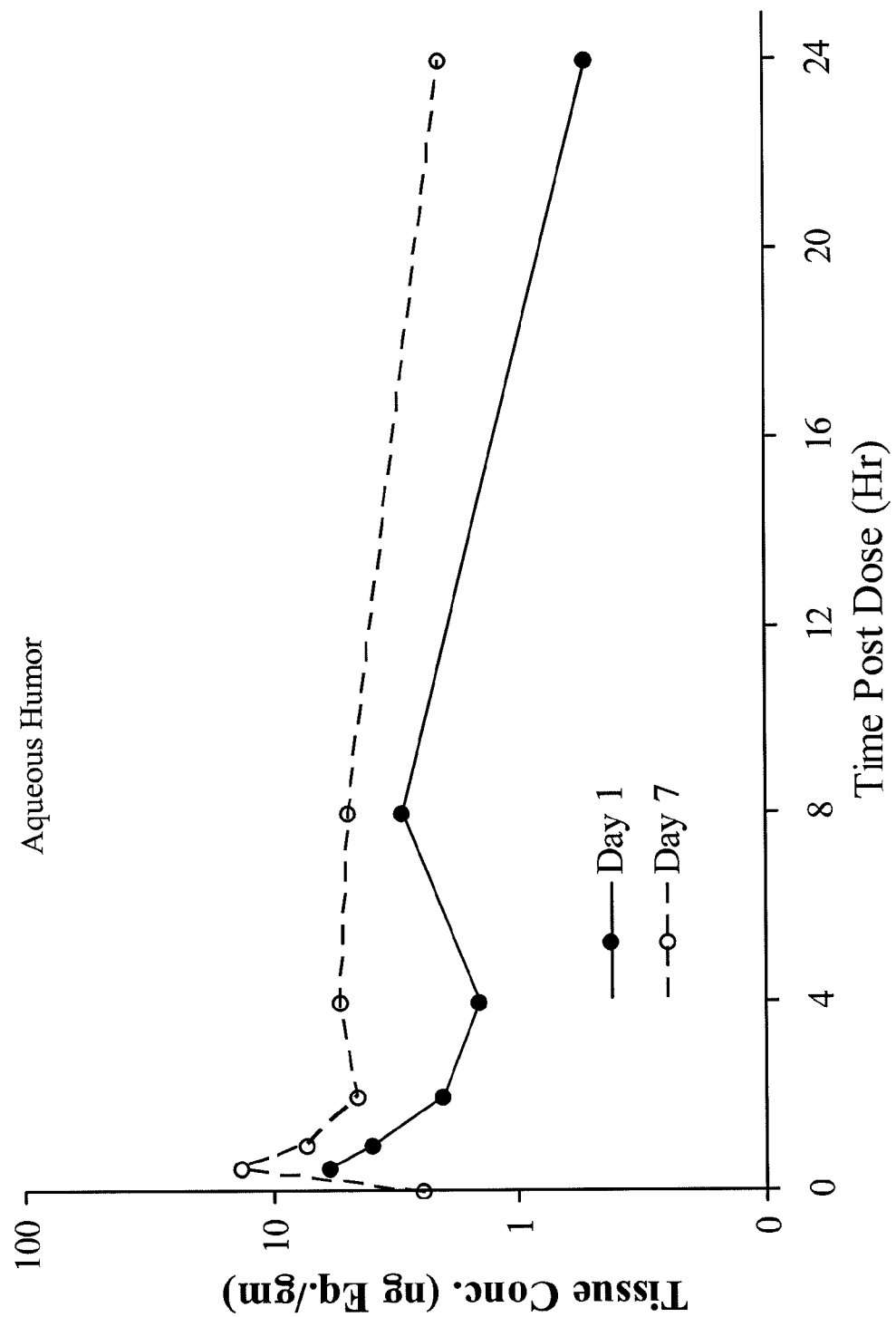
Figure 5D:
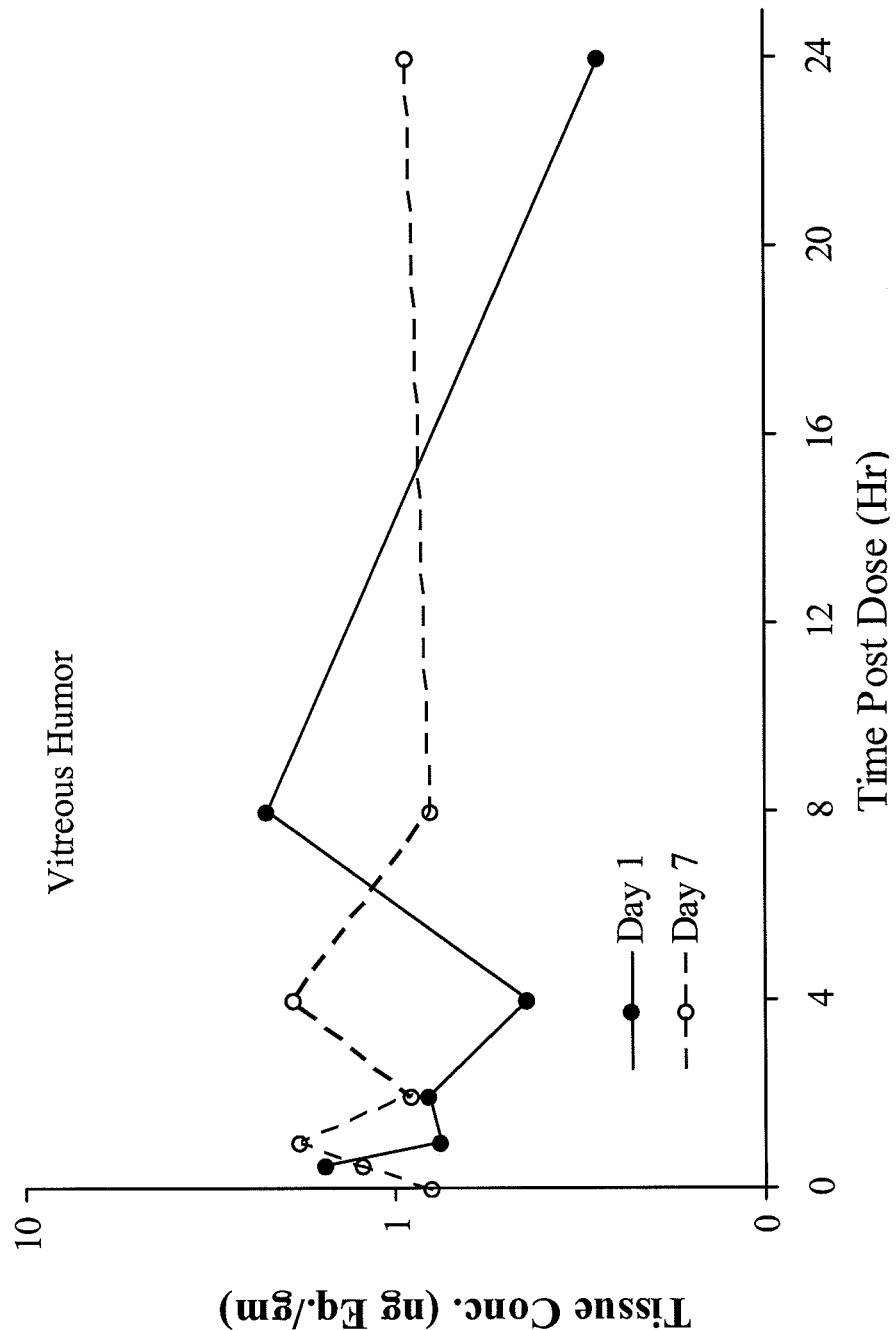

FIGS. 5A-D show mean ocular tissue and fluid concentrations of $^{14}$C-voclosporin after a single (1 day) or repeat (7 days), bilateral, once daily, topical dose of the 0.2% $^{14}$C-voclosporin mixed micellar formulation to female New Zealand White Rabbits (FIG. 5A, upper conjunctiva; FIG. 5B, upper eyelid; FIG. 5C, aqueous humor; and FIG. 5D, vitreous humor).

Figure 6A:
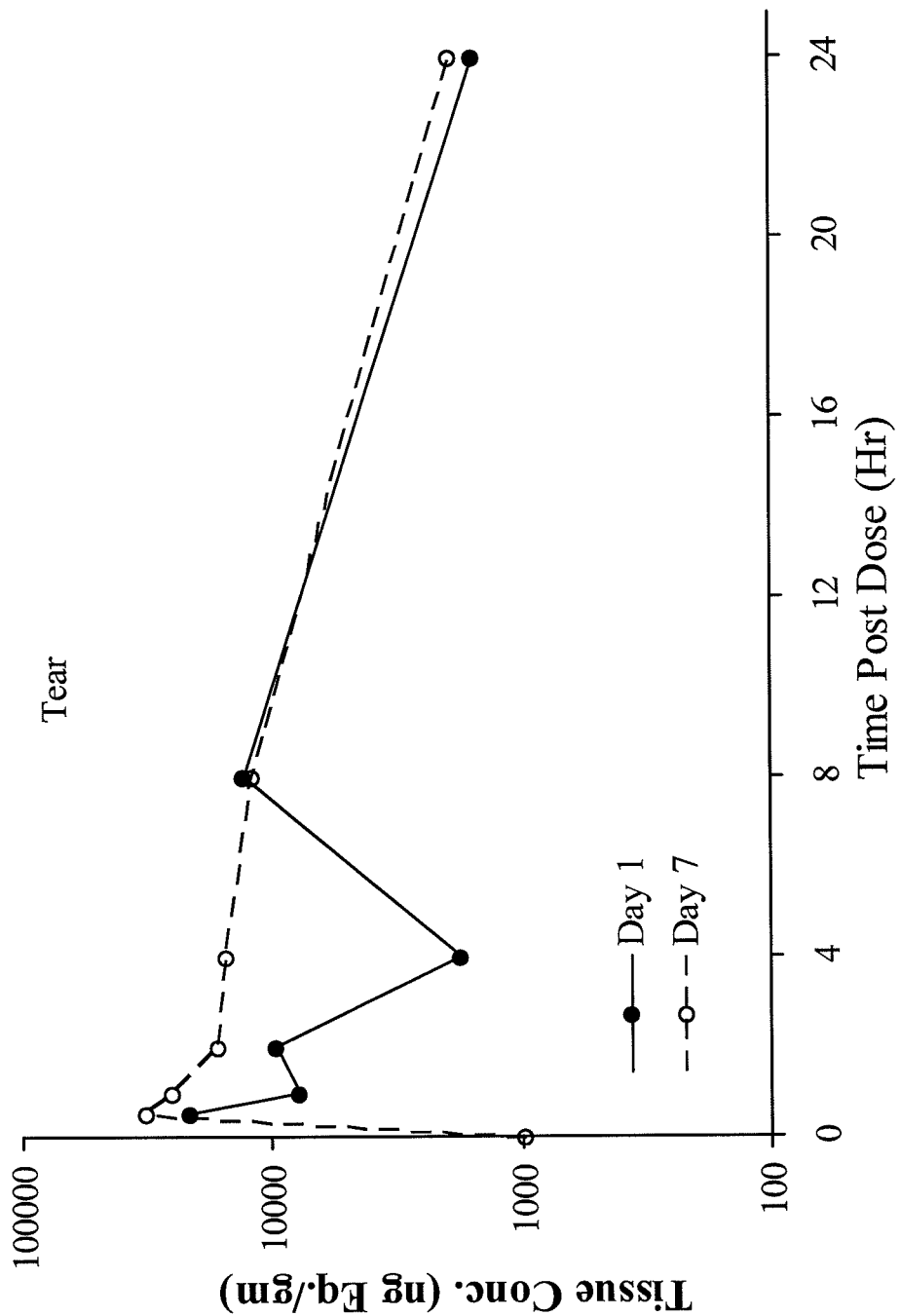
FIGS. 6A-D show mean ocular tissue and fluid concentrations of voclosporin after a single (1 day) or repeat (7 days), bilateral, once daily, topical dose of a mixed micellar pharmaceutical composition of the presently disclosed embodiments having $^{14}$C-voclosporin to female New Zealand White Rabbits.
Figure 6B:
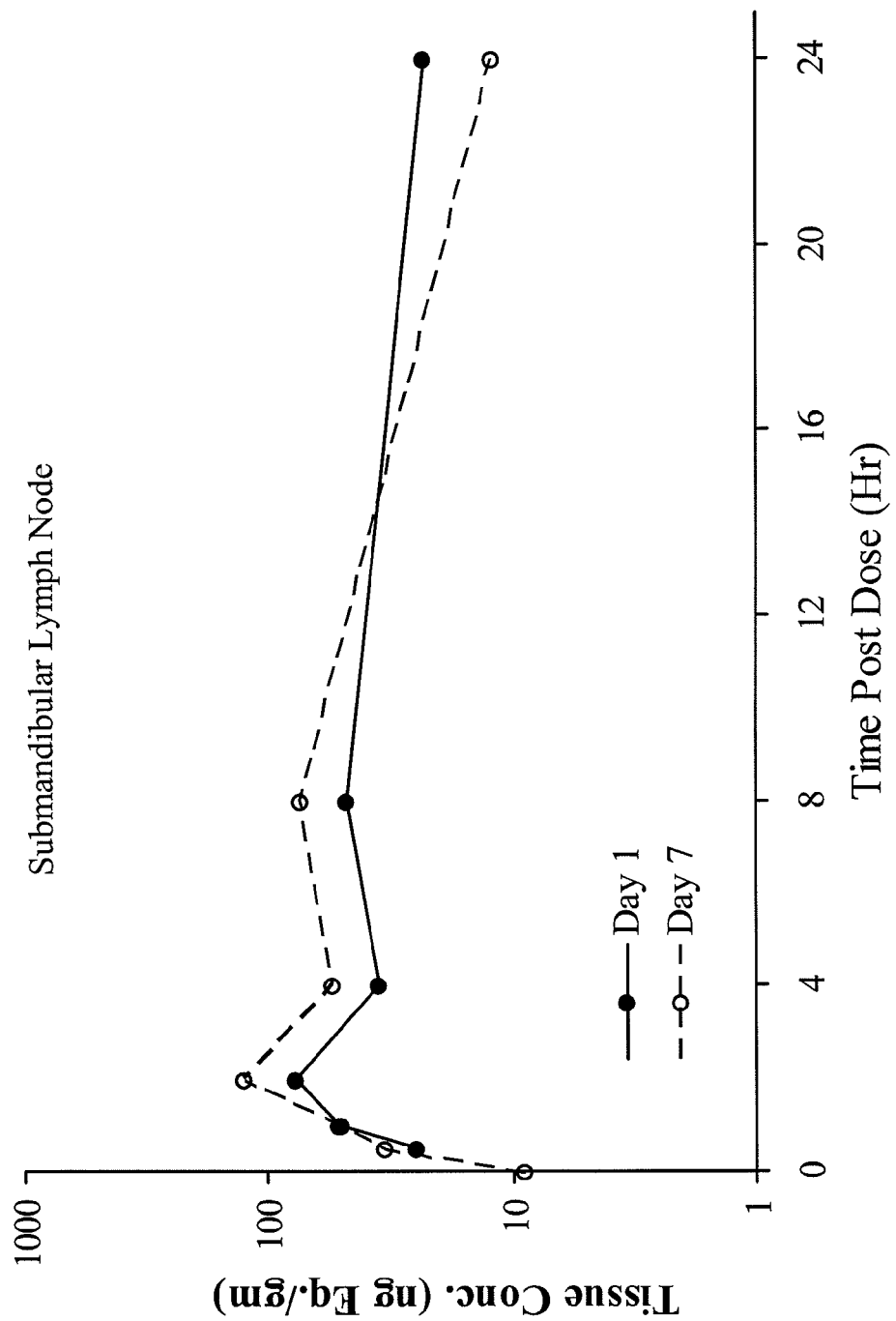
Figure 6C:
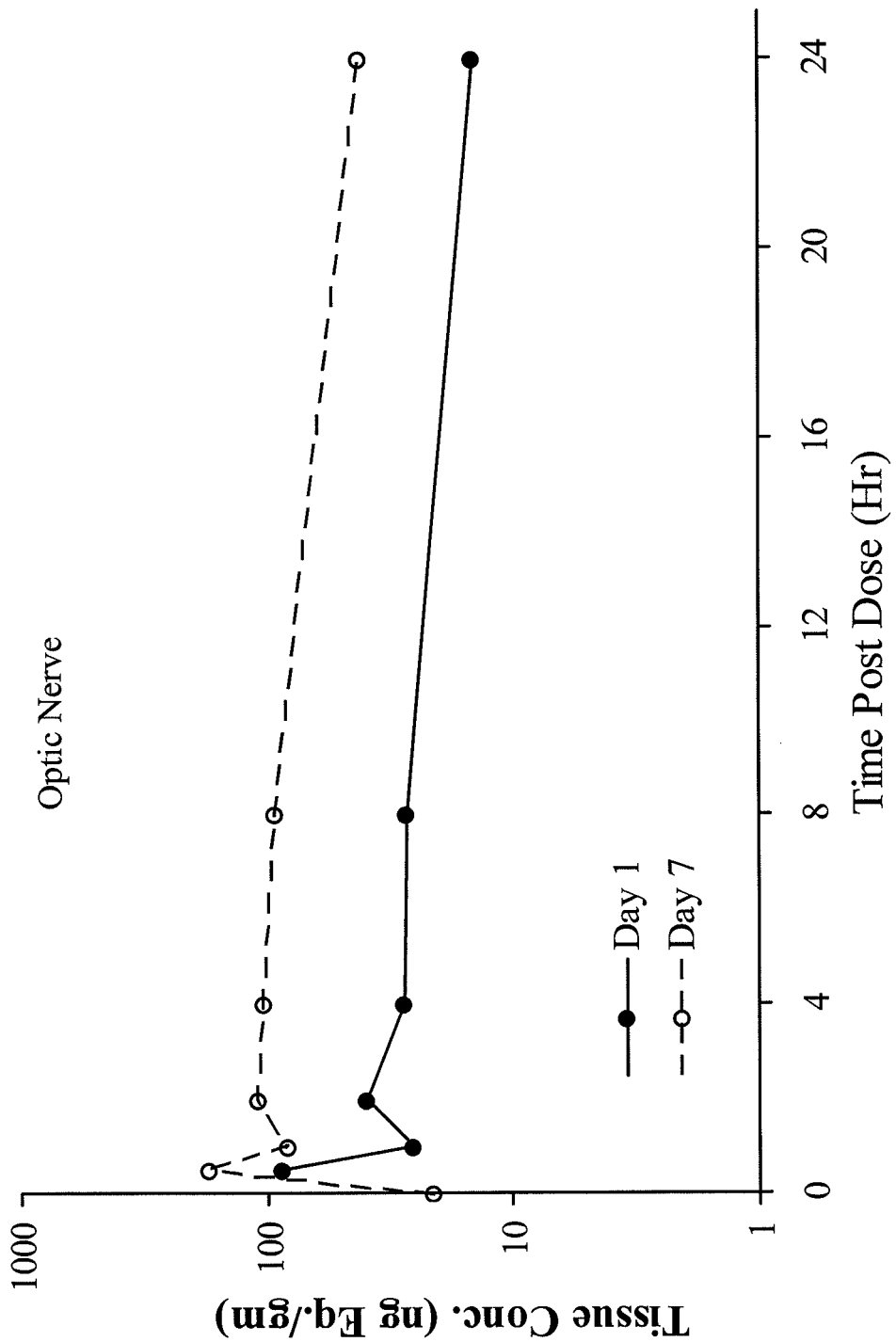
Figure 6D:
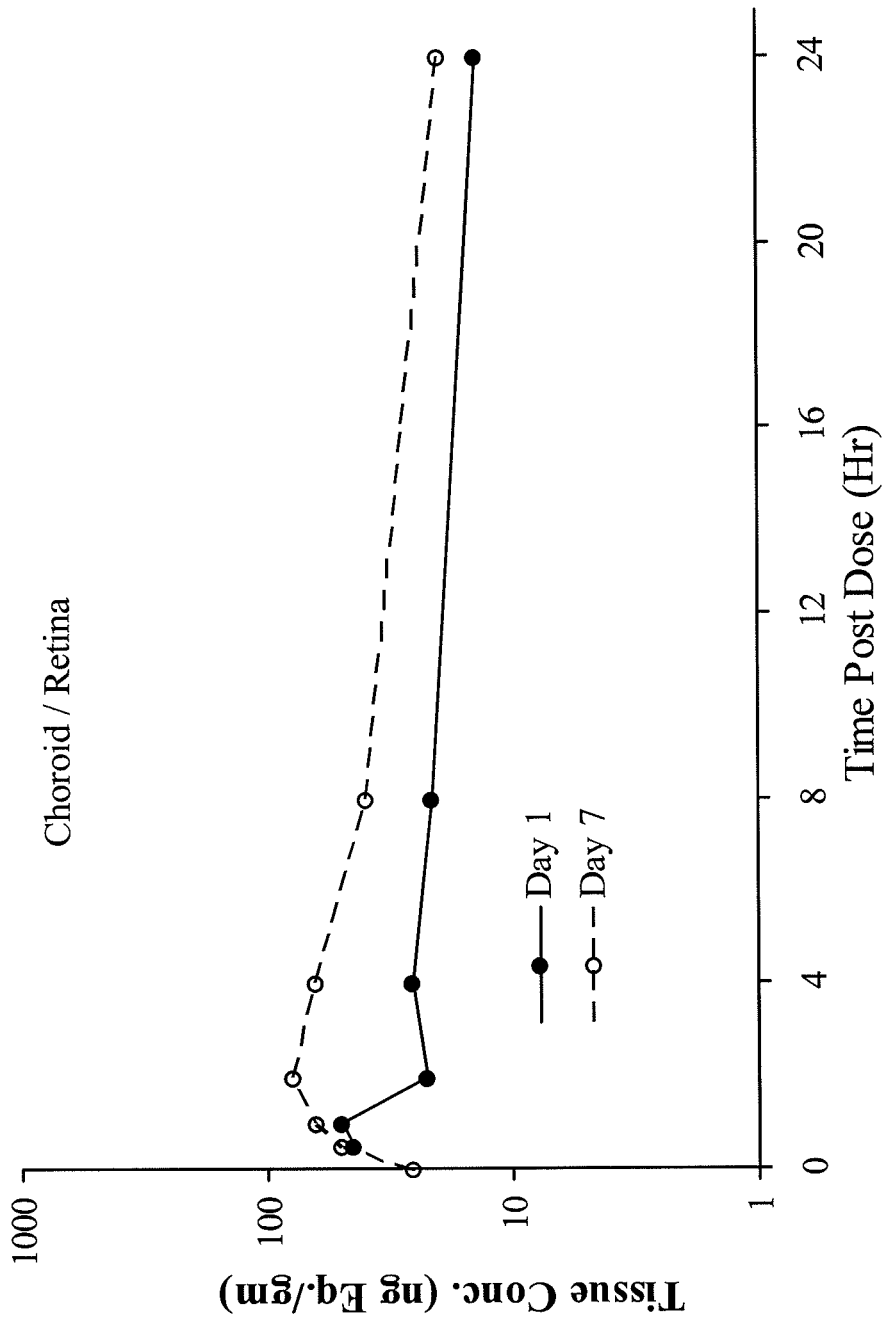

FIGS. 6A-D show mean ocular tissue and fluid concentrations of $^{14}$C-voclosporin after a single (1 day) or repeat (7 days), bilateral, once daily, topical dose of the 0.2% $^{14}$C-voclosporin mixed micellar formulation to female New Zealand White Rabbits (FIG. 6A, tears; FIG. 6B, lymph node; FIG. 6C, optic nerve; and FIG. 6D, choroid/retina).

Figure 7:
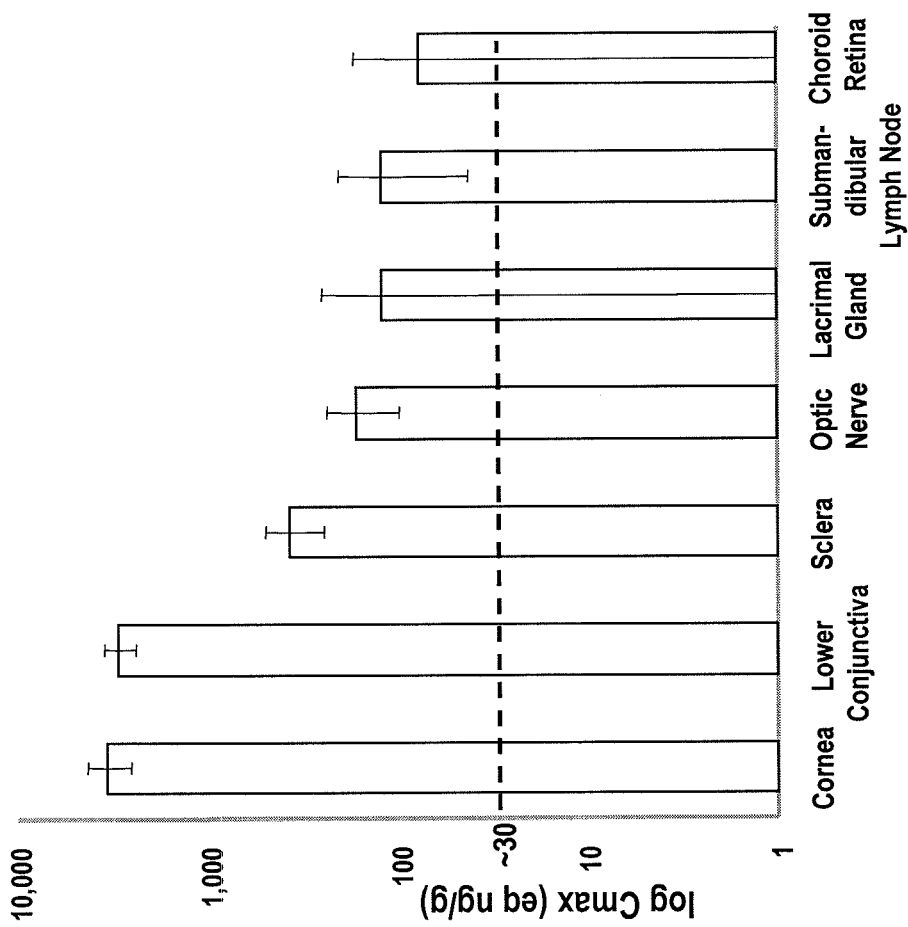
FIG. 7 is a graph showing $C_{max}$ values of voclosporin after repeat (7 day), bilateral, once daily, topical dose of a mixed micellar pharmaceutical composition of the presently disclosed embodiments having $^{14}$C-voclosporin to female New Zealand White Rabbits.

FIG. 7 is a graph showing $C_{max}$ values of $^{14}$C-voclosporin after repeat (7 day), bilateral, once daily, topical dose of the 0.2% $^{14}$C-voclosporin mixed micellar formulation to female New Zealand White Rabbits.

Potential Accumulation of $^{14}$C-Voclosporin-Derived Radioactivity:

Ocular exposure to $^{14}$C-voclosporin ocular exposure was increased 2.8 to 6.7 fold in cornea, lacrimal gland, iris/ciliary body and lens after 7 days of once daily, bilateral ocular administration of $^{14}$C-voclosporin (35 µL, 70 ng) (see Table 40). After multiple dosing (see Tables 40-43 and FIGS. 3-7), even though the $C_{max}$-repeat dose: $C_{max}$-single dose ratio was elevated in selected tissues, the overall levels of voclosporin were well below the surface tissue levels indicating minimal tissue accumulation. Also, comparable $t_{1/2}$ after single or repeat dosing strongly suggested minimal tissue accumulation.

Potential for Melanin Binding:

Following a single dose of $^{14}$C-voclosporin to DB rabbits, ocular tissue concentrations (e.g., $C_{max}$) were not significantly different from NZW rabbits, suggesting a lack of melanin binding (see Table 42).

High levels of drug are achievable with one topical application (single dose) of the compositions of the present disclosure. More particularly, high drug levels were maintained in ocular tissues for up to, and beyond, 24 hours post-administration, suggesting that QD (once daily) dosing is achievable using the compositions of the present disclosure. The concentration of drug is high in tissues in the front of the eye (cornea, conjunctiva, sclera) and at the back of the eye (retina, optic nerve) but minimal in the middle of the eye (aqueous and vitreous humor), suggesting transport of the drug by a mechanism other than passive transport through the eye. The high drug levels achieved at the back of the eye make topical administration of the compositions of the present disclosure feasible for the treatment of diseases of the back-of-the-eye (e.g., retinal, diseases involving optic nerve such as glaucoma). Various water-insoluble drugs can be used with the compositions of the present disclosure, including, but not limited to, calcineurin and mTOR inhibitors. Very high levels, especially in target tissues such as lachrymal gland, have been shown with the compositions of the present disclosure.

Concentrations of $^{14}$C-voclosporin-derived radioactivity (ng eq/g tissue) that exceeded therapeutic levels ($\geq$10 ng eq/g tissue) were measured in all ocular tissues except in the lens and ocular fluids (aqueous humor, vitreous humor) after single and repeat ocular applications. Blood levels were at the lower limit of quantification (LLOQ) suggesting minimal systemic exposure, and there was minimal distribution of $^{14}$C-vocloscporin to the contralateral, non-treated eye, likely due to the grooming behavior of animals.

Ocular exposure to $^{14}$C-voclosporin in the mixed micellar formulation of the present disclosure, as demonstrated by $C_{max}$ and AUC, varied widely among the ocular tissues. $^{14}$C-voclosporin exposure was highest in the ocular adnexa and exterior tissues (cornea, sclera, lower bulbar conjunctiva, lower eyelid, nictitating membrane, upper bulbar conjunctiva and upper eyelid) and tears, and lowest in the interior ocular tissues and fluids (vitreous humor, lens, aqueous humor); and in the middle range in the iris/ciliary body, lacrimal gland, submandibular lymph nodes, choroid/retina and optic nerve. Most ocular tissue levels thus exceed the 10 ng eq/g level needed for the biologic effect.

After once a day, daily ocular applications of $^{14}$C-voclosporin in a mixed micellar formulation for 7 days, concentrations of $^{14}$C-voclosporin in target tissues (e.g., conjunctiva, cornea, and lacrimal gland) remained at therapeutic levels even at the 24-hour mark, supporting once daily (QD) dosing is possible with an aqueous mixed micellar composition of the presently disclosed embodiments.

All patents, patent applications, and published references cited herein are hereby incorporated by reference in their entirety. It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A pharmaceutical composition in the form of mixed micelles, comprising:
    a calcineurin inhibitor or a mammalian target of rapamycin (mTOR) inhibitor;
    vitamin E tocopherol polyethylene glycol succinate (TPGS) with a hydrophilic/lipophilic balance (HLB) index greater than about 10; and
    octoxynol-40 with an HLB index of greater than about 13,
wherein an absolute difference between the HLB index of the vitamin E TPGS and the HLB index of the octoxynol-40 is greater than about 3, and
wherein the composition is in the form of mixed micelles having the vitamin E TPGS and the octoxynol-40.

2. The pharmaceutical composition of claim 1 wherein the calcineurin inhibitor or the mTOR inhibitor includes one of voclosporin, cyclosporine A, pimecrolimus, tacrolimus, sirolimus, temsirolimus, everolimus, analogs thereof, pharmaceutically acceptable salts thereof, or combinations thereof.

3. A pharmaceutical composition in the form of mixed micelles, comprising:
    a calcineurin inhibitor;
    vitamin E tocopherol polyethylene glycol succinate (TPGS); and
    octoxynol-40,
wherein the composition is in the form of mixed micelles having the vitamin E TPGS and the octoxynol-40 and is suitable for topical application to ocular tissue.

4. The pharmaceutical composition of claim 3 wherein the composition forms optically clear mixed micelles.

5. The pharmaceutical composition of claim 3 wherein the calcineurin inhibitor includes one of voclosporin, cyclosporine A, pimecrolimus, tacrolimus, analogs thereof, pharmaceutically acceptable salts thereof, or combinations thereof.

6. The pharmaceutical composition of claim 3 wherein the calcineurin inhibitor is voclosporin.

7. The pharmaceutical composition of claim 3 wherein the calcineurin inhibitor is present from about 0.01 weight percent to about 10 weight percent of a total volume of the composition.

8. The pharmaceutical composition of claim 3 wherein the vitamin E TPGS is present in from about 0.01 wt % to about 20 wt % of a total volume of the composition.

9. The pharmaceutical composition of claim 3 wherein the octoxynol-40 is present in from about 0.001 wt % to about 10 wt % of a total volume of the composition.

10. The pharmaceutical composition of claim 3 further comprising one or more bioadhesive polymers selected from the group consisting of polyvinylpyrrolidone (PVP)-K-30, PVP-K-90, hydroxypropyl methylcellulose (HPMC), hydroxypropyl cellulose (HEC), and polycarbophil.

11. The pharmaceutical composition of claim 3 further comprising one or more additives selected from the group consisting of trehalose, mannose, D-galactose, and lactose.

12. A pharmaceutical composition in the form of mixed micelles, comprising:
    a mammalian target of rapamycin (mTOR) inhibitor;
    vitamin E tocopherol polyethylene glycol succinate (TPGS); and
    octoxynol-40,
wherein the composition is in the form of mixed micelles having the vitamin E TPGS and the octoxynol-40 and is suitable for topical application to ocular tissue.

13. The pharmaceutical composition of claim 12 wherein the composition forms optically clear mixed micelles.

14. The pharmaceutical composition of claim 12 wherein the mTOR inhibitor includes one of sirolimus, temsirolimus, everolimus, analogs thereof, pharmaceutically acceptable salts thereof, or combinations thereof.

15. An artificial tear composition comprising an aqueous solution of mixed micelles, the mixed micelles formed from vitamin E tocopherol polyethylene glycol succinate (TPGS) and octoxynol-40, wherein the composition is in the form of mixed micelles having the vitamin E TPGS and the octoxynol-40.

16. The composition of claim 15 wherein the aqueous solution includes various ingredients chosen from one of hydrophilic polymer excipients, tonicity agents, buffers, sugars selected from trehalose, mannose, D-galactose, and lactose, preservatives, co-solvents or antioxidants.

17. The composition of claim 15 wherein the aqueous solution includes polyvinylpyrrolidone (PVP)-K-90, sodium chloride, at least one sodium phosphate and water.

18. The composition of claim 15 wherein the aqueous solution has a pH ranging from about 6.6 to about 7.0.

19. A pharmaceutical composition in the form of mixed micelles, comprising:
    voclosporin;
    vitamin E tocopherol polyethylene glycol succinate (TPGS); and
    octoxynol-40,
wherein the composition is in the form of mixed micelles having the vitamin E TPGS and the octoxynol-40 and is suitable for topical application to ocular tissue.

20. The pharmaceutical composition of claim 19 wherein the voclosporin is a trans-version of the voclosporin.

21. The pharmaceutical composition of claim 19 wherein the voclosporin is present from about 0.01 wt % to about 10 wt % of a total volume of the composition.

22. The pharmaceutical composition of claim 19 wherein the vitamin E TPGS is present in from about 0.01 wt % to about 20 wt % of a total volume of the composition, and the octoxynol-40 is present in from about 0.001 wt % to about 10 wt % of a total volume of the composition.

23. The pharmaceutical composition of claim 19 wherein the voclosporin is capable of reaching a back of an eye.

24. The pharmaceutical composition of claim 19 wherein the voclosporin includes a trans-version of the voclosporin.

25. A pharmaceutical composition in the form of mixed micelles, comprising:
cyclosporine A;
vitamin E tocopherol polyethylene glycol succinate (TPGS); and
octoxynol-40,
wherein the composition is in the form of mixed micelles having the vitamin E TPGS and the octoxynol-40 and is suitable for topical application to ocular tissue.

26. The pharmaceutical composition of claim 25 wherein the cyclosporine A is present from about 0.01 wt % to about 10 wt % of a total volume of the composition.

27. The pharmaceutical composition of claim 25 wherein the cyclosporine A is present at about 0.2 wt % of a total volume of the composition.

28. The pharmaceutical composition of claim 25 wherein the vitamin E TPGS is present in from about 0.01 wt % to about 20 wt % of a total volume of the composition, and the octoxynol-40 is present in from about 0.001 wt % to about 10 wt % of a total volume of the composition.

29. The pharmaceutical composition of claim 25 wherein the cyclosporine A is capable of reaching a back of an eye.

30. A pharmaceutical composition in the form of mixed micelles, comprising:
tacrolimus;
vitamin E tocopherol polyethylene glycol succinate (TPGS); and
octoxynol-40,
wherein the composition is in the form of mixed micelles having the vitamin E TPGS and the octoxynol-40 and is suitable for topical application to ocular tissue.

31. The pharmaceutical composition of claim 30 wherein the tacrolimus is present from about 0.01 wt % to about 10 wt % of a total volume of the composition.

32. The pharmaceutical composition of claim 30 wherein the tacrolimus is present at about 0.2 wt % of a total volume of the composition.

33. The pharmaceutical composition of claim 30 wherein the vitamin E TPGS is present in from about 0.01 wt % to about 20 wt % of a total volume of the composition, and the octoxynol-40 is present in from about 0.001 wt % to about 10 wt % of a total volume of the composition.

34. The pharmaceutical composition of claim 30 wherein the tacrolimus is capable of reaching a back of an eye.

35. A pharmaceutical composition in the form of mixed micelles, comprising:
sirolimus;
vitamin E tocopherol polyethylene glycol succinate (TPGS); and
octoxynol-40,
wherein the composition is in the form of mixed micelles having the vitamin E TPGS and the octoxynol-40 and is suitable for topical application to ocular tissue.

36. The pharmaceutical composition of claim 35 wherein the sirolimus is present from about 0.01 wt % to about 10 wt % of a total volume of the composition.

37. The pharmaceutical composition of claim 35 wherein the sirolimus is present at about 0.2 wt % of a total volume of the composition.

38. The pharmaceutical composition of claim 35 wherein the vitamin E TPGS is present in from about 0.01 wt % to about 20 wt % of a total volume of the composition, and the octoxynol-40 is present in from about 0.001 wt % to about 10 wt % of a total volume of the composition.

39. The pharmaceutical composition of claim 35 wherein the sirolimus is capable of reaching a back of an eye.

40. The pharmaceutical composition of claim 1 wherein the composition is suitable for topical application to ocular tissue.

41. The pharmaceutical composition of claim 1 wherein the calcineurin inhibitor or mTOR inhibitor is capable of reaching a back of an eye.

42. The pharmaceutical composition of claim 1 wherein the calcineurin inhibitor or mTOR inhibitor is present from about 0.01 wt % to about 10 wt % of a total volume of the composition.

43. The pharmaceutical composition of claim 1 wherein the composition is an aqueous solution.

44. The pharmaceutical composition of claim 3 wherein the composition is an aqueous solution.

45. The pharmaceutical composition of claim 12 wherein the composition is an aqueous solution.

46. The pharmaceutical composition of claim 19 wherein the composition is an aqueous solution.

47. The pharmaceutical composition of claim 25 wherein the composition is an aqueous solution.

48. The pharmaceutical composition of claim 30 wherein the composition is an aqueous solution.

49. The pharmaceutical composition of claim 35 wherein the composition is an aqueous solution.

* * * * *